(12) United States Patent
Sugihara et al.

(10) Patent No.: US 10,066,248 B2
(45) Date of Patent: *Sep. 4, 2018

(54) METHOD OF PRODUCING LIPID BY USING β-KETOACYL-ACP SYNTHASE

(71) Applicant: Kao Corporation, Chuo-ku, Tokyo (JP)

(72) Inventors: Shinji Sugihara, Wakayama (JP); Tatsuro Ozaki, Wakayama (JP); Hiroko Endo, Wakayama (JP); Takeshi Saito, Wakayama (JP); Takuto Tojo, Wakayama (JP); Hiroyuki Ohta, Yokohama (JP); Koichi Hori, Machida (JP)

(73) Assignee: KAO CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/110,635

(22) PCT Filed: Feb. 23, 2015

(86) PCT No.: PCT/JP2015/054960
§ 371 (c)(1),
(2) Date: Jul. 8, 2016

(87) PCT Pub. No.: WO2015/133305
PCT Pub. Date: Sep. 11, 2015

(65) Prior Publication Data
US 2017/0044580 A1    Feb. 16, 2017

(30) Foreign Application Priority Data
Mar. 3, 2014 (JP) ................................ 2014-040536

(51) Int. Cl.
| | | |
|---|---|---|
| C12P 7/64 | (2006.01) |
| C12N 1/13 | (2006.01) |
| C12N 9/88 | (2006.01) |
| C12N 9/10 | (2006.01) |
| C12N 9/16 | (2006.01) |
| C12N 15/52 | (2006.01) |
| C12N 15/70 | (2006.01) |
| C12N 15/79 | (2006.01) |

(52) U.S. Cl.
CPC .......... *C12P 7/6436* (2013.01); *C12N 9/1029* (2013.01); *C12N 9/16* (2013.01); *C12N 9/88* (2013.01); *C12N 15/52* (2013.01); *C12N 15/70* (2013.01); *C12N 15/79* (2013.01); *C12P 7/64* (2013.01); *C12P 7/6409* (2013.01); *C12Y 203/01041* (2013.01); *C12Y 301/02014* (2013.01)

(58) Field of Classification Search
None
See application file for complete search history.

(56) References Cited

U.S. PATENT DOCUMENTS

| | | |
|---|---|---|
| 5,850,022 A | 12/1998 | Dehesh et al. |
| 9,828,613 B2 | 11/2017 | Ozaki |
| 2003/0054524 A1 | 3/2003 | Spener et al. |
| 2013/0102040 A1 | 4/2013 | Radakovits et al. |
| 2013/0198904 A1 | 8/2013 | Ramli et al. |
| 2013/0316410 A1 | 11/2013 | Franklin et al. |
| 2015/0307860 A1 | 10/2015 | Ozaki et al. |
| 2016/0130615 A1 | 5/2016 | Ozaki |
| 2017/0107545 A1 | 4/2017 | Tojo et al. |
| 2017/0114376 A1 | 4/2017 | Ozaki et al. |
| 2017/0335353 A1 | 11/2017 | Ozaki |
| 2017/0335354 A1 | 11/2017 | Ozaki |

FOREIGN PATENT DOCUMENTS

| | | |
|---|---|---|
| JP | 11-500902 A | 1/1999 |
| JP | 2001-309797 A | 11/2001 |
| JP | 2002-223788 A | 8/2002 |
| JP | 2002-542829 A | 12/2002 |
| JP | 2010-511377 A | 4/2010 |
| WO | WO 96/23892 A2 | 8/1996 |
| WO | WO 98/46776 A2 | 10/1998 |
| WO | WO 00/66750 A2 | 11/2000 |
| WO | WO 2008/129358 A2 | 10/2008 |
| WO | WO 2012/106560 A1 | 8/2012 |
| WO | WO 2014/103930 A1 | 7/2014 |
| WO | WO 2015/005139 A1 | 1/2015 |
| WO | WO 2015/194628 A1 | 12/2015 |
| WO | WO 2016/021481 A1 | 2/2016 |
| WO | WO 2016/076231 A1 | 5/2016 |

(Continued)

OTHER PUBLICATIONS

Sigma Chemical Company 1993 Catalog, p. 1089.*
GenBank Accession No. EWM28742, Feb. 2014, 2 pages.*
Sang, H., Mechanisms of Development 121:1179-1186, 2004 (Year: 2004).*
Radakovits et al., Eukar. Cell. 9:486-501, 2010 (Year: 2010).*
Voelker et al., J. Bacteriol. 176:7320-7327, 1994 (Year: 1994).*
International Search Report (ISR) for PCT/JP2015/054960; I.A. fd Feb. 23, 2015, dated May 26, 2015, from the Japan Patent Office, Tokyo, Japan.
International Preliminary Report on Patentability (IPRP), Chapter I of the Patent Cooperation Treaty, including the Written Opinion for PCT/JP2015/054960; I.A. fd Feb. 23, 2015, dated Sep. 6, 2016, by the International Bureau of WIPO, Geneva, Switzerland.

(Continued)

*Primary Examiner* — David Steadman
(74) *Attorney, Agent, or Firm* — Sterne, Kessler, Goldstein & Fox P.L.L.C.

(57) ABSTRACT

The present disclosure provides a gene encoding a protein having β-ketoacyl-ACP synthase activity having at least 60% or more identity with the amino acid sequence set forth in SEQ ID NO:1, the protein encoded by the gene, a method of producing a transformant by transforming a host with the gene, a transformant that is transformed with the gene, and a method of producing a lipid, especially, a lipid containing a medium chain fatty acid or ester thereof, by culturing the transformed host that expresses the gene. In some embodiments, the transformant also has a gene encoding an acyl-ACP thioesterase.

13 Claims, 6 Drawing Sheets

Specification includes a Sequence Listing.

(56) References Cited

FOREIGN PATENT DOCUMENTS

| WO | WO 2016/088511 A1 | 6/2016 |
|---|---|---|
| WO | WO 2016/190238 A1 | 12/2016 |
| WO | WO 2017/022740 A1 | 2/2017 |

OTHER PUBLICATIONS

Radakovits, R et al., "Draft genome sequence and genetic transformation of the oleaginous alga *Nannochloropis gaditana*," Nat Commun. Feb. 21, 2012;3:686. doi: 10.1038/ncomms1688, 10 pages plus 1 page Corrigendum, Nature Pub. Group, London, England.

Corteggiani Carpinelli, E et al., "Chromosome Scale Genome Assembly and Transcriptome Profiling of *Nannochloropsis gaditana* in Nitrogen Depletion," Molecular Plant 7(2), p. 323-335, Feb. 2014, DOI: http://dx.doi.org/10.1093/mp/sst120, Elsevier Inc.

Dehesh, K et al, "KAS IV: a 3-ketoacyl-ACP synthase from *Cuphea* sp. is a medium chain specific condensing enzyme," Plant J. Aug. 1998;15(3):383-90, Blackwell Scientific Publishers, Oxford, England.

International Search Report (ISR) for PCT/JP2015/071666; I.A. fd Jul. 30, 2015, dated Oct. 13, 2015 from the Japan Patent Office, Tokyo, Japan.

International Preliminary Report on Patentability (IPRP), Chapter I of the Patent Cooperation Treaty, including the Written Opinion for PCT/JP2015/071666; I.A. fd Jul. 30, 2015, dated Feb. 7, 2017, by the International Bureau of WIPO, Geneva, Switzerland.

Dehesh, K, "How can we genetically engineer oilseed crops to produce high levels of medium-chain fatty acids?", Eur J Lipid Sci Technol 103 (Oct. 11, 2001) 688-697, Wiley-VCH Verlag GmbH, Germany.

Slabaugh, MB et al.,"Condensing enzymes from *Cuphea wrightii* associated with medium chain fatty acid biosynthesis," Plant J. Mar. 1998;13(5):611-20, Blackwell Scientific Publishers, Oxford, England.

Beta-ketoacyl-ACP synthase II, Database DDBJ/EMBL/GenBank [online], Accession No. Q9M604, http://www.ncbi.nlm.nih.gov/protein/q9m604> Oct. 31, 2006 uploaded, [retrieved on Oct. 6, 2015] Cha T.S. et al., Definition: Beta-ketoacyl-ACP synthase II.

\* cited by examiner

{FIG. 1}
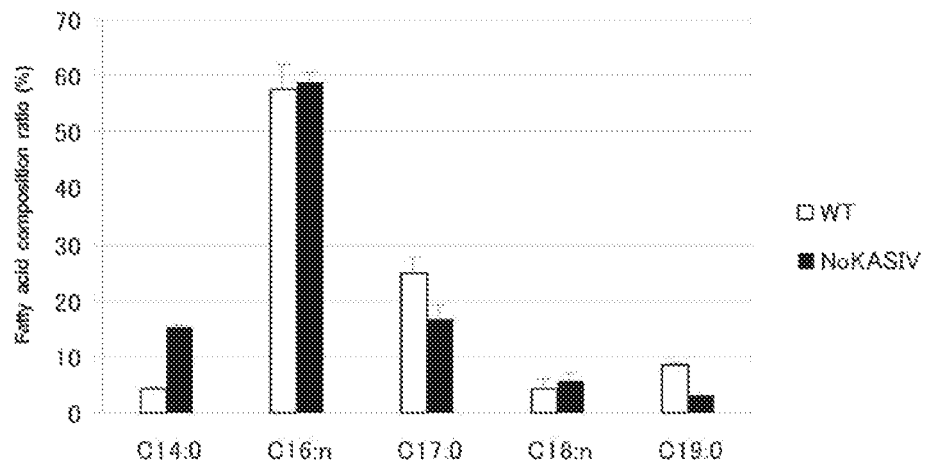
{FIG. 2}
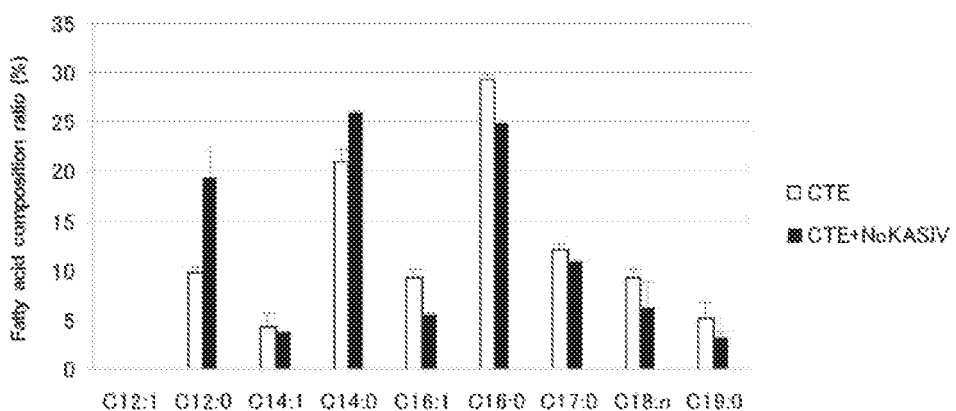
{FIG. 3}
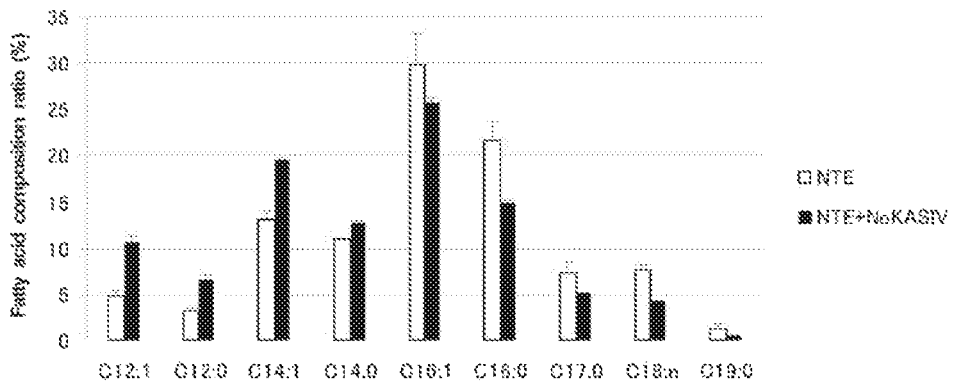

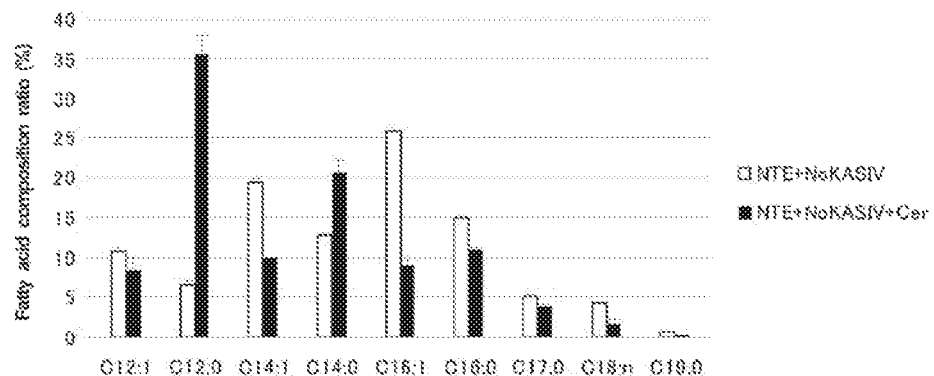
{FIG. 4}
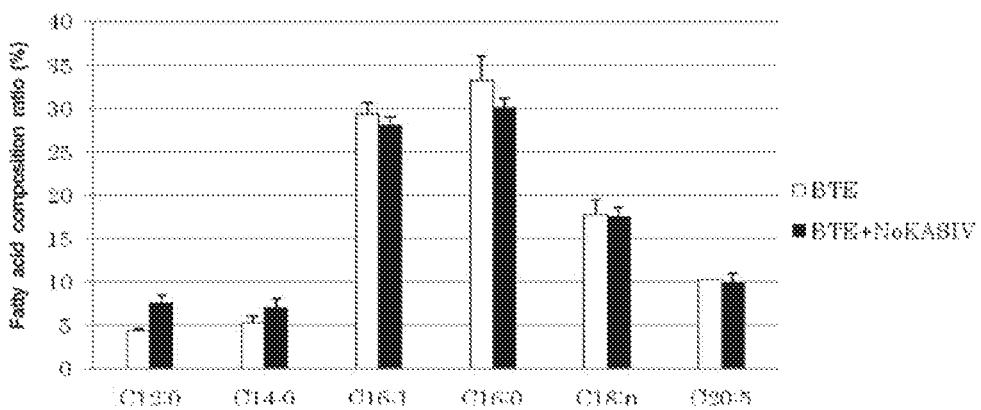
{FIG. 5}
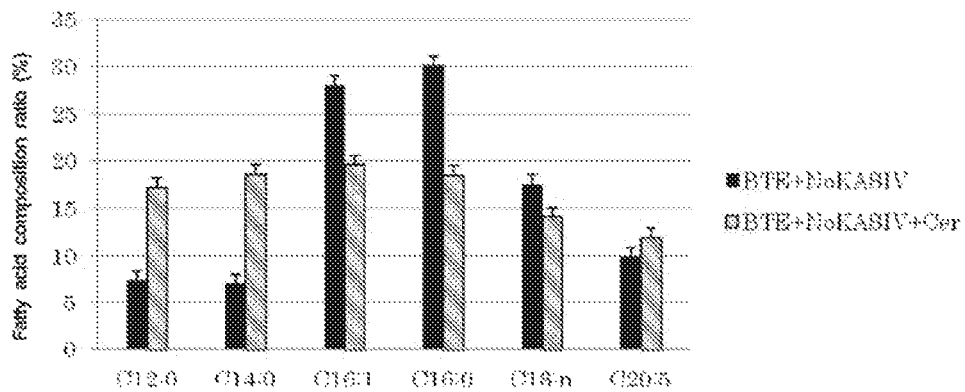
{FIG. 6}

{FIG. 7}
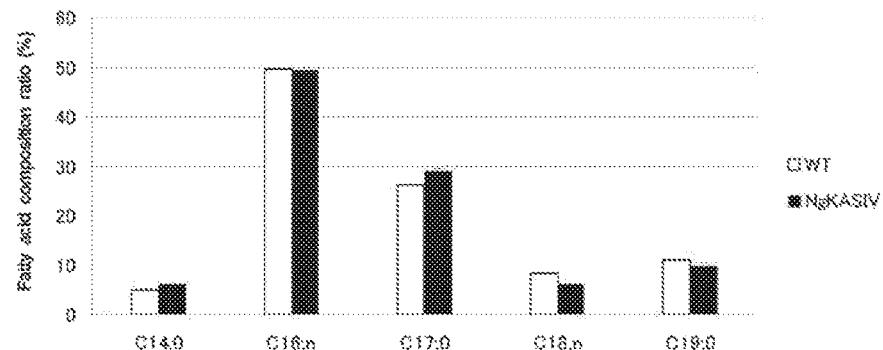
{FIG. 8}
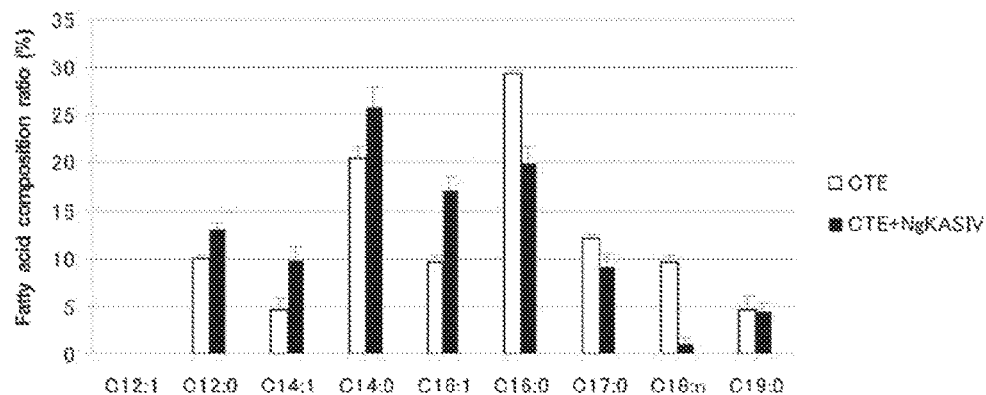
{FIG. 9}
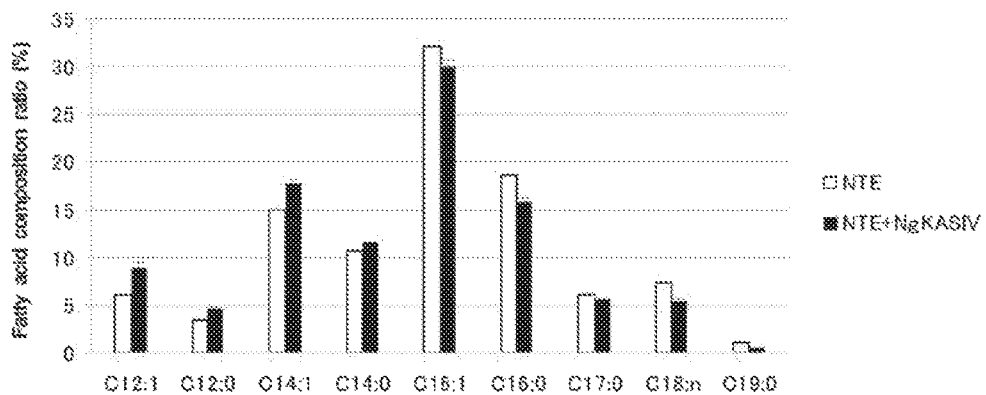

{FIG. 10}
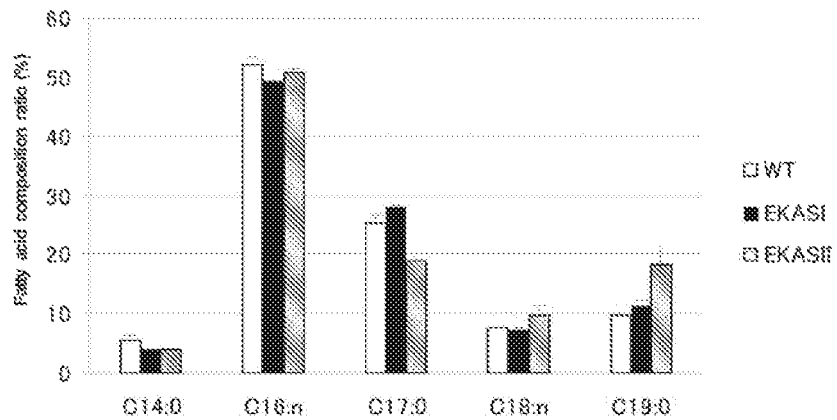
{FIG. 11}
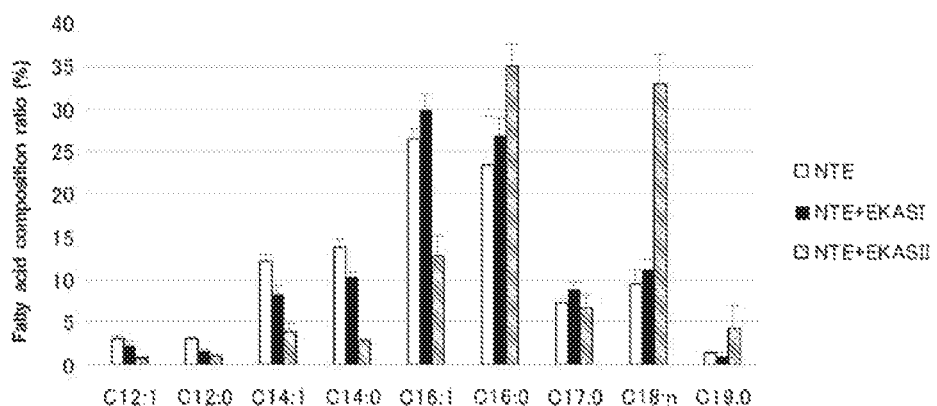
{FIG. 12}
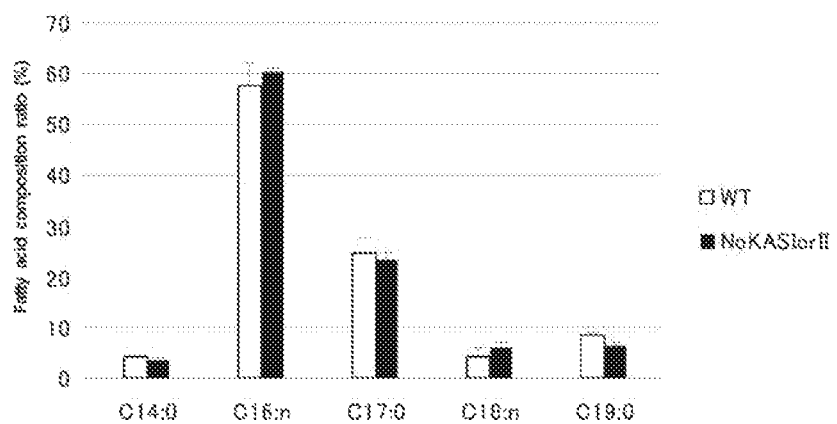

{FIG. 13}
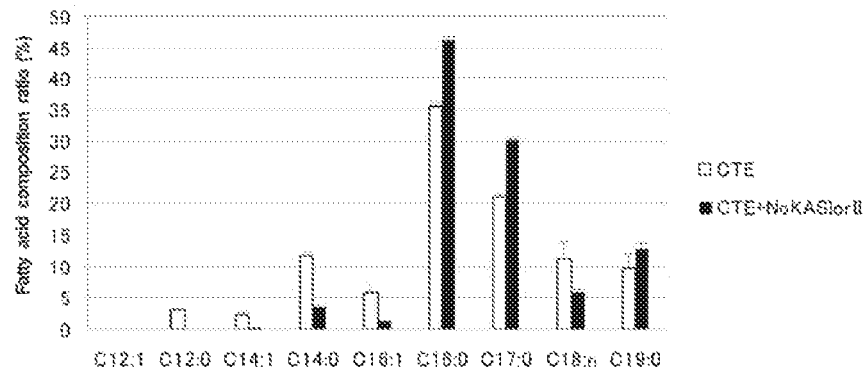
{FIG. 14}
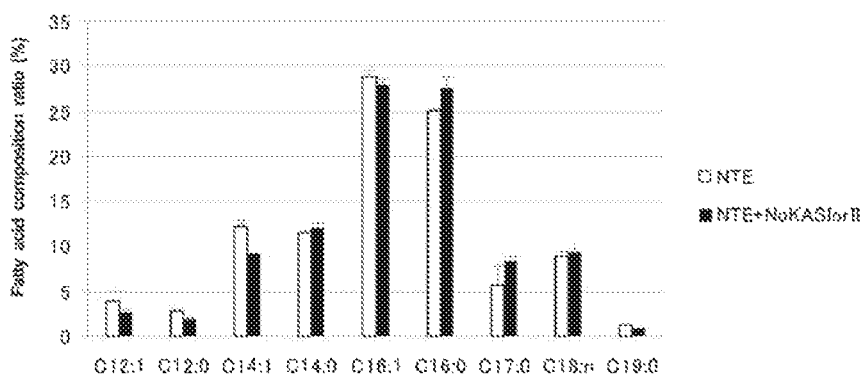
{FIG. 15}
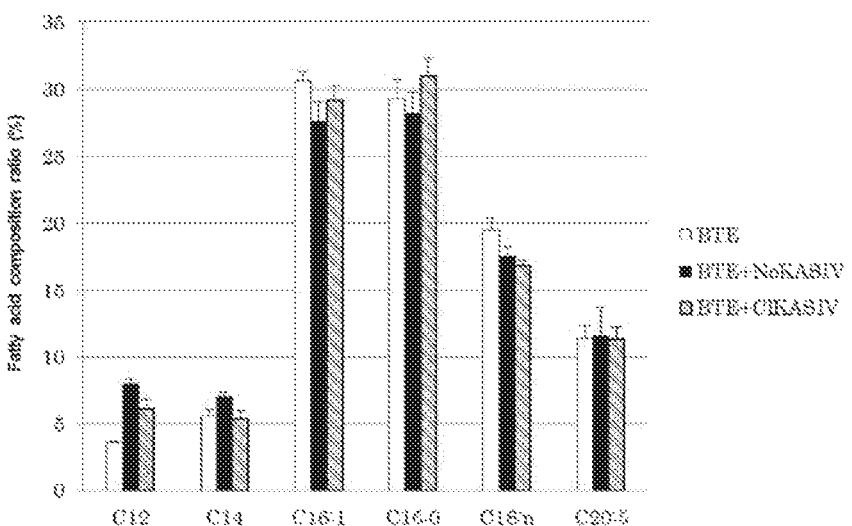

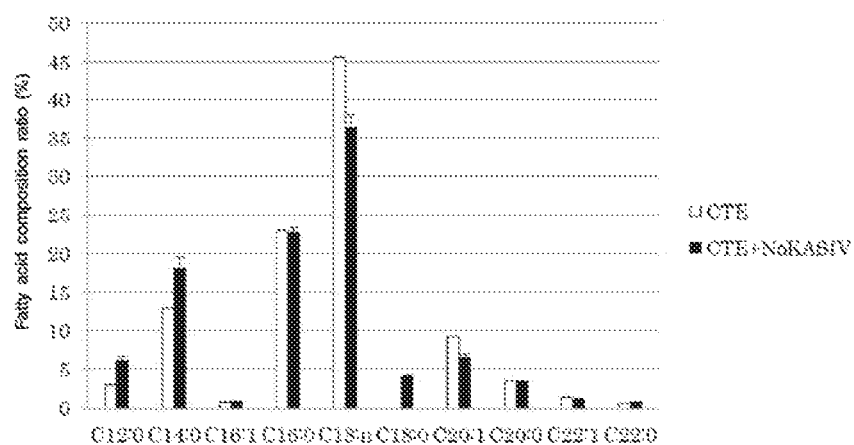
{FIG. 16}

METHOD OF PRODUCING LIPID BY USING β-KETOACYL-ACP SYNTHASE

REFERENCE TO SEQUENCE LISTING SUBMITTED ELECTRONICALLY

The content of the electronically submitted substitute sequence listing, file name 2537_1230001_SequenceListing_ascii.txt, size 85,404 bytes; and date of creation Sep. 23, 2016, filed herewith, is incorporated herein by reference in its entirety.

TECHNICAL FIELD

The present invention relates to β-ketoacyl-ACP synthase, and a method of producing a lipid by using the same.

BACKGROUND ART

Fatty acids are one of the principal components of lipids. In vivo, fatty acids are bonded to glycerin via an ester bond to form lipids such as triacylglycerol. Many animals and plants store and utilize fatty acids as an energy source. These fatty acids and lipids (fats and oils) stored in animals and plants are widely utilized for food or industrial use.

For example, higher alcohol derivatives that are obtained by reducing higher fatty acids having approximately 12 to 18 carbon atoms are used as surfactants. Alkyl sulfuric acid ester salts and alkylbenzenesurfonic acid salts are utilized as anionic surfactants, and polyoxyalkylene alkyl ethers, alkyl polyglycosides and the like are utilized as nonionic surfactants. These surfactants are used for detergents or disinfectants. As other higher alcohol derivatives, cationic surfactants such as alkylamine salts and mono- or dialkyl-quaternary amine salts are commonly used for fiber treatment agents, hair conditioning agents or disinfectants, and benzalkonium type quaternary ammonium salts are commonly used for disinfectants or antiseptics. Moreover, vegetable fats and oils are used also as raw materials of biodiesel fuels.

A fatty acid synthesis pathway of plants is localized in a chloroplast, in which an elongation reaction of a carbon chain is repeated starting from an acetyl-ACP (acyl-carrier-protein), and finally an acyl-ACP having 16 or 18 carbon atoms is synthesized. A β-ketoacyl-ACP synthase (β-ketoacyl-acyl-carrier-protein synthase: KAS) is an enzyme involved in control of chain length of an acyl group in the fatty acid synthesis pathway. In the plants, four kinds, namely KAS I, KAS II, KAS III and KAS IV are known to exist. KAS I to KAS IV are different in functions, respectively. KAS III functions in a stage of starting a chain length elongation reaction to elongate the acetyl-ACP having 2 carbon atoms to the acyl-ACP having 4 carbon atoms. In the subsequent elongation reaction, KAS I, KAS II and KAS IV are involved. KAS I is mainly involved in the elongation reaction to the palmitoyl-ACP having 16 carbon atoms, and KAS II is mainly involved in the elongation reaction to the stearoyl-ACP having 18 carbon atoms. On the other hand, it is believed that KAS IV is involved in the elongation reaction to medium chain acyl-ACP having 6 to 14 carbon atoms. KAS IV, in which less knowledge is obtained even in the plants, is considered to be KAS characteristic to the plants accumulating a medium chain fatty acid, such as Cuphea (Patent Literature 1, and Non-Patent Literature 1).

Recently, algae attract attention due to its usefulness in biofuel production. The algae can produce lipids that can be used as the biodiesel fuels through photosynthesis, and do not compete with foods. Therefore, the algae attract attention as next-generation biomass resources. Moreover, the algae are also reported to the effect mat the algae have higher lipid productivity and accumulation ability in comparison with plants. Research has started on a lipid synthesis mechanism of the algae and production technologies utilizing the mechanism, but unclear parts remain in many respects. Almost no report has been provided so far on the β-ketoacyl-ACP synthase of algae. In particular, no report has been made on KAS IV derived from the algae.

CITATION LIST

Patent Literatures

Patent Literature 1: WO 98/46776

Non-Patent Literatures

Non-Patent Literature 1: Dehesh K, Edwards P, Fillatti J, Slabaugh M, Byrne J., "KAS IV: A 3-ketoacyl-ACP synthase from *Cuphea* sp. is a medium chain specific condensing enzyme". The Plant Journal, 1998; 15(3), p. 383-390.

SUMMARY OF INVENTION

The present invention relates to a method of producing a lipid (hereinafter, the method is referred to as "the producing method of the present invention"), containing the following steps (1) and (2):

(1) introducing a gene encoding the following protein (a) or (b) into a host, and thereby obtaining a transformant, and (2) collecting a lipid from the resulting transformant:

(a) A protein consisting of an amino acid sequence set forth in SEQ ID NO: 1; and (b) A protein consisting of an amino acid sequence having 60% or more identity with the amino acid sequence of the protein (a), and having β-ketoacyl-ACP synthase activity.

The present invention also relates to a transformant obtained by introducing a gene encoding the protein (a) or (b) into a host (Hereinafter, referred to as "the transformant of the present invention").

The present invention relates to the following protein (a) or (c) (hereinafter, the protein is referred to as "the β-ketoacyl-ACP synthase of the present invention"), and a gene encoding this protein (hereinafter, the gene is referred to as "the β-ketoacyl-ACP synthase gene of the present invention"):

(a) A protein consisting of an amino acid sequence set forth in SEQ ID NO: 1; and (c) A protein consisting of an amino acid sequence having 91% or more identity with the amino acid sequence of the protein (a), and having β-ketoacyl-ACP synthase activity.

Other and further features and advantages of the invention will appear more fully from the following description, taken in connection with the accompanying drawings.

BRIEF DESCRIPTION OF DRAWINGS

FIG. 1 is a diagram showing the fatty acid composition in the lipid of the strain having the introduced NoKASIV gene.

FIG. 2 is a diagram showing the fatty acid composition in the lipid of the strain having the introduced NoKASIV gene and CTE gene.

FIG. 3 is a diagram showing the fatty acid composition in the lipid of the strain having the introduced NoKASIV gene and NoTE gene.

FIG. 4 is a diagram showing the fatty acid composition in the lipid of the strain having the introduced NoKASIV gene and NoTE gene cultured in cerulenin-containing medium.

FIG. 5 is a diagram showing the fatty acid composition in the lipid of the strain having the introduced NoKASIV gene and BTE gene.

FIG. 6 is a diagram showing the fatty acid composition in the lipid of the strain having the introduced NoKASIV gene and BTE gene cultured in the cerulenin-containing medium.

FIG. 7 is a diagram showing the fatty acid composition in the lipid of the strain having the introduced NgKASIV gene.

FIG. 8 is a diagram showing the fatty acid composition in the lipid of the strain having the introduced NgKASIV gene and CTE gene.

FIG. 9 is a diagram showing the fatty acid composition in the lipid of the strain having the introduced NgKASIV gene and NoTE gene.

FIG. 10 is a diagram showing the fatty acid composition in the lipid of the strain having the introduced EKASI gene and EKASII gene.

FIG. 11 is a diagram showing the fatty acid composition in the lipid of each of the strain having the introduced EKASI gene and NoTE gene, and the strain having the introduced EKASII gene and NoTE gene.

FIG. 12 is a diagram showing the fatty acid composition in the lipid of the strain having the introduced NoKASIorII gene.

FIG. 13 is a diagram showing the fatty acid composition in the lipid of the strain having the introduced NoKASIorII gene and CTE gene.

FIG. 14 is a diagram showing the fatty acid composition in the lipid of the strain having the introduced NoKASIorII gene and NoTE gene.

FIG. 15 is a diagram showing the fatty acid composition in the lipid of each of the strain having the introduced CIKASIV gene and BTE gene, and the strain having the introduced NoKASIV gene and BTE gene.

FIG. 16 is a diagram showing the fatty acid composition in the lipid of the strain having the introduced NoKASIV gene and CTE gene.

MODE FOR CARRYING OUT THE INVENTION

The present invention is contemplated for providing a method of producing a lipid by using a β-ketoacyl-ACP synthase derived from algae. Furthermore, the present invention is contemplated for providing a novel β-ketoacyl-ACP synthase derived from algae.

The present inventors made extensive studies about the β-ketoacyl-ACP synthases derived from algae. As a result, they found plural β-ketoacyl-ACP synthases derived from algae belonging to the genus *Nannochloropsis*. Then, the present inventors found that when a host was transformed by using them, productivity of medium chain fatty acids is significantly improved in the transformant. The present invention was completed based on these findings.

The transformant of the present invention is excellent in ability to produce the lipids, particularly, the medium chain fatty acids. Therefore, the production method of the present invention using the transformant is excellent in the productivity of medium chain fatty acids, and lipids containing as components the medium chain fatty acids. Further, the β-ketoacyl-ACP synthase and the gene encoding the same of the present invention can synthesize a medium acyl-ACP.

The β-ketoacyl-ACP synthase, the gene encoding this β-ketoacyl-ACP synthase, the transformant and the production method of the present invention can be suitably used for the industrial production of lipids, in particular fatty acids.

Hereinafter, the β-ketoacyl-ACP synthase, and the transformant and the method of producing a lipid using the same are described below in order.

In the present invention, the term "lipid(s)" covers simple lipids such as neutral lipids, wax, and ceramides; complex lipids such as phospholipids, glycolipids, and sulfolipids; and derived lipids obtained from these lipids such as fatty acids, alcohols, and hydrocarbons.

1. β-Ketoacyl-ACP Synthase

In the production method of the present invention, a gene encoding the protein consisting of an amino acid sequence set forth in SEQ ID NO: 1, or a gene encoding a protein functionally equivalent to the protein, is used. Specifically, in the present invention, a gene encoding the following protein (a) or (b) is used.

(a) A protein consisting of an amino acid sequence set forth in SEQ ID NO: 1.

(b) A protein consisting of an amino acid sequence having 60% or more identity with the amino acid sequence of the protein (a), and having β-ketoacyl-ACP synthase activity.

The protein consisting of the amino acid sequence set forth in SEQ ID NO: 1 is a novel β-ketoacyl-ACP synthase derived from an alga belonging to the genus *Nannochloropsis*, *Nannochloropsis oculata*.

The β-ketoacyl-ACP synthase is an enzyme involved in control of chain length of an acyl group in the fatty acid synthesis pathway. In a manner similar to plants, the fatty acid synthesis pathway of algae is localized in the chloroplast, the elongation reaction of the carbon chain is repeated starting from the acetyl-ACP, and finally an acyl-ACP having 16 or 18 carbon atoms (a composite consisting of an acyl group being a fatty acid residue and an acyl carrier protein) is synthesized. Then, thioesterases hydrolyze the thioester bond of the acyl-ACP to form free fatty acids.

In the first stage of the fatty acid synthesis, an acetoacetyl-ACP is formed by a condensation reaction between the acetyl-ACP and a malonyl-ACP. The β-ketoacyl-ACP synthase catalyzes the reaction. Then, the keto group of the acetoacetyl-ACP is reduced by a β-ketoacyl-ACP reductase, to produce a hydroxybutyryl-ACP. Subsequently, the hydroxybutyryl-ACP is dehydrated by a β-hydroxyacyl-ACP dehydrase, to produce a crotonyl-ACP. Finally, the crotonyl-ACP is reduced by an enoyl-ACP reductase, to produce a butyryl-ACP. The butyryl-ACP in which two carbon atoms are added to the carbon chain of the acyl group of the acetyl-ACP by a series of reactions. Hereinafter, the similar reactions are repeated to cause elongation of the carbon chain of the acyl-ACP, and an acyl-ACP having 16 or 18 carbon atoms is finally synthesized.

The protein (a) or (b) has β-ketoacyl-ACP synthase activity. In the present invention, an expression "the protein has β-ketoacyl-ACP synthase activity" means that the protein has activity to catalyze the condensation reaction of the acetyl-ACP or the acyl-ACP with the malonyl-ACP.

The β-ketoacyl-ACP synthase activity of a protein can be measured by, for example, introducing a fusion gene produced by linking a gene encoding the protein to the downstream of a promoter which functions in a host cell such as *Escherichia coli*, into a host cell which lacks a fatty acid degradation system, culturing the thus-obtained cell under the conditions suitable for the expression of the introduced gene, and analyzing any change caused thereby in the fatty acid composition of the cell or the cultured liquid by using a gas chromatographic analysis or the like.

Alternatively, the β-ketoacyl-ACP synthase activity can be measured by introducing a fusion gene produced by linking a gene encoding the protein to the downstream of a promoter which functions in a host cell such as *Escherichia coli*, into a host cell, culturing the thus-obtained cell under the conditions suitable for the expression of the introduced gene, and subjecting a disruption liquid of the cell to a chain length elongation reaction which uses acyl-ACPs, as substrates, prepared according to the method described in the above-mentioned Non-Patent Literature 1.

The β-ketoacyl-ACP synthase (KAS) catalyzes the condensation reaction of the acyl-ACP with the malonyl-ACP, and is categorized into KAS I, KAS II, KAS III and KAS IV according to substrate specificity. KAS III uses an acetyl-ACP having 2 carbon atoms as the substrate to catalyze the elongation reaction that the acetyl-ACP having 2 carbon atoms is converted to the acyl-ACP having 4 carbon atoms. KAS I mainly catalyzes the elongation reaction that the acyl-ACP having 4 carbon atoms is converted to the acyl-ACP having 16 carbon atoms, to synthesize the palmitoyl-ACP having 16 carbon atoms. KAS II mainly catalyzes the elongation reaction that the acyl-ACP having 16 carbon atoms is converted to the acyl-ACP having 18 carbon atoms, to synthesize the stearoyl-ACP having 18 carbon atoms. KAS IV catalyzes the elongation reaction that the acyl-ACP having 6 carbon atoms is converted to the acyl-ACP having 14 carbon atoms, to synthesize a medium chain acyl-ACP.

KAS I to KAS IV are known to be different in sensitivity to cerulenin being an inhibitor. KAS I and KAS II are sensitive to the cerulenin, while KAS III and KAS IV are insensitive to the cerulenin.

As shown in Examples mentioned later, the β-ketoacyl-ACP synthase of the protein (a) exhibits specificity to the medium chain acyl-ACP, and is considered to be KAS IV.

In the present invention, the term "specificity to the medium chain acyl-ACP" means that the β-ketoacyl-ACP synthase mainly uses an acyl-ACP having 4 to 12 carbon atoms as the substrate to catalyze the elongation reaction for the synthesis of the medium chain acyl-ACP having 14 carbon atoms. Hereinafter, the β-ketoacyl-ACP synthase having the specificity to the medium chain acyl-ACP is also referred to as a medium chain-specific β-ketoacyl-ACP synthase.

Moreover, in the present invention, the term "medium chain" used for the medium chain fatty add or the medium chain acyl-ACP means that the number of carbon atoms of the acyl group is 6 or more and 14 or less.

The specificity of the β-ketoacyl-ACP synthase to the medium chain acyl-ACP can be confirmed by, for example, introducing a fusion gene produced by (inking a gene encoding the protein to the downstream of a promoter which functions in a host cell such as *Escherichia coli*, into a host cell which lacks a fatty acid degradation system, culturing the thus-obtained cell under the conditions suitable for the expression of the introduced gene, analyzing any change caused thereby in the fatty acid composition of the cell or the cultured liquid by using a method such as a gas chromatographic analysis, and confirming the increase of the medium chain fatty acids. Alternatively, the specificity to the medium chain acyl-ACP can be confirmed by allowing, in the abode-described system, coexpression of medium chain-specific acyl-ACP thioesterase described later, and confirming the increase of the medium chain fatty acids in comparison with the specificity during medium chain-specific acyl-ACP thioesterase single expression. Alternatively, the specificity to the medium chain acyl-ACP can be confirmed by introducing a fusion gene produced by linking a gene encoding the protein to the downstream of a promoter which functions in a host cell such as *Escherichia coli*, into a host cell, culturing the thus-obtained cell under the conditions suitable for the expression of the introduced gene, and subjecting a disruption liquid of the cell to a chain length elongation reaction which uses acyl-ACPs, as substrates, prepared according to the method described in the above-mentioned Non-Patent Literature 1.

In the protein (b), the identity of the amino acid sequence is preferably 70% or more, more preferably 80% or more, further preferably 90% or more, further more preferably 91% or more, and further more preferably 95% or more, in view of β-ketoacyl-ACP synthase activity.

In the present specification, the identity of the amino acid sequence and nucleotide sequence is calculated through the Lipman-Pearson method (see Science, 227, pp. 1435, (1985)). Specifically, the identity can be determined through use of a homology analysis (homology search) program of genetic information processing software Genetyx-Win (Software Development Co., Ltd.) with the unit size to compare (ktup) being set to 2.

Preferred example of the protein (b) includes the following protein (a1).

(a1) A protein consisting of an amino add sequence set forth in SEQ ID NO: 58.

The protein consisting of the amino acid sequence set forth in SEQ ID NO: 58 is a β-ketoacyl-ACP synthase derived from *Nannochloropsis gaditana*. The amino acid sequence set forth in SEQ ID NO: 58 has about 90% identity with the amino acid sequence set forth in SEQ ID NO. 1. As shown in Examples mentioned later, the β-ketoacyl-ACP synthase (a1) also exhibits specificity to the medium chain acyl-ACP, and is considered to be KAS IV.

As the protein (b), a protein consisting of an amino acid sequence in which 1 or several amino acids (preferably 1 or more and 10 or less amino acids, more preferably 1 or more and 5 or less amino acids, and further preferably 1 or more and 3 or less amino acids) are mutated in the amino acid sequence of the protein (a), is also preferable.

Moreover, as the protein (b), a protein consisting of an amino acid sequence in which 1 or several amino acids (preferably 1 or more and 10 or less amino acids, more preferably 1 or more and 5 or less amino acids, and further preferably 1 or more and 3 or less amino acids) are mutated in the amino acid sequence of the protein (a1), is also preferable.

The above amino acid mutation includes deletion, substitution, insertion or addition of amino acid(s).

A method of introducing the mutation into an amino acid sequence includes a method of, for example, introducing a mutation into a nucleotide sequence encoding the amino acid sequence. A method of introducing the mutation includes a method of introducing a site-specific mutation. Specific examples of the method of introducing the site-specific mutation include a method of utilizing the Splicing overlap extension (SOE) PGR (Horton et al., Gene 77, 61-68, 1989), the ODA method (Hashimoto-Gotoh et al., Gene, 152, 271-276, 1995), and the Kunkel method (Kunkel, T. A., Proc. Natl. Acad. Sci. USA. 1985, 82, 488). Further, commercially available kits such as Site-Directed Mutagenesis System Mutan-SuperExpress Km kit (manufactured by Takara Bio), Transformer TM Site-Directed Mutagenesis kit (manufactured by Clonetech Laboratories), and KOD-Plus-Mutagenesis kit (manufactured by Toyobo) can also be utilized. Furthermore, a gene containing a desired mutation can also be obtained by introducing a genetic mutation at random, and then performing an evaluation of the enzyme activities and a gene analysis thereof by an appropriate method.

The protein (b) includes the following novel protein (c).
(c) A protein consisting of an amino acid sequence having 91% or more identity with the amino acid sequence of the protein (a), and having β-ketoacyl-ACP synthase activity.

From the viewpoint of improvement in productivity of the medium chain fatty acids, the protein (b) or (c) is preferably a protein having medium chain-specific β-ketoacyl-ACP synthase activity.

There are no particular limitations on the method for obtaining the above-described protein, and the protein may be obtained by chemical techniques or genetic engineering techniques that are ordinarily carried out. For example, a natural product-derived protein can be obtained through isolation, purification and the like from *Nannochloropsis oculata*. Furthermore, the protein can also be artificially synthesized based on the information for the amino acid sequence set forth in SEQ ID NO: 1, and protein synthesis may be carried out by chemical synthesis, or a recombinant protein may also be produced by gene recombination technologies, in the case of producing a recombinant protein, the β-ketoacyl-ACP synthase gene of the present invention described below can be used. In addition, the algae such as *Nannochloropsis oculata* can be used by purchasing the algae stored in private or public bio-related institutes or the like. For example, *Nannochloropsis oculata* NIES-2145 used in Examples can be obtained from National Institute for Environmental Studies (NIES).

Examples of the gene encoding the protein (a) or (b) include a gene consisting of the following DNA (d) or (e).
(d) A DNA consisting of a nucleotide sequence set forth in SEQ ID NO: 2.
(e) A DNA consisting of a nucleotide sequence having 60% or more identity with the nucleotide sequence of the DNA (d), and encoding a protein having β-ketoacyl-ACP synthase activity.

Examples of the nucleotide sequence encoding the amino acid sequence set forth in SEQ ID NO: 1 include a nucleotide sequence set forth in SEQ ID NO: 2. The gene consisting of the nucleotide sequence set forth in SEQ ID NO: 2 is a gene encoding the β-ketoacyl-ACP synthase derived from *Nannochloropsis oculata*.

In the DNA (e), from the point of view of β-ketoacyl-ACP synthase activity, the identity of the nucleotide sequence is preferably 65% or more, more preferably 70% or more, more preferably 75% or more, more preferably 78% or more, more preferably 80% or more, more preferably 90% or more, and more preferably 95% or more. The identity of the nucleotide sequence can be calculated through the method described above.

Preferred example of the DNA (e) includes the following DNA (d1).
(d1) A DNA consisting of a nucleotide sequence set forth in SEQ ID NO: 59.

The gene consisting of the nucleotide sequence set forth in SEQ ID NO: 59 is a β-ketoacyl-ACP synthase gene derived from *Nannochloropsis gaditana*. The nucleotide sequence set forth in SEQ ID NO: 59 has about 77% identity with the nucleotide sequence set forth in SEQ ID NO: 2.

The DNA (e) includes the following novel DNA (f).
(f) A DNA consisting of a nucleotide sequence having 78% or more identity with the nucleotide sequence of the DNA (d), and encoding a protein having β-ketoacyl-ACP synthase activity.

A method of obtaining the above-described β-ketoacyl-ACP synthase gene is not particularly limited, and the β-ketoacyl-ACP synthase gene can be obtained by ordinary genetic engineering techniques. For example, the β-ketoacyl-ACP synthase gene can be obtained by artificial synthesis based on the amino acid sequence set forth in SEQ ID NO: 1 or the nucleotide sequence set forth in SEQ ID NO: 2. The artificial synthesis of a gene can be achieved by utilizing, for example, the services of Invitrogen or the like. Furthermore, the gene can also be obtained by cloning from *Nannochloropsis oculata*. The cloning can be carried out by, for example, the methods described in Molecular Cloning—A LABORATORY MANUAL THIRD EDITION [Joseph Sambrook, David W. Russell, Cold Spring Harbor Laboratory Press (2001)] or the like.

2. Acyl-ACP Thioesterase

The transformant of the present invention preferably has a gene encoding an acyl-ACP thioesterase, as well as the gene encoding the protein (a) or (b), introduced into a host.

The acyl-ACP thioesterase is an enzyme that hydrolyzes the thioester bond of the acyl-ACP synthesized by a fatty acid synthetase such as the β-ketoacyl-ACP synthase to produce free fatty acids. The function of the acyl-ACP thioesterase terminates the fatty acid synthesis on the ACP, and then the thus-produced fatty acids are supplied to the synthesis of triglyceride and the like.

Therefore, lipid productivity of the transformant, particularly, productivity of fatty acids can be further improved by introducing the β-ketoacyl-ACP synthase gene and the acyl-ACP thioesterase gene into the host.

The acyl-ACP thioesterase that can be used in the present invention only needs to be the protein having acyl-ACP thioesterase activity. In the present invention, the "having acyl-ACP thioesterase activity" means having an activity of hydrolyzing the thioester bond of the acyl-ACP.

To date, several acyl-ACP thioesterases having different reaction specificities depending on the number of carbon atoms and the number of unsaturated bonds of the acyl group (fatty acid residue) constituting the acyl-ACP substrate are identified. Therefore, they are considered to be an important factor in determining the fatty acid composition of an organism.

As mentioned above, the protein (a) or (a1) is the medium chain-specific β-ketoacyl-ACP synthase. Therefore, the acyl-ACP thioesterase to be cointroduced thereinto is also preferably a thioesterase having the specificity to the medium chain acyl-ACP (hereinafter, also referred to as "medium chain-specific acyl-ACP thioesterase"). The productivity of medium chain fatty acids can be further improved by using the medium chain-specific acyl-ACP thioesterase. In particular, when a host originally having no medium chain-specific acyl-ACP thioesterase is used for transformation, cointroduction of the medium chain-specific acyl-ACP thioesterase is effective.

In the present invention, any known acyl-ACP thioesterases and proteins functionally equivalent to the known acyl-ACP thioesterases can be used. The acyl-ACP thioesterase to be used can be appropriately selected according to a kind of host or the like.

Specific examples thereof include *Umbellularia californica* acyl-ACP thioesterase (GenBank AAA34215.1, SEQ ID NO: 50, the nucleotide sequence of the gene encoding this thioesterase: SEQ ID NO: 51); *Cuphea calophylla* subsp. mesostemon acyl-ACP thioesterase (GenBank ABB71581); *Cocos nucifera* acyl-ACP thioesterase (Cn-FatB3; see Jing et al. BMC Biochemistry 2011, 12:44, SEQ ID NO: 46, the nucleotide sequence of the gene encoding this thioesterase: SEQ ID NO: 47); *Cinnamomum camphora* acyl-ACP thioesterase (GenBank AAC49151.1); *Myristica fragrans* acyl-ACP thioesterase (GenBank AAB71729); *Myristica fragrans* acyl-ACP thioesterase (GenBank AAB71730); *Cuphea Lanceolata* acyl-ACP thioesterase (GenBank CAA54060); *Cuphea hookeriana* acyl-ACP thioesterase (GenBank Q39513); *Ulumus americana* acyl-ACP thioesterase (GenBank AAB71731); *Sorghum bicolor* acyl-ACP thioesterase (GenBank EER87824); *Sorghum bicolor* acyl-ACP thioesterase (GenBank EER88593); *Cocos nucifera* acyl-ACP thioesterase (CnFatB1: see Jing et al. BMC Biochemistry 2011, 12:44); *Cocos nucifera* acyl-ACP thioesterase (CnFatB2: see Jing et al. BMC Biochemistry 2011, 12:44); *Cuphea viscosissima* acyl-ACP thioesterase (CvFat81: see Jing et al. BMC Biochemistry 2011, 12:44); *Cuphea viscosissima* acyl-ACP thioesterase (CvFatB2: see Jing et al. BMC Biochemistry 2011.12:44); *Cuphea viscosissima* acyl-ACP thioesterase (CvFatB3; see Jing et al. BMC Biochemistry 2011, 12:44); *Elaeis guineensis* acyl-ACP thioesterase (GenBank AAD42220): *Desulfovibrio vulgaris* acyl-ACP thioesterase (GenBank ACL08376); *Bacteriodes fragilis* acyl-ACP thioesterase (GenBank CAH09236); *Parabacteriodes distasonis* acyl-ACP thioesterase (GenBank ABR43801); *Bacteroides thetaiotaomicron* acyl-ACP thioesterase (GenBank AAO77182); *Clostridium asparagiforme* acyl-ACP threes-erase (GenBank EEG55387); *Bryanthella formatexigens* acyl-ACP thioesterase (GenBank EET61113); *Geobacillus* sp. acyl-ACP thioesterase (GenBank EDV77528); *Streptococcus dysgalactiae* acyl-ACP thioesterase (GenBank BAH81730); *Lactobacillus brevis* acyl-ACP thioesterase (GenBank ABJ63754); *Lactobacillus plantarum* acyl-ACP thioesterase (GenBank CAD6331G); *Anaerococcus tetradius* acyl-ACP thioesterase (GenBank EEI82564); *Bdellovibrio bacteriovorus* acyl-ACP thioesterase (GenBank CAE80300); *Clostridium thermocellum* acyl-ACP thioesterase (GenBank ABN54268); *Nannochloropsis oculata* acyl-ACP thioesterase (SEQ ID NO: 48, the nucleotide sequence of the gene encoding this thioesterase: SEQ ID NO: 49); *Nannochloropsis gaditana* acyl-ACP thioesterase (SEQ ID NO: 52, the nucleotide sequence of the gene encoding this thioesterase: SEQ ID NO: 53); *Nannochloropsis granulata* acyl-ACP thioesterase (SEQ ID NO: 54, the nucleotide sequence of the gene encoding this thioesterase: SEQ ID NO: 55); and *Symbiodinium microadriaticum* acyl-ACP thioesterase (SEQ ID NO: 56, the nucleotide sequence of the gene encoding this thioesterase; SEQ ID NO: 57).

Moreover, as the proteins functionally equivalent to the known acyl-ACP thioesterases, a protein consisting of an amino acid sequence having 50% or more (preferably 70% or more, more preferably 80% or more, and further preferably 90% or more) identity with the amino acid sequence of any one of the above-described acyl-ACP thioesterases, and having acyl-ACP thioesterase activity, can be also used.

Among the above-described acyt-ACP thioesterases, medium chain-specific acyl-ACP thioesterase is preferable. In particular, *Umbellularia californica* acyl-ACP thioesterase (SEQ ID NO: 50, the nucleotide sequence of the gene encoding this thioesterase: SEQ ID NO: 51), *Cocos nucifera* acyl-ACP thioesterase (SEQ ID NO: 46, the nucleotide sequence of the gene encoding this thioesterase: SEQ ID NO: 47), *Nannochloropsis oculata* acyl-ACP thioesterase (SEQ ID NO: 48, the nucleotide sequence of the gene encoding this thioesterase: SEQ ID NO: 49), *Nannochloropsis gaditana* acyl-ACP thioesterase (SEQ ID NO: 52, the nucleotide sequence of the gene encoding this thioesterase: SEQ ID NO: 53), *Nannochloropsis granulata* acyl-ACP thioesterase (SEQ ID NO: 54, the nucleotide sequence of the gene encoding this thioesterase: SEQ ID NO: 55), and *Symbiodinium microadriaticum* acyl-ACP thioesterase (SEQ ID NO. 56, the nucleotide sequence of the gene encoding this thioesterase: SEQ ID NO: 57); and a protein consisting of an amino acid sequence having 50% or more (preferably 70% or more, more preferably 80% or more, and further preferably 90% or more) identity with the amino acid sequence of any one of these acyl-ACP thioesterases, and having medium chain-specific acyl-ACP thioesterase activity, are more preferable.

The amino acid sequence information of these acyl-ACP thioesterases, the nucleotide sequence information of the genes encoding them, and the like can be obtained from, for example, National Center for Biotechnology Information (NCBI) and the like.

The acyl-ACP thioesterase activity of the protein can be measured by, for example, introducing a fusion gene produced by linking the acyl-ACP thioesterase gene to the downstream of a promoter which functions in a host cell such as *Escherichia coli*, into a host cell which lacks a fatty acid degradation system, culturing the thus-obtained cell under the conditions suitable for the expression of the introduced acyl-ACP thioesterase gene, and analyzing any change caused thereby in the fatty acid composition of the cell or the cultured liquid by using a gas chromatographic analysis or the like.

Alternatively, the acyl-ACP thioesterase activity can be measured by introducing a fusion gene produced by linking the acyl-ACP thioesterase gene to the downstream of a promoter which functions in a host cell such as *Escherichia coli*, into a host cell, culturing the thus-obtained cell under the conditions suitable for the expression of the introduced acyl-ACP thioesterase gene, and subjecting a disruption liquid of the cell to a reaction which uses acyl-ACPs, as substrates, prepared according to the method of Yuan et al. (Yuan L, Voelker T A, Hawkins D J, "Modification of the substrate specificity of an acyl-acyl carrier protein thioesterase by protein engineering", Proc. Natl. Acad. Sci. U.S.A., 1995 Nov. 7; 92 (23), p. 10639-10643).

3. Transformant (Recombinant)

The transformant of the present invention can be obtained by introducing the above-described gene encoding the protein (a) or (b) into a host. In the transformant, in comparison with the host, the ability to produce the medium chain fatty acids, and the lipids containing as the components the medium chain fatty acids is significantly improved. The ability to produce fatty acids and a lipid of the host and the transformant can be measured by the method used in Examples described below.

The transformant of the present invention can be obtained by introducing the above-described gene encoding the protein (a) or (b) into a host according to an ordinary genetic engineering method. Specifically, the transformant of the present invention can be produced by preparing an expression vector capable of expressing the gene encoding the protein (a) or (b) described above in a host cell, introducing it into a host cell to transform the host cell.

A transformant having cointroduced gene encoding the acyl-ACP thioesterase, preferably, the medium chain-specific acyl-ACP thioesterase can also be prepared in a similar manner.

The host for the transformant is not particularly limited, and examples of the host include microorganisms, plants or animals. In the present invention, microorganisms include algae and microalgae. Among these, microorganisms or plants are preferable, and microorganisms are more preferable, from the viewpoints of production efficiency and usability of the obtained lipids.

As the microorganisms for the host cell, prokaryotes and eukaryotes can be used. Prokaryotes include microorganisms belonging to the genus *Escherichia* or microorganisms belonging to the genus *Bacillus*. Eukaryotes include eukaryotic microorganisms belonging to yeast or filamentous fungi. Among these, from the viewpoint of the productivity of lipids, *Escherichia coli* belonging to the genus *Escherichia*, *Bacillus subtilis* belonging to the genus *Bacillus*, *Rhodosporidium toruloides* belonging to yeast, and *Mortierella* sp. belonging to filamentous fungi are preferable; and *Escherichia coli* is more preferable.

As the microorganisms for the host cell, microalgae are also preferable. As the microalgae, from a viewpoint of establishment of a gene recombination technique, algae belonging to the genus *Chlamydomonas*, algae belonging to the genus *Chlorella*, algae belonging to the genus *Phaeodactylum*, and algae belonging to the genus *Nannochloropsis* are preferable; and algae belonging to the genus *Nannochloropsis* are more preferable. Specific examples of the algae belonging to the genus *Nannochloropsis* include *Nannochloropsis oculata*, *Nannochloropsis gaditana*, *Nannochloropsis salina*, *Nannochloropsis oceanica*, *Nannochloropsis atomus*, *Nannochloropsis maculata*, *Nannochloropsis granulata*, and *Nannochloropsis* sp. Among these, from the viewpoint of the productivity of lipids, *Nannochloropsis oculata* or *Nannochloropsis gaditana* is preferable, and *Nannochloropsis oculata* is more preferable.

As the plants for the host cell, from the viewpoint of a high lipid content of seeds, *Arabidopsis thaliana*, rapeseed, *Cocos nucifera*, palm, cuphea, and *Jatropha curcas* are preferable, and *Arabidopsis thaliana* is more preferable.

A vector for use as the expression vector may be any vector capable of introducing the gene encoding the protein (a) or (b) into a host cell, and expressing the gene in the host cell. For example, a vector which has expression regulation regions such as a promoter and a terminator in accordance with the type of the host cell to be used, and has a replication initiation point, a selection marker or the like, can be used. Furthermore, the vector may also be a vector such as a plasmid capable of self-proliferation and self-replication outside the chromosome, or may also be a vector which is incorporated into the chromosome.

Specific examples of the vector include, in the case of using a microorganism as the host cell, pBluescript II SK(-) (manufactured by Stratagene), a pSTV-based vector (manufactured by Takara Bio), pUC-based vector (manufactured by Takara Shuzo), a pET-based vector (manufactured by Takara Bio), a pGEX-based vector (manufactured by GE Healthcare), a pCold-based vector (manufactured by Takara Bio), pHY300PLK (manufactured by Takara Bio), pUB110 (Mckenzie, T. et al., (1986), Plasmid 15(2); p. 93-103), pBR322 (manufactured by Takara Bio), pRS403 (manufactured by Stratagene), and pMW218/219 (manufactured by Nippon Gene). In particular, in the case of using *Escherichia coli* as the host cell, pBluescript II SK(-) or pMW218/219 is preferably used.

When the algae are used as the host cell, specific examples of the vector include P66 (Chlamydomonas Center), P-322 (Chlamydomonas Center), pPha-T1 (see Yangmin Gong, Xiaojing Guo, Xia Wan, Zhuo Liang, Mulan Jiang, "Characterization of a novel thioesterase (PtTE) from *Phaeodactylum tricornutum*". Journal of Basic Microbiology, 2011 December, Volume 51, p. 666-672) and pJET1 (manufactured by COSMO BIO). In particular, in the case of using the algae belonging to the genus *Nannochloropsis* as the host cell, pPha-T1 or pJET1 is preferably used. Moreover, when the host cell is the algae belonging to the genus *Nannochloropsis*, the host cell can be transformed, with referring to the method described in Oliver Kilian, et al., Proceedings of the National Academy of Sciences of the United States of America, December 27; 108(52), 2011, by using the DNA fragment consisting of the gene of the present invention, a promoter and a terminator. Specific examples of this DNA fragment include a PCR-amplified DNA fragment and a restriction enzyme-cut DNA fragment.

In the case of using a plant cell as the host cell, examples of the vector include a pRI-based vector (manufactured by Takara Bio), a pBI-based vector (manufactured by Clontech), and an IN3-based vector (manufactured by Inplanta Innovations). In particular, in the case of using *Arabidopsis thaliana* as the host cell, a pRI-based vector or a pBI-based vector is preferably used.

The kinds of the expression regulation regions such as a promoter and a terminator, and the selection marker are not particularly limited, and can be appropriately selected from ordinarily used promoters, markers and the like in accordance with the type of the host cell to be used.

Specific examples of the promoter include lac promoter, trp promoter, tac promoter, trc promoter, T7 promoter, SpoVG promoter, cauliflower mosaic virus 35S RNA promoter, promoters for housekeeping genes (e.g., tubulin promoter, actin promoter and ubiquitin promoter), rapeseed-derived *Napin* gene promoter, plant-derived Rubisco promoter, and a promoter of a violaxanthin/(chlorophyll a)-binding protein gene derived from the genus *Nannochloropsis*.

Examples of the selection marker include drug resistance genes such as antibiotic resistance genes (e.g. an ampicillin resistance gene, a chloramphenicol resistance gene, an erythromycin resistance gene, a neomycin resistance gene, a kanamycin resistance gene, a spectinomycin resistance gene, a tetracycline resistance gene, a blasticidin S resistance gene, a bialaphos resistance gene, a zeocin resistance gene, a paromomycin resistance gene, and a hygromycin resistance gene). Further, it is also possible to use a deletion of an auxotrophy-related gene or the like as the selection marker gene.

The expression vector or transformation can be constructed by introducing the gene encoding the protein (a) or (b) into the above-described vector according to an ordinary technique such as restriction enzyme treatment and ligation.

The method for transformation is not particularly limited as long as it is a method capable of introducing a target gene into a host cell. For example, a method of using calcium ion, a general competent cell transformation method (J. Bacterial. 93, 1925 (1967)), a protoplast transformation method (Mol. Gen. Genet 168, 111 (1979)), an electroporation method (FEMS Microbiol. Lett. 55, 135 (1990)), and an LP transformation method (T. Akamatsu and J. Sekiguchi, Archives of Microbiology, 1987, 146, p. 353-357; T. Akamatsu and H. Taguchi. Bioscience, Biotechnology, and Biochemistry, 2001, 65, 4, p. 823-829) and the like, can be used. When the host is the algae belonging to the genus *Nannochloropsis*, transformation can also be performed by applying the electroporation method described in Randor Radakovits, et al., Nature Communications, DOI: 10.1038/ncomms1688, 2012.

The selection of a transformant having a target gene fragment introduced therein can be carried out by using the selection marker or the like. For example, the selection can be carried out by using an indicator whether a transformant acquires the drug resistance as a result of introducing a vector-derived drug resistance gene into a host cell together with a target DNA fragment. Further, the introduction of a target DNA fragment can also be confirmed by PCR using a genome as a template.

4. Method of Producing Lipid

Then, the obtained transformant is used to produce a lipid.

The production method of the present invention contains collecting a lipid from the resulting transformant having the introduced gene encoding the protein (a) or (b). From the viewpoint of improvement in the productivity of lipids, the process preferably includes a step of obtaining a cultured product or grown product by culturing or growing, under suitable conditions, the transformant having the introduced gene encoding the protein (a) or (b); and a step of collecting the lipid from the resulting cultured product or grown product. Here, the cultured product means a cultured liquid and a transformant after being cultured, and the grown product means a transformant after being grown.

The medium and culture condition can be selected in accordance with the type of the host cell for transformation, and any ordinary used medium and condition can be employed.

In order to improve the productivity of medium chain fatty acids, the medium preferably contains the cerulenin. As mentioned above, KAS I and KAS II that catalyze the synthesis of acyl-ACP having 16 or 18 carbon atoms are inhibited by the cerulenin. On the other hand, KAS IV that catalyzes the synthesis of the medium chain acyl-ACP is insensitive to the cerulenin. The synthesis of acyl-ACP having 16 or 18 carbon atoms can be decreased, and the synthesis of the medium chain acyl-ACP can be increased by culturing or growing the transformant in a cerulenin-containing medium. A cerulenin concentration in the medium is preferably at a concentration at which growth is not adversely affected. Specifically, the cerulenin concentration is preferably 1 µM or more, and more preferably 10 µM or more. The upper limit is preferably 50 µM or less, and more preferably 25 µM or less. The cerulenin concentration is preferably from 1 to 50 µM, more preferably 10 to 50 µM, and further preferably 10 to 25 µM.

Further, from the viewpoint of the production efficiency of lipids, precursor substances participating in the fatty acid biosynthesis, such as glycerol, acetic acid or malonic acid, may be added to the medium.

For instance, in the case of using *Escherichia coli* as the host cell for transformation, culture may be carried out in LB medium or Overnight Express Instant TB Medium (manufactured by Novagen) at 30° C. to 37° C. for half a day to 1 day. In the case of using *Arabidopsis thaliana* as the host cell for transformation, growth may be earned out at soil under the temperature conditions of 20° C. to 25° C. by continuously irradiating white fight or under white tight illumination conditions of a light period of 16 hours and a dark period of 8 hours, for one to two months.

When the host cell of the transformation is the algae, the following culture media and culture conditions can be applied.

As the culture medium, medium based on natural seawater or artificial seawater may be used. Alternatively, commercially available culture medium may also be used. Specific examples of the culture medium include f/2 medium, ESM medium, Daigo IMK medium, L1 medium and MNK medium. Above all, from viewpoints of an improvement in the productivity of lipids and a nutritional ingredient concentration, f/2 medium. ESM medium or Daigo IMK medium is preferred; f/2 medium or Daigo IMK medium is more preferred; and f/2 medium is further preferred. For growth promotion of the algae and an improvement in productivity of medium fatty acids, a nitrogen source, a phosphorus source, a metal salt, vitamins, a trace metal or the like can be appropriately added to the culture medium.

An amount of the algae to be seeded to the culture medium is not particularly limited. In view of viability, the amount per culture medium is preferably 1% (vol/vol) or more, and 50% (vol/vol) or less, more preferably 10% (vol/vol) or less. Alternatively, the amount is preferably 1% to 50% (vol/vol), and more preferably 1% to 10% (vol/vol), per culture medium. Culture temperature is not particularly limited within the range in which the temperature does not adversely affect growth of the algae, but is ordinarily in the range of 5° C. to 40° C. From viewpoints of the growth promotion of the algae, the improvement in productivity of medium chain fatty acids, and reduction of production cost, the temperature is preferably 10° C. or more, more preferably 15° C. or more. The temperature is preferably 35° C. or less, more preferably 30° C. or less. Alternatively, the temperature is preferably 10° C. to 35° C. and more preferably 15° C. to 30° C.

Moreover, the algae are preferably cultured under irradiation with light so that photosynthesis can be made. The light irradiation only needs to be made under conditions in which the photosynthesis can be made, and artificial light or sunlight may be applied. From viewpoints of the growth promotion of the algae and the improvement in the productivity of medium chain fatty acids, irradiance during the light irradiation is preferably 100 lx or more, more preferably 300 lx or more, and further preferably 1,000 lx or more. The irradiance is preferably 50,000 lx or less, more preferably 10,000 lx or less, and further preferably 6,000 lx or less. Alternatively, irradiance during the light irradiation is preferably in the range of 100 lx to 50,000 lx, more preferably in the range of 300 to 10,000 lx, and further preferably 1,000 ix to 6,000 lx. Moreover, an interval of the light irradiation is not particularly limited. From the viewpoints in a manner similar to the viewpoints described above, the irradiation is preferably performed under a light and dark cycle. In 24 hours, a light period is preferably 8 hours or more, more preferably 10 hours or more, and preferably 24 hours or less, more preferably 18 hours or less. Alternatively, in 24 hours, a light period is preferably from 8 of 24 hours, further preferably from 10 to 18 hours, and still further preferably 12 hours.

Moreover, the algae are preferably cultured in the presence of a carbon dioxide-containing gas or in a culture medium containing carbonate such as sodium hydrogen carbonate so that the photosynthesis can be made. A concentration of carbon dioxide in the gas is not particularly limited. From the viewpoints of the growth promotion or the improvement in the productivity of medium chain fatty acids, the concentration is preferably 0.03% (which is the same degree as the concentration under atmospheric conditions) or more, more preferably 0.05% or more, further preferably 0.1% or more, and furthermore preferably 0.3% or more. The concentration is preferably 10% or less, more preferably 5% or less, further preferably 3% or less, and furthermore preferably 1% or less. Alternatively, the concentration is preferably from 0.03% to 10%, more preferably from 0.05% to 5%, further preferably from 0.1% to 3%, and still further preferably from 0.3% to 1%. A concentration of the carbonate is not particularly limited. When the sodium hydrogen carbonate is used, for example, from the viewpoints of the growth promotion and the improvement in the productivity of medium chain fatty acids, the concentration is preferably 0.01% by mass or more, more preferably 0.05% by mass or more, and further preferably 0.1% by mass or more. The concentration is preferably 5% by mass or less, more preferably 2% by mass or less, and further preferably 1% by mass or less. Alternatively, the concentration is preferably from 0.01 to 5% by mass, more preferably from 0.05 to 2% by mass, and further preferably from 0.1 to 1% by mass.

A culture time is not particularly limited, and the culture may be performed for a long time (for example, about 150 days) so that an alga body in which the lipid is accumulated at a high concentration can grow at a high concentration. From the viewpoints of the growth promotion of the algae, the improvement in the productivity of medium chain fatty acids, and the reduction of production cost, a culture time is preferably 3 days or more, more preferably 7 days or more. The time is preferably 90 days or less, more preferably 30 days or less. Alternatively, a culture time is preferably from 3 to 90 days, more preferably from 3 to 30 days, and further preferably from 7 to 30 days. In addition, the culture may be performed in any of aerated and agitated culture, shaking culture or static culture. From a viewpoint of improving air-permeability, shaking culture is preferred.

Lipids produced in the transformant is collected by an ordinary method used for isolating lipid components and the like contained in the living body of the transformant. For example, lipid components can be isolated and collected from the cultured product, the grown product or the transformant by means of filtration, centrifugation, cell disruption, gel filtration chromatography, ion exchange chromatography, chloroform/methanol extraction, hexane extraction, ethanol extraction, or the like. In the case of isolation and collection of larger scales, lipids can be obtained by collecting oil components from the cultured product, the grown product or the transformant through pressing or extraction, and then performing general purification processes such as degumming, deacidification, decoloration, dewaxing, and deodofization. After lipid components are isolated as such, the isolated lipids are hydrolyzed, and thereby fatty acids can be obtained. Specific examples of the method of isolating fatty acids from lipid components include a method of treating the lipid components at a high temperature of about 70° C. in an alkaline solution, a method of performing a lipase treatment and a method of degrading the lipid components using high-pressure hot water.

The lipids, particularly, the medium chain fatty acids and the lipids containing the above fatty acids as the components can be efficiently produced by applying the production method of the present invention.

The lipids produced in the production method of the present invention preferably contain one or more kinds selected from simple lipids and derived lipids, more preferably derived lipids, further preferably fatty acids or esters thereof, and still further preferably fatty acids or esters thereof, in view of usability thereof. The fatty acids contained in the lipids or esters thereof are preferably medium chain fatty acids or esters thereof, more preferably fatty acids having 12 to 14 carbon atoms or esters thereof, further preferably saturated fatty acids having 12 to 14 carbon atoms or esters thereof, still further preferably fatty acids having 12 carbon atoms or esters thereof, and particularly preferably lauric acid or an ester thereof, in view of usability to a surfactant or the like. Higher alcohol derivatives that are obtained by reducing these higher fatty acids can be used as surfactants.

The fatty acids and lipids obtained by the production method or the transformant of the present invention can be utilized for food, as well as an emulsifier incorporated into cosmetic products or the tike, a cleansing agent such as a soap or a detergent, a fiber treatment agent, a hair conditioning agent, a disinfectant or an antiseptic.

With regard to the embodiments described above, the present invention also discloses methods, transformants and proteins described below.

<1> A method of producing a lipid, containing the following steps (1) and (2):

(1) introducing a gene encoding the following protein (a) or (b) into a host, and thereby obtaining a transformant, and (2) collecting a lipid from the resulting transformant:

(a) A protein consisting of an amino acid sequence set forth in SEQ ID NO: 1; and (b) A protein consisting of an amino acid sequence having 60% or more identity with the amino acid sequence of the protein (a), and having β-ketoacyl-ACP synthase activity.

<2> The method of producing a lipid described in the above item <1>, wherein the protein (b) has the identity with the amino acid sequence of the protein (a) of 70% or more, preferably 80% or more, more preferably 90% or more, more preferably 91% or more, and more preferably 95% or more; and the protein (b) has the β-ketoacyl-ACP synthase activity.

<3> The method of producing a lipid described in the above item <1> or <2>, wherein the lipid is a medium fatty acid or an ester thereof.

<4> The method of producing a lipid described in any one of the above items <1> to <3>, wherein the protein is a β-ketoacyl-ACP synthase having the specificity to a medium chain acyl-ACP.

<5> The method of producing a lipid described in any one of the above items <1> to <4>, wherein a gene encoding an acyl-ACP thioesterase having the specificity to a medium chain acyl-ACP is also introduced into the host in the step (1).

<6> The method of producing a lipid described in any one of the above items <1> to <5>, wherein the step (2) includes a step of culturing the transformant in a cerulenin-containing medium.

<7> The method of producing a lipid described in any one of the above items <1> to <6>, wherein the host is a microorganism or a plant.

<8> The method of producing a lipid described in the above item <7>, wherein the microorganism is a microalga.

<9> The method of producing a lipid described in We above item <8>, wherein the microalga is an alga belonging to the genus *Nannochloropsis*.

<10> The method of producing a lipid described in the above item <7>, wherein the microorganism is *Escherichia coli*.

<11> A transformant, which is obtained by introducing a gene encoding the protein (a) or (b) into a host.

<12> The transformant described in the above item <11>, which is obtained by introducing the gene encoding the protein (a) or (b), and a gene encoding an acyl-ACP thioesterase having the specificity to a medium chain acyl-ACP into the host.

<13> The transformant described in the above item <11> or <12>, wherein the host is a microorganism or a plant.

<14> The transformant described in the above item <13>, wherein the microorganism is a microalga.

<15> The transformant described in the above item <14>, wherein the microalga is an alga belonging to the genus *Nannochloropsis*.

<16> The transformant described in the above item <13>, wherein the microorganism is *Escherichia coli*.
<17> A protein (a) or (c):
(a) A protein consisting of an amino acid sequence set forth in SEQ ID NO: 1; and
(c) A protein consisting of an amino acid sequence having 91% or more, preferably 95% or more, identity with the amino acid sequence of the protein (a), and having β-ketoacyl-ACP synthase activity.
<18> A gene encoding the protein described in the above item <17>.
<19> A gene consisting of a DNA (d) or (f):
(d) A DNA consisting of a nucleotide sequence set forth in SEQ ID NO: 2; and
(f) A DNA consisting of a nucleotide sequence having 78% or more, preferably 80% or more, more preferably 90% or more, further preferably 95% or more, identity with the nucleotide sequence of the DNA (d), and encoding a protein having β-ketoacyl-ACP synthase activity.
<20> A method of modifying a fatty acid composition in a lipid, containing introducing a gene encoding the protein (a) or (b) into a host.
<21> A method of enhancing productivity of a lipid, containing introducing a gene encoding the protein (a) or (b) into a host, and thereby obtaining a transformant.
<22> Use of the transformant described in any of the above items <11> to <16>, for producing a lipid.
<23> The use described in the above item <22>, wherein the lipid is a medium fatty acid or an ester thereof.

EXAMPLES

Hereinafter, the present invention will be described more in detail with reference to Examples, but the present invention is not limited thereto.

Example 1 Preparation of Transformant Prepared by Introducing β-Ketoacyl-ACP Synthase (KAS) Gene Derived from *Nannochloropsis Oculata* NIES-2145 (NoKASIV Gene) into *Escherichia coli*, and Production of Fatty Acids by the Transformant 1. Strain Having Introduced NoKASIV Gene
(1) Preparation of NoKASIV Gene, and Construction of Plasmid for NoKASIV Gene Expression
*Nannochloropsis Oculata* NIES-2145 was obtained from National Institute for Environmental Studies (NIES), and used. The *Nannochloropsis Oculata* NIES-2145 strains were sufficiently cultured in f/2 medium (75 mg of NaNO$_3$, 6 mg of NaH$_2$PO$_4$.2H$_2$O, 0.5 μg of vitamin B12, 0.5 μg of biotin, 100 μg of thiamine, 10 mg of Na$_2$SiO$_3$.9H$_2$O, 4.4 mg of Na$_2$EDTA.2H$_2$O, 3.16 mg of FeCl$_3$.6H$_2$O, 12 μg of FeCl$_3$.6H$_2$O, 21 μg of ZnSO$_4$.7H$_2$O, 180 μg of MnCl$_2$.4H$_2$O, 7 μg of CuSO$_4$.5H$_2$O, 7 μg of Na$_2$MoO$_4$.2H$_2$O/artificial sea water 1 L), inoculated by 10% in 50 mL of f/2 medium, and cultured at 25° C. and 0.3% of carbon dioxide for 6 days in an artificial climate chamber. After cultivation, the recover sample was crushed using Multi-beads shocker, and the RNA purification was carried out using RNeasy Plant Mini Kit (manufactured by Qiagen). A cDNA library was prepared from the obtained total RNA using SuperScript III First-Strand Synthesis System for RT-PCR (manufactured by invitrogen). This cDNA was used as a template, and PCR using a pair of primers set forth in SEQ ID NO: 3 and SEQ ID NO: 4 shown in Table 1 below was carried out to prepare a DNA fragment of the NoKASIV gene consisting of a nucleotide sequence set forth in SEQ ID NO: 2.

Moreover, using a plasmid vector pSTV28 (manufactured by TAKARA BIO) as a template, and a pair of primers set forth in SEQ ID NOS: 5 and 6 shown in Table 1. PCR was carried out to amplify the plasmid vector pSTV28. Then, the resultant was subjected to digestion by restriction enzyme DpnI (manufactured by TOYOBO Co., Ltd.) treatment. These two fragments were purified using High Pure PCR Product Purification Kit (manufactured by Roche Applied Science), and then fused using In-Fusion HD Cloning Kit (manufactured by Clontech) to construct a plasmid for NoKASIV gene expression.

| SEQ ID NO: | Nucleotide Sequence of Primers |
|---|---|
| SEQ ID NO: 3 | ATTCGAGCTCGGTACATGCGGGTCTCCAGTAGCGCC |
| SEQ ID NO: 4 | CAAGCTTGCATGCCTTTACTTGAACGGTTTGAAG |
| SEQ ID NO: 5 | GTACCGAGCTCGAATTCG |
| SEQ ID NO: 6 | AGGCATGCAAGCTTGGCACT |
| SEQ ID NO: 7 | GGAGAAAAAACTATAATGTCAGGAACATTCAATGA |
| SEQ ID NO: 8 | TTATAATACAGTTTTTTACCCAACTATCTTCAATT |
| SEQ ID NO: 9 | CGAGCTCGGTACCCGGGCGGTCTTTTGTCCTTTCCTC |
| SEQ ID NO: 10 | AATCTGCTCGGAGGGGAGGATC |
| SEQ ID NO: 11 | CCCTCCGAGCAGATTATGAAGACCGCCGCTCTCCTC |
| SEQ ID NO: 12 | GCGCGCAACACCGCGGGTGCGGGAGAAC |
| SEQ ID NO: 13 | GCTTCTGTGGAAGAGCCAGTG |
| SEQ ID NO: 14 | ACTCTAGAGGATCCCCTGATCTTGTCCATCTCGTG |
| SEQ ID NO: 15 | GGGATCCTCTAGAGTCGACCTGCAGGCATGCAAGC |
| SEQ ID NO: 16 | CGGGTACCGAGCTCGAATTC |
| SEQ ID NO: 17 | TCCGAGCAGATTATGATGGCCAAGCTGACCAGCGC |
| SEQ ID NO: 18 | CTCTTCCACAGAAGCTTAGTCCTGCTCCTCGGCCA |
| SEQ ID NO: 19 | AAATCATACAGCAGGATGCGGGTCTCCAGTAGCGC |
| SEQ ID NO: 20 | CTCTTCCACAGAAGCTTACTTGAACGGTTTGAAG |
| SEQ ID NO: 21 | CGAGCTCGGTACCCGGCTGCTGCCCCGACCGTATC |
| SEQ ID NO: 22 | CCTGCTGTATGATTTTGGCAC |
| SEQ ID NO: 23 | AAGAAGCTGTCTTTTATGGTCGAGATTCGAAGCAT |
| SEQ ID NO: 24 | CTCTTCCACAGAAGCTCAGAAGAACTCGTCCAACA |
| SEQ ID NO: 25 | CGAGCTCGGTACCCGACTGCGCATGGATTGACCGA |
| SEQ ID NO: 26 | ATATCAAGAAGCTGTCTTTT |
| SEQ ID NO: 27 | GGCGGTCTTTTGTCCTTTCCTCTATAG |
| SEQ ID NO: 28 | CTGATCTTGTCCATCTCGTGTGCCAC |
| SEQ ID NO: 29 | GCTGCTGCCCCGACCGTATC |
| SEQ ID NO: 30 | ACTGCGCATGGATTGACCGAC |
| SEQ ID NO: 31 | ACACAGGAAACAGCTATGGAGAAGCTATCCCTCGC |

-continued

| SEQ ID NO: | Nucleotide Sequence of Primers |
|---|---|
| SEQ ID NO: 32 | ACAAAATATTAACGCTTAAGGAACGTACTTCTTGA |
| SEQ ID NO: 33 | ATTCGAGCTCGGTACATGAAACGTGCAGTGATTAC |
| SEQ ID NO: 34 | CAAGCTTGCATGCCTTTAATCTTTCAGCTTGCGCA |
| SEQ ID NO: 35 | ATTCGAGCTCGGTACATGTCTAAGCGTCGTGTAGTTG |
| SEQ ID NO: 36 | CAAGCTTGCATGCCTTTAGATCTTTTTAAAGATCA |
| SEQ ID NO: 37 | ACACAGGAAACAGCTATGGCGGACTTGCCCCCGCTT |
| SEQ ID NO: 38 | ACAAAATATTAACGCCTAGGCAACATACTTCTTGA |

(2) Introduction of Plasmid for NoKASIV Gene Expression into *Escherichia Coli*

An *Escherichia coli* mutant strain, strain K27 (fadD88) (Overath et al, Eur. J. Biochem. 7, 559-574, 1969), was transformed by a competent cell transformation method, using the constructed plasmid for NoKASIV gene expression. The transformed strain K27 was stand overnight at 37° C., and a colony thus obtained was inoculated in 1 mL of LBCm liquid medium (Bacto Trypton 1%, Yeast Extract 0.5%, NaCl 1%, and chloramphenicol 30 μg/ml), and then cultured overnight at 30° C. The culture fluid of 20 μL was inoculated to 2 mL of Overnight Express Instant TB Medium (Novagen) and was subjected to shaking culture at 30° C. After 24 hours cultivation, lipid components contained in the culture fluid were analyzed by the method described below. As a negative control, *Escherichia coli* strain K27 transformed with the plasmid vector pSTV28 was also subjected to the same experiment.

(3) Extraction of Lipid and Analysis of Fatty Acids Contained Therein

To 1 mL of the culture fluid, 50 μL of 7-pentadecanone (1 mg/mL) as an internal standard was added, and then 0.5 mL of chloroform, 1 mL of methanol and 10 μL of 2N hydrochloric acid were further added. The mixture was vigorously stirred and then was left for 30 minutes. Further, 0.5 mL of chloroform and 0.5 mL of a 1.5% KCl were added thereto. The mixture was stirred and centrifuged for 15 minutes at 3,000 rpm, and then the chloroform layer (lower layer) was collected with pasteur pipette. A nitrogen gas was blown onto the resultant chloroform layer to be dried into solid, 0.7 mL of 0.5 N potassium hydroxide/methanol solution was added thereto, and the resultant mixture was kept warm at 80° C. for 30 minutes. Then, 1 mL of 14% solution of boron trifluoride (manufactured by Sigma-Aldrich) was added to the sample, and the mixture was kept warm at 80° C. for 10 minutes. Thereafter, 1 mL of saturated saline and 1 mL of hexane were added thereto, and the mixture was vigorously stirred and then was left for 30 minutes at room temperature. Then, the hexane layer (upper layer) was collected to obtain fatty acid esters.

The obtained fatty acid methyl esters were provided for gas chromatographic analysis. The gas chromatography analysis was carried out under the conditions as follows.
Capillary column: DB-1 MS 30 m×200 μm×0.25 μm (manufactured by J&W Scientific)
Mobile layer: high purity helium
Flow rate inside the column: 1.0 mL/min
Temperature rise program: 100° C. (for 1 min.)→10° C./min→300° C. (for 5 min.)
Equilibration time: for 1 min.
Injection port; split injection (split ratio: 100:1)
Pressure 14.49 psi, 104 mL/min
Amount of injection: 1 μL
Cleaning vial: methanol/chloroform
Detector temperature: 300° C.

Moreover, the fatty acid methyl esters were identified by providing the identical sample for a gas chromatography-mass spectrometry analysis under identical conditions described above.

Amounts of the fatty acid methyl esters were quantitatively determined based on the peak areas of waveform data obtained by the above gas chromatographic analysis. The peak area corresponding to each of the fatty acid methyl esters was compared with that of 7-pentadecanone as the internal standard, and carried out corrections between the samples, and then the amount of each of the fatty acids per liter of the culture fluid was calculated. Further, the total amount of the fatty acids was calculated by summing the amounts of each of the fatty acids thus obtained, and ratio (weight percent) of each of the fatty acids in the total amount of the fatty acids was calculated.

FIG. 1 shows a proportion of each amount of the fatty acids in the total amount of the fatty acids (amount of lipids) in the strain having the introduced NoKASIV gene and the strain having the introduced plasmid vector pSTV28 (negative control). Herein, in following drawings, the description of "Cx" for the fatty acid composition represents a fatty acid having "x" as the number of carbon atoms; and the description of "Cx:y" for the fatty acid composition represents a fatty acid having V as the number of carbon atoms, and "y" as the number of double bonds. In addition, in the following drawings, "n" represents an integer of 0 to 5. For example, when "C18:n" was described, the description represents a total of C18:0, C18:1, C18:2, C18:3, C18:4 and C18:5 fatty acids. Moreover, when "C16:n" was described, the description represents a total of C16:0 and C16:1 fatty acids.

As shown in FIG. 1, in the strain having the introduced NoKASIV gene (FIG. 1: NoKASIV), a content of the C14:0 fatty acid was higher in comparison with the strain K27 having the introduced pSTV28 (FIG. 1; WT).

2. Strain having Introduced NoKASIV Gene and CTE Gene

A multiple transformant having introduced NoKASIV gene and acyl-ACP thioesterase (CTE) gene derived from *Cocos nucifera* into *Escherichia coli* strain K27 (fadD88) was prepared.

The *Escherichia coli* strain K27 having the introduce CTE gene was transformed by a competent cell transformation method, using the plasmid for NoKASIV gene expression constructed in the above item 1. The *Escherichia coli* strain K27 having the introduce CTE gene was produced in accordance with the method described in JP-A-2011-250781 ("JP-A" means unexamined published Japanese patent application). As the CTE gene, the gene cloned in the plasmid vector pMW219 (manufactured by NIPPON GENE CO., LTD.) was used. The amino acid sequence of the CTE is shown in SEQ ID NO: 46, and the nucleotide sequence of the CTE gene is shown in SEQ ID NO: 47.

The transformed strain K27 was stand overnight at 37° C., and a colony thus obtained was inoculated in 1 ml of LBCmKm liquid medium (Bacto Trypton 1%, Yeast Extract 0.5%, NaCl 1%, chloramphenicol 30 μg/mL, and kanamycin sulfate 50 μg/mL), and then cultured overnight at 30° C. The culture fluid of 20 μL was inoculated to 2 ml of Overnight Express Instant TB Medium and was subjected to shaking culture at 30° C. After 24 hours cultivation, lipid components contained in the culture fluid were analyzed in a manner similar to the method in the above item 1. As a negative control, the strain having the introduced CTE gene that was transformed with the plasmid vector pSTV28, was also subjected to the same experiment.

The results are shown in FIG. 2.

As shown in FIG. 2, in the strain having the introduced NoKASIV gene and CTE gene (FIG. 2: CTE+NoKASIV), a content of each of the C12:0 and C14:0 fatty acids was higher in comparison with the strain K27 having the introduced CTE gene (FIG. 2: CTE).

3. Strain Having Introduced NoKASIV Gene and NoTE Gene

A multiple transformant having introduced NoKASIV gene and acyl-ACP thioesterase (NoTE) gene derived from *Nannochloropsis oculata* NIES-2145 into *Escherichia coli* strain K27 (fadD88) was prepared.

(1) Preparation of NoTE Gene, and Construction of Plasmid for NoTE Gene Expression Total RNA of *Nannochloropsis oculata* NIES 2145 was extracted, and reverse transcription was performed using Superscript III First-Strand Synthesis SuperMix for qRT-PCR (manufactured by Invitrogen) to obtain cDNA. Using this cDNA as a template, and a pair of primers set forth in SEQ ID NO: 66 and SEQ ID NO: 67 shown in Table 2 below, a gene fragment consisting of a nucleotide sequence set forth in SEQ ID NO: 49 was prepared by PCR. Moreover, using a plasmid vector pBluescriptII SK(−) (manufactured by Stratagene. Inc.) as a template, and a pair of primers set forth in SEQ ID NOS: 68 and 69 shown in Table 2 below, the pBluescriptII SK(−) was amplified by PCR. Then, the resultant was subjected to digestion by restriction enzyme DpnI (manufactured by TOYOBO Co., Ltd.) treatment. These two fragments were purified using High Pure PCR Product Purification Kit (manufactured by Roche Applied Science), and then fused using Irv-Fusion HD Cloning Kit (manufactured by Clontech) to construct a plasmid NoTE_1 for NoTE gene expression. This expression plasmid was constructed in the form of fusing on a side of an N-terminus of $1^{st}$ amino acid of an amino acid sequence (SEQ ID NO: 48) encoded by the NoTE gene with the amino acid sequence of the $1^{st}$ to $29^{th}$ amino acids on the side of the N-terminus of the LacZ protein derived from the plasmid.

TABLE 2

| SEQ ID NO: | Nucleotide Sequence of Primers |
| --- | --- |
| SEQ ID NO: 66 | GCGGCCGCTCTAGAGATGACGCCTTTGGCCTTCAC |
| SEQ ID NO: 67 | TGCTTCTTTCATTAGCTAGCTAATATCAATTTTCTTTGG |
| SEQ ID NO: 68 | CTCTAGAGCGGCCGCCACCG |
| SEQ ID NO: 69 | GCGTTAATATTTTGTTAAAATTCG |

(2) Introduction of Plasmid for NoTE Gene Expression into *Escherichia Coli*

The *Escherichia coli* mutant strain K27 was transformed by a competent cell transformation method, using the plasmid NoTE_1 for NoTE gene expression constructed in the above. The transformed strain K27 was stand overnight at 37° C., and a colony thus obtained was inoculated in 1 mL of LBAmp liquid medium (Bacto Trypton 1%, Yeast Extract 0.5%, NaCl 1%, and Ampicillin sodium 50 μg/mL), and then cultured overnight at 37° C. The culture fluid of 20 mL was inoculated to 2 ml of Overnight Express Instant TB medium (Novagen) and was subjected to shaking culture at 30° C. Thus, the transformed strain K27 having the introduced NoTE gene was obtained.

(3) Introduction of NoKASIV Gene into Strain K27 Having Introduced NoTe Gene

The strain K27 having the introduced NoTE gene was transformed by a competent cell transformation method, using the plasmid for NoKASIV gene expression constructed in the item 1.

The transformed strain K27 was stand overnight at 37° C. and a colony thus obtained was inoculated in 1 mL of LBCmAmp liquid medium (Bacto Trypton 1%. Yeast Extract 0.5%, NaCl 1%, chloramphenicol 30 μg/mL, and ampicillin sodium 50 μg/ml), and then cultured overnight at 30° C. The culture fluid of 20 μL was inoculated to 2 mL of Overnight Express Instant TB Medium and was subjected to shaking culture at 30° C. After 24 hours cultivation, lipid components contained in the culture fluid were analyzed in a manner similar to the method in the above item 1. As a negative control, the strain K27 having the introduced NoTE gene that was transformed with the plasmid vector pSTV28, was also subjected to the same experiment.

The results are shown in FIG. 3.

As shown in FIG. 3, in the strain having the introduced NoKASIV gene and NoTE gene (FIG. 3: NTE+NoKASIV), a content of each of the C12:1, C12:0, C14:0 and C14:1 fatty acids was higher in comparison with the strain K27 having the introduced NoTE gene (FIG. 3: NTE).

4. Lipid Productivity of Strain Having Introduced NoKASIV Gene and NoTE Gene in Cerulenin-Containing Medium The transformed strain K27 having the introduced NoKASIV gene and NoTE gene constructed in the item 3, was inoculated in 1 mL of LBCmAmp liquid medium (Bacto Trypton 1%, Yeast Extract 0.5%. NaCl 1%, chloramphenicol 30 μg/mL, and ampicillin sodium 50 μg/mL), and then cultured overnight at 30° C. The culture fluid of 20 μL was inoculated to 2 mL of Overnight Express Instant TB Medium and was subjected to shaking culture at 30° C. At this time, cerulenin (Wako Pure Chemical Industries) was added to the Overnight Express Instant TB Medium to be 10 μM in a final concentration. After 24 hours cultivation, lipid components contained in the culture fluid were analyzed in a manner similar to the method in the above item 1. As a negative control, the strain having the introduced NoKASIV gene and NoTE gene was cultured in a similar manner also in a medium in which no cerulenin was added.

The results are shown in FIG. 4.

As shown in FIG. 4, in the strain having the introduced NoKASIV gene and NoTE gene cultured in the cerulenin-containing medium (FIG. 4: NTE+NoKASIV+Cer), while a content of each of the C12:0 and C14:0 fatty acids increased, a content of each of the C16 and C18 fatty acids decreased.

Example 2 Production of *Nannochloropsis Oculata* Transformant Prepared by Introducing NoKASIV Gene and Acyl-ACP Thioesterase Gene Derived from *Umbellularia californica* (BTE), and Production of Fatty Acids by the Transformant 1. Strain Having Introduced NoKASIV Gene and BTE Gene
(1) Construction of Plasmid for BTE Gene Expression in *Nannochloropsis*

The gene sequence encoding the BTE described in JP-T-7-501924 ("JP-T" means published Japanese translation of PCT application) (SEQ ID NO: 51) was artificially synthesized. Using the synthesized DNA fragment as a template, and a pair of primers set forth in SEQ ID NO: 7 and SEQ ID NO: 8 shown in Table 1. PGR was carried out to prepare a BTE gene fragment. This DNA fragment was constructed in the form of removing the region corresponding to the chloroplast transit signal (85 amino acids on a side of an N-terminus) of the BTE (SEQ ID NO: 50).

A VCP1 promoter sequence (SEQ ID NO: 39), a VCP1 chloroplast transit signal sequence (SEQ ID NO: 40) and a VCP1 terminator sequence (SEQ ID NO: 41) were artificially synthesized based on the complete cds sequence (Accession number: JF957601.1) of the VCP1 (violaxanthin/(chlorophyll a)-binding protein) gene of *Nannochloropsis* sp. strain W2J3B registered in GenBank. Using each of the thus-synthesized DNA fragments as a template, and a pair of primers set forth in SEQ ID NOS: 9 and 10, a pair of primers set forth in SEQ ID NOS: 11 and 12, and a pair of primers set forth in SEQ ID NOS: 13 and 14 as shown in Table 1 below, PCR was carried out to prepare the VCP1 promoter sequence, the VCP1 chloroplast transit signal sequence and the VCP1 terminator sequence, respectively. Moreover, using a plasmid vector pUC19 (manufactured by TAKARA BIO) as a template, and a pair of primers set forth in SEQ ID NOS: 15 and 16 shown in Table 1, PCR was carried out to amplify the plasmid vector pUC19.

The BTE gene fragment, the VCP1 promoter sequence, the VCP1 chloroplast transit signal sequence and the VCP1 terminator sequence obtained as described above were fused with the plasmid vector pUC19 in a manner similar to the method in the item 1, in Example 1 to construct a plasmid pUC-vcp1c-BTE for BTE gene expression in *Nannochloropsis*. Herein, this plasmid consisted of the pUC19 vector sequence and an insert sequence in which the VCP1 promoter sequence, the VCP1 chloroplast transit signal sequence, the BTE gene fragment and the VCP1 terminator sequence were linked in this order.

A zeocin resistance gene (SEQ ID NO: 42) was artificially synthesized. Using the thus-synthesized DNA fragment as a template, and a pair of primers set forth in SEQ ID NOS: 17 and 18 shown in Table 1, PCR was carried out to prepare a zeocin resistance gene. The zeocin resistance gene fragment, the VCP1 promoter sequence and the VCP1 terminator sequence were fused in a manner similar to the method described above to construct a plasmid pUC-vcp1c-ble for zeocin resistance gene expression in *Nannochloropsis*.

2. Construction of Plasmid for NoKASIV Gene Expression in *Nannochloropsis*

Using the NoKASIV gene as a template, and a pair of primers set forth in SEQ ID NO: 19 and SEQ ID NO: 20 shown in Table 1, PCR was earned out, to prepare the NoKASIV gene fragment. Then, a ubiquitin promoter sequence (SEQ ID NO: 45) derived from *Nannochloropsis gaditana* CCMP 526 described in Randor Radakovits. et al., Nature Communications, DOI:10.1038/ncomms1688, 2012 was artificially synthesized. Using the thus-synthesized DNA fragment as a template, and a pair of primers set forth in SEQ ID NO: 21 and SEQ ID NO: 22 shown in Table 1, PCR was carried out to prepare a DNA fragment of the ubiquitin promoter. These amplified fragments were fused with the VCP1 terminator sequence and the amplified fragment of the plasmid vector pUC19 prepared in the above in a manner similar to the method described above to construct a plasmid pUC-UEPp-NoKASIV for NoKASIV gene expression in *Nannochloropsis*.

A paromomycin resistance gene (SEQ ID NO: 43), and a tubulin promoter sequence (SEQ ID NO: 44) derived from *Nannochloropsis gaditana* CCMP 526 described in Randor Radakovits, et al., Nature Communications, DOI:10.1038/ncomms1688, 2012 were artificially synthesized. Using the thus-synthesized DNA fragments as a template, and a pair of primers set forth in SEQ ID NO: 23 and SEQ ID NO: 24, and a pair of primers set forth in SEQ ID NO: 25 and SEQ ID NO: 26 shown in Table 1. PCR was carried out, to prepare the paromomycin resistance gene and the tubulin promoter sequence, respectively. These amplified fragments were fused with the VCP1 terminator sequence and the amplified fragment of the plasmid vector pUC19 prepared in the above in a manner similar to the method described above to construct a plasmid pUC-TUBp-aphVIII for paromomycin resistance gene expression in *Nannochloropsis*.

3. Introduction of Fragment for BTE Gene Expression into *Nannochloropsis*

Using the plasmid pUC-vcp1c-BTE for BTE gene expression as a template, and a pair of primers set forth in SEQ ID NOS: 27 and 28 shown in Table 1. PCR was carried out to amplify a fragment for BTE gene expression in the plasmid composed of the VCP1 promoter sequence, the VCP1 chloroplast transit signal sequence, the BTE gene fragment and the VCP1 terminator sequence. Moreover, using the plasmid pUC-vcp1c-ble for zeocin resistance gene expression as a template, and a pair of primers set forth in SEQ ID NOS: 27 and 28 shown in Table 1, PCR was earned out to amplify a fragment for zeocin resistance gene expression. Both of the amplified fragments were purified using High Pure PCR Product Purification Kit (manufactured by Roche Applied Science). Herein, sterilized water was used for elution upon purification without using an elution buffer included in the kit.

About $10^9$ cells of *Nannochloropsis oculata* strain NIES2145 were washed with 384 mM sorbitol solution to completely remove a salt, and the resultant was used as a host cell of transformation. The amplified fragment for BTE gene expression and fragment for zeocin resistance gene expression as amplified above were mixed by about 500 ng for each with the host cell, and electroporation was carried out under conditions of 50 μF, 500 Ω and 2,200 v/2 mm. After 24 hours recovery cultivation in f/2 liquid medium (75 mg of $NaNO_3$, 6 mg of $NaH_2PO_4.2H_2O$, 0.5 μg of vitamin B12, 0.5 μg of biotin, 100 μg of thiamine, 10 mg of $Na_2SiO_3.9H_2O$, 4.4 mg of $Na_2EDTA.2H_2O$, 3.16 mg of $FeCl_3.6H_2O$, 12 μg of $FeCl_3.6H_2O$, 21 μg of $ZnSO_4.7H_2O$, 180 μg of $MnCl_2.4H_2O$, 7 μg of $CuSO_4.5H_2O$, 7 μg of $Na_2MoO_4.2H_2O$/artificial sea water 1 L), the resultant material was inoculated in f/2 agar medium containing 2 μg/mL of zeocin (prepared by adding 0.8% agar to the f/2 liquid medium), and cultured for two to three weeks under 12 h/12 h light-dark conditions at 25° C. under an atmosphere of 0.3% $CO_2$. A transformant containing the fragment for BTE gene expression was selected from the resultant colonies by a PGR method.

4. Introduction of Plasmid for NoKASIV Gene Expression into *Nannochloropsis*

Using the plasmid pUC-UEPp-NoKASIV for NoKASIV gene expression as a template, and a pair of primers set forth in SEQ ID NO: 29 and SEQ ID NO: 28 shown in Table 1, PCR was carried out to amplify a fragment for NoKASIV gene expression composed of the promoter sequence, the NoKASIV gene and the VCP1 terminator sequence contained in the plasmid. Further, using the plasmid pUC-TUBp-aphVIII as a template, and a pair of primers set forth in SEQ ID NOS: 30 and 28 shown in Table 1, PCR was carried out to amplify a fragment for paromomycin resistance gene expression. Both of the amplified fragments were introduced in the similar manner described above into the strain having the introduced BTE prepared in the item 3, and cultured. From among the resultant colonies, a strain containing the fragment for NoKASIV gene expression was selected by the PCR method.

5. Lipid Productivity of BTE Gene and NoKASIV Gene Expression Strain

The strain selected in the above item 4, was inoculated to 50 mL of culture medium in which a nitrogen concentration in the f/2 medium was reinforced 15 times, and a phosphorus concentration therein was reinforced 5 times (hereinafter, referred to as "N15P5 medium"), and subjected to shaking culture for four weeks under the 12 h/12 h light-dark conditions at 25° C. under the atmosphere of 0.3% $CO_2$, to prepare preculture fluid. Then, 10 mL of the preculture fluid was inoculated to 40 ml of the N15P5 medium, and subjected to shaking culture under the 12 h/12 h light-dark conditions at 25° C. under the atmosphere of 0.3% $CO_2$. After 3 weeks cultivation, lipid components contained in the culture fluid were analyzed in a manner similar to the method in Example 1. As a negative control, the *Nannochloropsis* strain having only the introduced BTE gene was also subjected to the same experiment.

The results are shown in FIG. 5.

As shown in FIG. 5, in the strain having the introduced NoKASIV gene and BTE gene (FIG. 5: BTE+NoKASIV), a content of each of the C12:0 and C14:0 fatty acids was higher in comparison with the strain having the introduced BTE gene (FIG. 5: BTE).

6. Lipid Productivity of Strain Having Introduced BTE Gene and NoKASIV Gene in Cerulenin-Containing Medium The strain selected in the item 4, was precultured in a manner similar to the method in the item 5, inoculated to the N15P5 medium containing 10 μM of cerulenin, and subjected to shaking culture under the 12 h/12 h light-dark conditions at 25° C. under the atmosphere of 0.3% $CO_2$. After 3 weeks cultivation, lipid components contained in the culture fluid were analyzed in a manner similar to the method in Example 1. As a negative control, a system in which no cerulenin was added was also subjected to the same experiment.

The results are shown in FIG. 6.

As shown in FIG. 6, in the strain having the introduced NoKASIV gene and BTE gene cultured in the cerulenin-containing medium (FIG. 6: BTE+NoKASIV+Cer), while a content of each of the C12:0 and C14:0 fatty acids increased, a content of each of the C16 and C18 fatty acids decreased.

Example 3 Preparation of Transformant Prepared by Introducing β-Ketoacyl-ACP Synthase Gene Derived from *Nannochloropsis Gaditana* CCMP526 (NgKASIV Gene) into *Escherichia Coli*, and Production of Fatty Acids by the Transformant 1. Strain Having Introduced NgKASIV Gene
(1) Preparation of NgKASIV Gene, and Construction of Plasmid for NgKASIV Gene Expression Information on the sequences of a total of 9052 genes of *Nannochloropsis gaditana* CCMP 526 was acquired from the *Nannochloropsis* Genome Project (nannochloropsis.genomeprojectsolutions-databases.com) provided by Colorado School of Mines and Genome Project Solutions. A Nga04201 gene (a gene consisting of the nucleotide sequence set forth in SEQ ID NO: 59; hereinafter, referred to as "NgKASIV") being one of the genes was obtained utilizing customer synthesis service of an artificial gene. Using the obtained artificial gene as a template, and a pair of primers set forth in SEQ ID NOS: 31 and 32 as shown in Table 1, a DNA fragment of the NgKASIV gene consisting of a nucleotide sequence set forth in SEQ ID NO: 59 was prepared by PCR. The NgKASIV gene set forth in SEQ ID NO: 59 has 77% identity with the gene sequence set forth in SEQ ID NO: 2. The amino acid sequence of the NgKASIV set forth in SEQ ID NO: 58 has 90% identity with the amino acid sequence set forth in SEQ ID NO: 1.

Moreover, using a plasmid vector pSTV28 (manufactured by TAKARA BIO) as a template, and a pair of primers set forth in SEQ ID NOS: 5 and 6 shown in Table 1, the pSTV28 was amplified by PGR. Then, the resultant was subjected to digestion by restriction enzyme DpnI (manufactured by TOYOBO Co., Ltd.) treatment. These two fragments were purified using High Pure PCR Product Purification Kit (manufactured by Roche Applied Science), and then fused using in-Fusion HD Cloning Kit (manufactured by Clontech) to construct a plasmid for NgKASIV gene expression.

(2) Introduction of Plasmid for NgKASIV Gene Expression into *Escherichia Coli*

The *Escherichia coli* strain K27 was transformed in a manner similar to the method in the item 1, in Example 1, using the constructed plasmid for NgKASIV gene expression, and the transformed strain was subjected to shaking culture at 30° C. After 24 hours cultivation, lipid components contained in the culture fluid were analyzed in a manner similar to the method in Example 1. As a negative control, the *Escherichia coli* strain K27 that was transformed with the plasmid vector pSTV28, was also subjected to the same experiment.

The results are shown in FIG. 7.

As shown in FIG. 7, in the strain having the introduced NgKASIV gene (FIG. 7: NgKASIV), a content of the C14:0 fatty acid was higher in comparison with the strain K27 having the introduced plasmid vector pSTV28 (FIG. 7: WT).

2. Strain Having Introduced NgKASIV Gene and CTE Gene

A multiple transformant having introduced NgKASIV gene and acyl-ACP thioesterase (CTE) gene derived from *Cocos nucifera* into *Escherichia coli* strain K27 (fadD88) was prepared.

The *Escherichia coli* strain K27 was transformed in a manner similar to the method in the item 2, in Example 1, using the plasmid for NgKASIV gene expression constructed in the above item 1, and the transformed strain was subjected to shaking culture at 30° C. After 24 hours cultivation, lipid components contained in the culture fluid were analyzed in a manner similar to the method in Example 1. As a negative control, the strain K27 having the introduced CTE gene that was transformed with the plasmid vector pSTV28, was also subjected to the same experiment.

The results are shown in FIG. 8.

As shown in FIG. 8, in the strain having the introduced NgKASIV gene and CTE gene (FIG. 8: CTE+NgKASIV), a content of each of the C12:0, C14.1 and C14:0 fatty acids was higher in comparison with the strain K27 having the introduced CTE gene (FIG. 8: CTE).

3. Strain Having Introduced NgKASIV Gene and NoTE Gene

A multiple transformant having introduced NgKASIV gene and acyl-ACP thioesterase (NoTE) gene derived from *Nannochloropsis oculata* NIES-2145 into *Escherichia coli* strain K27 (fadD88) was prepared.

The *Escherichia coli* strain K27 was transformed in a manner similar to the method in the item 3, in Example 1, using the plasmid for NgKASIV gene expression constructed in the above item 1, and the transformed strain was subjected to shaking culture at 30° C. After 24 hours cultivation, lipid components contained in the culture fluid were analyzed in a manner similar to the method in Example 1. As a negative control, the strain K27 having the introduced NoTE gene that was transformed with the plasmid vector pSTV28, was also subjected to the same experiment.

The results are shown in FIG. 9.

As shown in FIG. 9, in the strain having the introduced NgKASIV gene and NoTE gene (FIG. 9: NTE+NgKASIV), a content of each of the C12:1, C12:0. C14:1 and C14:0 fatty acids was higher in comparison with the strain having the introduced NoTE gene (FIG. 9; NTE).

Comparative Example 1 Production of *Escherichia Coli* Transformant Prepared by Introducing KAS I (EKASI) Gene or KAS II (EKASII) Gene Derived from *Escherichia coli* K27, and Production of Fatty Acids by the Transformant 1. Strain Having Introduced EKASI Gene or EKASII Gene
(1) Construction of Plasmid for EKASI Gene or EKASII Gene Expression The information of the nucleotide sequence of each of the EKASI gene and the EKASII gene derived from *Escherichia coli* was obtained from the database PEC (Profiling of *E. coli* Chromosome, shigen.nig.ac.jp/ecoli/pec). *Escherichia coli* strain K27 was subjected to shaking culture in an LB medium at 30° C., and then bacterial cells were collected from 1 mL of the cultured liquid, and DNA was obtained by using QIAamp DNA Mini Kit (manufactured by QIAGEN). Using this obtained DNA as a template, and a pair of primers set forth in SEQ ID NOS: 33 and 34 or a pair of primers set forth in SEQ ID NOS: 35 and 36 as shown in Table 1, PCR was carried out to prepare a DNA fragment of the EKASI gene set forth in SEQ ID NO: 63 and a DNA fragment of the EKASII gene set forth in SEQ ID NO: 65. The EKASI gene set forth in SEQ ID NO: 63 has 49% identity with the gene sequence set forth in SEQ ID NO: 2. The EKASII gene set forth in SEQ ID NO: 65 has 53% identity with the gene sequence set forth in SEQ ID NO: 2. The amino acid sequence of the EKASI set forth in SEQ ID NO: 62 has about 34% identity with the amino acid sequence set forth in SEQ ID NO: 1. The amino acid sequence of the EKASII set forth in SEQ ID NO: 64 has about 45% identity with the amino acid sequence set forth in SEQ ID NO: 1.

Moreover, using a plasmid vector pSTV28 (manufactured by TAKARA BIO) as a template, and a pair of primers set forth in SEQ ID NOS: 5 and 6 shown in Table 1, the pSTV28 was amplified by PCR. Then, the resultant was subjected to digestion by restriction enzyme DpnI (manufactured by TOYOBO Co., Ltd.) treatment. These two fragments were purified using High Pure PCR Product Purification Kit (manufactured by Roche Applied Science), and then fused using In-Fuston HD Cloning Kit (manufactured by Clontech) to construct a plasmid for EKASI gene expression and a plasmid for EKASII gene expression.

(2) Introduction of Plasmid for EKASI Gene Expression or EKASII Gene Expression into *Escherichia Coli*

The *Escherichia coli* strain K27 was transformed in a manner similar to the method in the item 1, in Example 1, using the constructed plasmid for EKASI gene expression or EKASII gene expression, and the transformed strains were subjected to shaking culture at 30° C. After 24 hours cultivation, lipid components contained in the culture fluid were analyzed in a manner similar to the method in Example 1 As a negative control, the *Escherichia coli* strain K27 that was transformed with the plasmid vector pSTV28, was also subjected to the same experiment.

The results are shown in FIG. 10.

As shown in FIG. 10, in the strain having the introduced EKASI gene (FIG. 10: EKASI), and the strain having the introduced EKASII gene (FIG. 10: EKASII), a content of the C14:0 fatty acid was lower than that of the strain having the introduced plasmid vector pSTV28 (FIG. 10: WT).

2. Strain Having Introduced EKASI Gene or EKASII Gene, and NoTE Gene

A multiple transformant having introduced EKASI gene or EKASII gene and acyl-ACP thioesterase (NoTE) gene derived from *Nannochloropsis oculata* NIES-2145 into *Escherichia coli* strain K27 (fadD88) was prepared.

The *Escherichia coli* strain K27 was transformed in a manner similar to the method in the item 3, in Example 1, using the plasmid for EKASI gene expression or EKASII gene expression constructed in the above item 1, and the transformed strains were subjected to shaking culture at 30° C. After 24 hours cultivation, lipid components contained in the culture fluid were analyzed in a manner similar to the method in Example 1. As a negative control, the strain K27 having the introduced NoTE gene that was transformed with the plasmid vector PSTV28, was also subjected to the same experiment.

The results are shown in FIG. 11.

As shown in FIG. 11, in the strain having the introduced EKASI gene and NoTE gene (FIG. 11: NTE+EKASI) and the strain having the introduced EKASII gene and NoTE gene (FIG. 11: NTE+EKASII), a content of each of the C12:1, C12:0, C14:1 and C14:0 fatty acids was lower than those of the strain having the introduced NoTE gene (FIG. 11: NTE).

Comparative Example 2 Production of *Escherichia coli* Transformant Prepared by Introducing Kas (NoKASIorII) Gene Derived from *Nannochlorosis Oculata* NIES-2145, and Production of Fatty Acids by the Transformant (1) Preparation of NoKASIorII Gene, and Construction of Plasmid for NoKASIorII Gene Expression A cDNA library of *Nannochloropsis oculata* NIES-2145 was prepared in a manner similar to the method in the item 1. in Example 1. Using this cDNA as a template, and a pair of primers set forth in SEQ ID NOS: 37 and 38 as shown in Table 1. PGR was carried out to prepare a DNA fragment of the NoKASIorII gene set forth in SEQ ID NO: 61. The NoKASIorII gene set forth in SEQ ID NO: 61 has 59% identity with the gene sequence set forth in SEQ ID NO: 2. The amino acid sequence of the NoKASIorII set forth in SEQ ID NO: 60 has 52% identity with the amino acid sequence set forth in SEQ ID NO: 1.

Moreover, the pSTV28 was amplified by PGR using a plasmid vector pSTV28 (manufactured by TAKARA BIO) as a template, and a pair of primers set forth in SEQ ID NOS: 5 and 6 shown in Table 1. Then, the resultant was subjected to digestion by restriction enzyme DpnI (manufactured by TOYOBO Co., Ltd.) treatment. These two fragments were purified using High Pure PCR Product Purification Kit (manufactured by Roche Applied Science), and then fused using In-Fusion HD Cloning Kit (manufactured by Clontech) to construct a plasmid for NoKASIorII gene expression.

(2) Introduction of Plasmid for NoKASIorII Gene Expression into *Escherichia Coli*

The *Escherichia Coli* strain K27 was transformed in a manner similar to the method in the item 1, in Example 1, using the constructed plasmid for NoKASIorII gene expression, and the transformed strain was subjected to shaking culture at 30° C. After 24 hours cultivation, lipid components contained in the culture fluid were analyzed in a manner similar to the method in Example 1. As a negative control, the *Escherichia Coli* strain K27 that was transformed with the plasmid vector pSTV28, was also subjected to the same experiment.

The results are shown in FIG. 12.

As shown in FIG. 12, in the strain having the introduced NoKASIorII gene (FIG. 12: NoKASIorII), a content of the C14:0 fatty acid was lower than that of the strain having the introduced plasmid vector pSTV28 (FIG. 12: WT).

2. Strain Having Introduced NoKASIorII Gene and CTE Gene

A multiple transformant having introduced NoKASIorII gene and acyl-ACP thioesterase (CTE) gene derived from *Cocos nucifera* into *Escherichia coli* strain K27 (fadD88) was prepared.

The *Escherichia coli* strain K27 was transformed in a manner similar to the method in the item 2, in Example 1, using the plasmid for NoKASIorII gene expression constructed in the item 1, and the transformed strain was subjected to shaking culture at 30° C. After 24 hours cultivation, lipid components contained in the culture fluid were analyzed in a manner similar to the method in Example 1. As a negative control, the strain K27 having the introduced CTE gene that was transformed with the plasmid vector pSTV28, was also subjected to the same experiment.

The results are shown in FIG. 13.

As shown in FIG. 13 in the strain having the introduced NoKASIorII gene and CTE gene (FIG. 13: CTE+NoKASIorII), a content of each of the C12:0, C14:1 and C14:0 fatty acids was lower than those of the strain having the introduced CTE gene (FIG. 13: CTE).

3. Strain Having Introduced NoKASIorII Gene and NoTE Gene

A multiple transformant having introduced NoKASIorII gene and acyl-ACP thioesterase (NoTE) gene derived from *Nannochloropsis oculata* NIES-2145 into *Escherichia coli* strain K27 (fadD88) was prepared.

The *Escherichia coli* strain K27 was transformed in a manner similar to the method in the item 3, in Example 1, using the plasmid for NoKASIorII gene expression constructed in the above item 1, and the transformed strain was subjected to shaking culture at 30° C. After 24 hours cultivation, lipid components contained in the culture fluid were analyzed in a manner similar to the method in Example 1. As a negative control, the strain K27 having the introduced NoTE gene that was transformed with the plasmid vector pSTV28, was also subjected to the same experiment.

The results are shown in FIG. 14.

As shown in FIG. 14, in the strain having the introduced NoKASIorII gene and NoTE gene (FIG. 14: NTE+NoKASIorII), a content of each of the C12:1, C12:0 and C14:1 fatty acids was lower than those of the strain having the introduced NoTE gene (FIG. 14: NTE).

Comparative Example 3 Production of *Nannochtoropsis Oculata* Transformant Prepared by Introducing KASIV (CIKASIV) Gene Derived from *Cuphea Ianceolata* and BTE Gene, and Production of Fatty Acids by the Transformant 1. Strain Having Introduced CIKASIV Gene and BTE Gene The gene sequence encoding CIKASIV (SEQ ID NO: 71; Accession number: AJ344250.1; Shutt B S et al., "Beta-ketoacyl-acyl carrier protein synthase IV: a key enzyme for regulation of medium-chain fatty acid synthesis in *Cuphea Ianceolata* seeds" Planta. 2002 September; 215 (5) p. 847-54) was artificially synthesized. The CIKASIV gene set forth in SEQ ID NO: 71 has 49% identity with the gene sequence set forth in SEQ ID NO. 2. The amino acid sequence of the CIKASIV set forth in SEQ ID NO: 70 has about 38.5% identity with the amino acid sequence set forth in SEQ ID NO: 1.

Using the synthesized DNA fragment as a template, and a pair of primers set forth in SEQ ID NO: 72 and SEQ ID NO: 73, PGR was carried out to prepare a CIKASIV gene fragment.

The thus-obtained CIKASIV gene fragment, and the VCP1 terminator sequence and the ubiquitin promoter sequence used in Example 2 were fused with the plasmid vector pUC19 in a manner similar to the method in the item 1, in Example 1, to construct a plasmid pUC-UEPp-CIKASIV for CIKASIV gene expression in *Nannochloropsis*.

TABLE 3

| SEQ ID NO: | Nucleotide Sequence of Primers |
|---|---|
| SEQ ID NO: 72 | aaatcatacagcaggatggcggcggcctcttccat |
| SEQ ID NO: 73 | ctcttccacagaagcctaattgtaaggggcgaaga |

2. Introduction of Fragment for CIKASIV Gene Expression into *Nannochloropsis*

Using the plasmid pUC-UEPp-CIKASIV for CIKASIV gene expression as a template, and a pair of primers set forth in SEQ ID NO. 29 and SEQ ID NO: 28 shown in Table 1, PCR was carried out to amplify a fragment for CIKASIV gene expression composed of the promoter sequence, the CIKASIV gene and the VCP1 terminator sequence contained in this plasmid. Further, using the plasmid pUC-TUBp-aphVIII described in the item 2, in Example 2 as a template, and a pair of primers set forth in SEQ ID NOS: 30 and 28 shown in Table 1, PCR was carried out to amplify a fragment for paromomycin resistance gene expression. In a manner similar to the method in the item 3, in Example 2, both of the amplified fragments were introduced into the strain having the introduced BTE prepared in the item 3, in Example 2, and cultured. From among the resultant colonies, a strain containing the fragment for CIKASIV gene expression was selected by the PCR method.

3. Lipid Productivity of BTE Gene and NoKASIV Gene Expression Strain

The strain selected in the above item 2, was inoculated to 50 mL of culture medium in which a nitrogen concentration in the f/2 medium was reinforced 15 times, and a phosphorus concentration therein was reinforced 5 times (hereinafter, referred to as "N15P5 medium"), and subjected to shaking culture for four weeks under the 12 h/12 h light-dark conditions at 25° C. under the atmosphere of 0.3% $CO_2$, to prepare preculture fluid. Then, 10 mL of the preculture fluid was inoculated to 40 mL of the N15P5 medium, and subjected to shaking culture under the 12 h/12 h light-dark conditions at 25° C. under the atmosphere of 0.3% $CO_2$. After 3 weeks cultivation, lipid components contained in the culture fluid were analyzed in a manner similar to the method in Example 1. As a negative control, the *Nannochloropsis* strain having only the introduced BTE gene obtained in the item 3, in Example 2 and the *Nannochloropsis* strain having the introduced BTE and NoKASIV genes obtained in the item 4. In Example 2 were also subjected to the same experiment.

The results are shown in FIG. 15.

As shown in FIG. 15, in the strain having the introduced CIKASIV gene and BTE gene (FIG. 15: BTE+CIKASIV), a content of each of the C12:0 and C14:0 fatty acids was lower than those of the strain having the introduced NoKASIV gene and BTE gene (FIG. 15: BTE+NoKASIV).

Example 4 Preparation of Transformant by Introducing NoKASIV Gene and CTE Gene into *Arabidopsis thaliana*, and Production of Fatty Acids by the Transformant 1. Construction of Plasmid for CTE Gene Introduction According to the techniques in Example 1 in JP-A-2011-250781, a plasmid p909CTE for plant introduction was constructed. The plasmid was designed in such a manner that the CTE gene was subjected to expression control by the Napin gene promoter derived from *Brassica rapa* and localized to the chloroplast by the chloroplast transit signal peptide derived from the BTE gene.

Napin gene promoter sequence derived from *Brassica rapa* is shown in SEQ ID NO: 74, the Napin gene terminator sequence derived from *Brassica rapa* is shown in SEQ ID NO: 75, and the sequence of the CTE gene linked with the chloroplast transit signal peptide derived from the BTE gene is shown in SEQ ID NO: 76. These sequences are contained in the above plasmid.

2. Construction of Plasmid for NoKASIV Gene Introduction

According to the following procedure, the kanamycin resistance gene originally held by the vector pRI909 for plant introduction (manufactured by TAKARA BIO) was substituted for the bialaphos resistance gene (Bar gene) derived from *Streptomyces hygroscopicus*. The Bar gene encodes a phosphinothricin acetyl transferase. The bialaphos resistance gene derived from the *Streptomyces hygroscopicus* (SEQ ID NO: 77) was obtained utilizing customer synthesis service provided by GenScript with reference to the sequence of the vector pYW310 for transformation disclosed in Gene Bank of NCBI (ACCESSION NO. DQ469641). The Bar gene was amplified by PCR using PrimeSTAR with the artificially synthesized gene as a template, and a pair of primers set forth in SEQ ID NO: 79 and SEQ ID NO: 80. Moreover, a pRI909 vector region excluding the kanamycin resistance gene was amplified by PCR using PrimeSTAR with the pRI909 as a template, and a pair of primers set forth in SEQ ID NO. 81 and SEQ ID NO: 82. Both of the amplified fragments were subjected to restriction enzyme digestion with NdeI and SpeI, and then linked by ligation reaction, to construct a plasmid pRI909 Bar.

A *Brassica napus* Napin promoter sequence (SEQ ID NO: 78) expressed in seeds of *Brassica napus* was obtained utilizing customer synthesis service provided by GenScript with reference to the *Brassica napus napin* Promoter sequence disclosed in Gene Bank of NCBI (ACCESSION NO. EU416279). The *Brassica napus* Napin promoter sequence was amplified by PCR using the artificially synthesized promoter sequence as a template, and a pair of primers set forth in SEQ ID NO: 83 and SEQ ID NO: 84. Moreover, a straight chain fragment of the pRI909 Bar was amplified by PCR using the plasmid pRI909 Bar as a template, and a pair of primers set forth in SEQ ID NO: 85 and SEQ ID NO: 86. Moreover, a CTE-Tnapin sequence was amplified by PCR using the plasmid p909CTE as a template, and a pair of primers set forth in SEQ ID NO: 87 and SEQ ID NO: 88. These amplified products were linked by In-fusion reaction in a manner similar to the method described above, to construct a plasmid p909Pnapus-CTE-Tnapin.

A straight chain fragment of the p909Pnapus-Tnapin excluding the CTE gene region was amplified by PCR using the plasmid p909Pnapus-CTE-Tnapin as a template, and a pair of primers set forth in SEQ ID NO: 89 and SEQ ID NO: 90. Moreover, the NoKASIV gene was amplified by PCR using the cDNA derived from *Cocos nucifera* L. endosperm as a template, and a pair of primers set forth in SEQ ID NO: 91 and SEQ ID NO: 92. The obtained amplified products were linked by In-fusion reaction in a manner similar to the method described above, to construct a plasmid p909Pnapus-NoKASIV-Tnapin.

TABLE 4

| SEQ ID NO: | Nucleotide Sequence of Primers |
|---|---|
| SEQ ID NO: 79 | atatatatactagtatgagcccagaacgacg |
| SEQ ID NO: 80 | atatatatcatatgatcagatctcggtgacggg ca |
| SEQ ID NO: 81 | tgacgagttccatatggcgggactctggggttcgaa |
| SEQ ID NO: 82 | catcttgttcactagtgcgaaacgatccagatccg gt |
| SEQ ID NO: 83 | taccgaggggaatttatggaacgtcagtggag |
| SEQ ID NO: 84 | actagtggatcctcgtgtatgtttttaatct |
| SEQ ID NO: 85 | actctgagattaacctatggctcccctttaaa |
| SEQ ID NO: 86 | gaattcgtaatcatggtcatagctgtttcct |
| SEQ ID NO: 87 | cgaggatccactagtatggccaccacctctttagc ttccgct |
| SEQ ID NO: 88 | catgattacgaattcaagctttatcggtaaaacaa cgagc |
| SEQ ID NO: 89 | actagtggatcctcgtgtatgtttttaatc |
| SEQ ID NO: 90 | ggcatatggtgtgtataccacggtgatatg |
| SEQ ID NO: 91 | cgaggatccactagtatgcgggtctccagtagcgc cgt |
| SEQ ID NO: 92 | tacacaccatatgccttacttgaacggtttgaaga tta |

3. Transformation of *Arabidopsis Thaliana*

The plasmid p909CTE for CTE gene introduction was supplied to the custom service for *Arabidopsis thaliana* transformation by Inplanta Innovations, and thus a transformant of *Arabidopsis thaliana* having the introduced CTE gene was obtained. The wild-type strain and the transformant of *Arabiposis thaliana* were grown at room temperature of 22° C., under the conditions of a light period of 24 hours (about 4,000 lux) using fluorescent lamp illumination. After the cultivation for about 2 months, seeds were harvested.

Next, the following transformants were prepared by using the *Arabidopsis thaliana* transformant having the introduced p909CTE as a parental strain.

The plasmid p909Pnapus-NaKASIV-Tnapin was introduced into the *Agrobacterium tumafaciens* GV3101 strain, and *Arabidopsis thaliana* having the introduced p909CTE was transformed by using the same. To a material in which an inflorescence of *Arabidopsis thaliana* grown for about 1.5 months after being seeded was excised, and the *Arabi*- dopsis thaliana was further grown for six to seven days, Agrobacterium having the introduced the plasmid was infected. The resultant seeds were seeded to MS agar medium (containing 100 µg/mL of claforan and 7 µg/mL of bialaphos), and the transformants were selected. The obtained transformants were grown at room temperature of 22° C. under the conditions of a light period of 24 hours using fluorescent lamp illumination. After the cultivation for about 2 months, seeds were harvested.

4. Extraction and Methyl Esterification of Fatty Acids

The *Arabidopsis thaliana* seeds thus harvested were crushed by using Multi-beads shocker (manufactured by Yasui Kikai). To the crushed seeds, 20 µL of 7-pentadecanone (0.5 mg/mL dissolved in methanol) (internal standard) and 20 µL of acetic acid were added. Then, 0.25 mL of chloroform and 0.5 mL of methanol were added thereto, and the mixture was sufficiently stirred and then was left to stand for 15 minutes. Further, 0.25 mL of a 1.5% KCl and 0.25 mL of chloroform were added thereto, and the mixture was sufficiently stirred and then was left to stand for 15 minutes. The mixture was centrifuged for 5 minutes at room temperature and at 1,500 rpm, and then the lower layer was collected and dried with nitrogen gas. To the dried sample, 100 µL of 0.5 N potassium hydroxide-methanol solution was added, and the mixture was kept at a constant temperature of 70° C. for 30 minutes to hydrolyze triacylglycerol. The dried product was dissolved by adding 0.3 mL of a boron trifluoride-methanol complex solution, and the solution was kept at a constant temperature of 80° C. for 10 minutes to thereby carry out methyl esterification of fatty acids. Thereafter, 0.2 mL of saturated brine and 0.3 mL of hexane were added thereto, and the mixture was sufficiently stirred and then was left to stand for 30 minutes. The hexane layer (upper layer) containing methyl esters of fatty acids was collected and supplied to gas chromatographic (GC) analysis.

5. GC Analysis

The GC analysis was carried out under the conditions as follows.

Capillary column: DB-1 MS 30 m×200 µm×0.25 µm (J&W Scientific)
Mobile layer: high purity helium
Flow rate inside the column: 1.0 mL/min
Temperature rise program: 150° C. (for 0.5 min.)→320° C. (for 2 min.)
Equilibration time: for 1 min.
Injection port: split injection (split ratio: 75:1)
Pressure 14.49 psi, 104 mL/min
Amount of injection: 5 µL
Cleaning vial: methanol/chloroform
Detector temperature: 300° C.

The obtained data was analyzed in a manner similar to the method in Example 1. The results are shown in FIG. 16.

As shown in FIG. 16, in the strain having the introduced NoKASIV gene and CTE gene, a content of each of the C12:0 and C14:0 fatty acids was higher in comparison with the strain having the introduced CTE gene (parent strain).

Having described our invention as related to the present embodiments, it is our intention that the invention not be limited by any of the details of the description, unless otherwise specified, but rather be construed broadly within its spirit and scope as set out in the accompanying claims.

This application claims priority on Patent Application No. 2014-040536 filed in Japan on Mar. 3, 2014, which is entirely herein incorporated by reference.

What is claimed is:

1. A method of producing a lipid, comprising the following steps (1) and (2):
   (1) transforming a host cell with (i) a gene encoding the following protein (a) or (b) and (ii) a gene encoding an acyl-ACP thioesterase having specificity for a medium chain acyl-ACP, thereby obtaining a transformant, and
   (2) allowing the transformant to produce a lipid and collecting the lipid from the transformant;
   wherein (a) and (b) are:
   (a) A protein consisting of the amino acid sequence set forth in SEQ ID NO: 1; and
   (b) A protein consisting of an amino acid sequence having 95% or more sequence identity with the amino acid sequence of SEQ ID NO: 1, and having β-ketoacyl-ACP synthase activity;
   wherein the host cell is a microalga.

2. The method of producing a lipid according to claim 1, wherein the lipid is a medium chain fatty acid or an ester thereof.

3. The method of producing a lipid according to claim 1, wherein the protein (b) is a β-ketoacyl-ACP synthase having specificity for a medium chain acyl-ACP.

4. The method of producing a lipid according to claim 2, wherein the medium-chain fatty acid is a C12:0 or C14:0 fatty acid or an ester thereof.

5. The method of producing a lipid according to claim 1, wherein step (2) comprises culturing the transformant in a cerulenin-containing medium.

6. The method of producing a lipid according to claim 4, wherein the medium chain fatty acid is a C12:0 fatty acid or an ester thereof.

7. The method of producing a lipid according to claim 1, wherein the microalga belongs to the genus *Nannochloropsis*.

8. The method of producing a lipid according to claim 4, wherein the medium chain fatty acid is a C14:0 fatty acid or an ester thereof.

9. A host cell transformed with (i) a gene encoding the following protein (a) or (b) and (ii) a gene encoding an acyl-ACP thioesterase having specificity for a medium chain acyl-ACP;
   wherein (a) and (b) are:
   (a) A protein consisting of the amino acid sequence set forth in SEQ ID NO: 1; and
   (b) A protein consisting of an amino acid sequence having 95% or more sequence identity with the amino acid sequence of SEQ ID NO: 1, and having β-ketoacyl-ACP synthase activity;
   wherein the host cell is a microalga.

10. The transformed host cell according to claim 9, wherein the transformed host cell produces a C12:0 or C14:0 fatty acid or an ester thereof.

11. The transformed host cell according to claim 10, wherein the transformed host cell produces a C12:0 fatty acid or an ester thereof.

12. The transformed host cell according to claim 9, wherein the microalga belongs to the genus *Nannochloropsis*.

13. The transformed host cell according to claim 10, wherein the transformed host cell produces a C14:0 fatty acid or an ester thereof.

* * * * *

SEQUENCE LISTING

```
<160> NUMBER OF SEQ ID NOS: 92

<210> SEQ ID NO 1
<211> LENGTH: 454
<212> TYPE: PRT
<213> ORGANISM: Nannochloropsis oculata NIES2145

<400> SEQUENCE: 1

Met Arg Val Ser Ser Ala Val Leu Gly Cys Ala Leu Leu Phe Ile
1               5                   10                  15

Ala Pro Thr Leu Ala Tyr Leu Pro Thr Asn Val Arg Ala Ser Lys Gly
                20                  25                  30

Arg Ile Tyr Met Lys Glu Lys Thr Gln Arg Val Val Thr Gly Leu
            35                  40                  45

Gly Pro Ile Ser Ala Val Gly Ile Gly Lys Asp Asp Phe Trp Lys Ala
        50                  55                  60

Leu Leu Glu Gly Lys Cys Gly Ile Asp Lys Ile Ser Gly Phe Asp Pro
65                  70                  75                  80

Ser Gly Leu Thr Cys Gln Ile Gly Ala Glu Val Lys Gly Phe Asp Ala
                85                  90                  95

Lys Pro Tyr Phe Lys Asp Lys Lys Ser Ala Val Arg Asn Asp Arg Val
                100                 105                 110

Thr Leu Met Gly Val Ala Ala Ser Arg Ile Ala Val Asp Asp Ala Arg
            115                 120                 125

Leu Asp Leu Ala Thr Val Glu Gly Glu Arg Phe Gly Val Val Val Gly
        130                 135                 140

Ser Ala Phe Gly Gly Leu Gln Thr Leu Glu Thr Gln Ile Gln Ser Met
```

```
            145                 150                 155                 160
        Asn Glu Lys Gly Pro Gly Ala Val Ser Pro Phe Ala Val Pro Met Leu
                        165                 170                 175

Leu Ser Asn Leu Ile Ser Gly Val Ile Ala Leu Glu Asn Gly Ala Lys
                        180                 185                 190

Gly Pro Asn Tyr Val Val Asn Ser Ala Cys Ala Ala Ser Thr His Ala
                        195                 200                 205

Leu Gly Leu Ala Tyr Ala His Ile Ala His Gly Glu Ala Asp Val Cys
                210                 215                 220

Leu Ala Gly Gly Ala Glu Ala Ala Val Thr Pro Phe Gly Tyr Ala Gly
        225                 230                 235                 240

Phe Cys Ser Met Lys Ala Met Ala Thr Lys Tyr Asn Asp Asn Pro Ser
                        245                 250                 255

Gln Gly Ser Arg Pro Phe Asp Lys Asp Arg Cys Gly Phe Val Met Gly
                        260                 265                 270

Glu Gly Ala Gly Met Leu Val Leu Glu Ser Leu Glu His Ala Gln Lys
                        275                 280                 285

Arg Gly Ala His Ile Tyr Ala Glu Val Ala Gly Phe Gly Gln Ala Cys
                290                 295                 300

Asp Ala His His Ile Thr Thr Pro His Pro Glu Gly Ala Gly Leu Ala
        305                 310                 315                 320

Lys Ala Ile Thr Leu Ala Leu Asp Asp Ala Gly Leu Asp Lys Gly Asp
                        325                 330                 335

Leu Thr Tyr Ile Asn Ala His Gly Thr Ser Thr Ala Tyr Asn Asp Lys
                        340                 345                 350

Phe Glu Thr Leu Ala Val Lys Lys Ala Leu Gly Glu Glu Asn Ala Lys
                        355                 360                 365

Arg Met Tyr Leu Ser Ser Thr Lys Gly Ser Thr Gly His Thr Leu Gly
                370                 375                 380

Ala Ala Gly Gly Leu Glu Ala Ile Ala Thr Val Leu Ala Ile Glu Thr
        385                 390                 395                 400

Leu Thr Leu Pro Pro Thr Ile Asn Tyr Glu Thr Pro Asp Pro Asp Cys
                        405                 410                 415

Asp Leu Asn Val Val Pro Asn Lys Pro Ile Lys Val Ala Glu Ile Lys
                        420                 425                 430

Ala Ala Ala Ser Gln Ser Ala Gly Phe Gly Gly His Asp Ser Val Val
                        435                 440                 445

Ile Phe Lys Pro Phe Lys
                        450

<210> SEQ ID NO 2
<211> LENGTH: 1365
<212> TYPE: DNA
<213> ORGANISM: Nannochloropsis oculata NIES2145

<400> SEQUENCE: 2
atgcgggtct ccagtagcgc cgttttaggc tgcgccctcc tcttcatcgc ccctaccttg      60
gcatacctgc ctaccaacgt gcgcgcctca aagggccgaa tctacatgaa ggagaagacc     120
caacgcgtgg tcgtgacagg cctagggccc atatcggccg tagggatcgg caaggacgat     180
ttctggaagg cgttgctaga ggggaagtgc ggcattgaca agatcagtgg ctttgaccct     240
agtggattga cgtgccaaat tggtgcggaa gtgaagggtt ttgatgcgaa gccgtatttt     300
aaggacaaga aaagcgccgt ccgtaacgac cgtgtgcaca ctgatggggt ggccgcttca     360
```

```
agaatcgccg ttgatgatgc caggctggac ttggccacag tggaaggaga gcgcttcggc    420
gtggtggtgg gctccgcttt tgggggcctg caaacgctcg agacgcagat tcagagcatg    480
aatgagaagg gcccgggggc tgtgtcgccc tttgcggttc ccatgttgtt gtccaacttg    540
atctcgggcg tgattgcctt ggagaacggg gcaaaaggac cgaactacgt ggtgaatagc    600
gcgtgtgccg cctcgaccca tgccctcggt ctggcgtacg cccatatcgc gcacggggag    660
gcggatgtct gcttggccgg cggggcgagg gctgccgtga caccgttcgg gtacgcgggg    720
ttttgctcca tgaaagccat ggcgaccaaa tacaacgaca cccctcccca aggctcccgt    780
cccttcgaca aggatcggtg cggctttgtc atgggcgagg gtgccggtat gctcgtcctc    840
gaatctctcg aacacgccca aaaacgcggc gcgcacatct atgccgaagt cgccggcttt    900
ggtcaggcct gtgacgccca ccatatcacg acccctcacc ccgaggggc gggtctggcg    960 aaagccatca ccttggcatt ggatgacgcg ggcttggaca agggtgattt aacgtacatc    1020
aacgcccatg gcaccagcac ggcgtacaac gacaagttcg agacgttggc ggtcaagaag    1080
gccttggggg aggagaacgc caagaggatg tatttatcgt cgaccaaggg gtcgacggga    1140
cacacgctcg gggccgcggg agggttggag gcgattgcga cagtactagc gattgagacg    1200
ttgaccttgc cccccaccat caactatgag acaccagacc cggactgtga cctgaatgtg    1260
gttcccaaca aacccattaa agtggcggag atcaaagccg ctgcttctca gtcggcaggg    1320
tttggagggc atgactcggt tgtaatcttc aaaccgttca agtaa                    1365

<210> SEQ ID NO 3
<211> LENGTH: 36
<212> TYPE: DNA
<213> ORGANISM: Artificial Sequence
<220> FEATURE:
<223> OTHER INFORMATION: PCR primer 1 for NoKASIV

<400> SEQUENCE: 3
attcgagctc ggtacatgcg ggtctccagt agcgcc                              36

<210> SEQ ID NO 4
<211> LENGTH: 34
<212> TYPE: DNA
<213> ORGANISM: Artificial Sequence
<220> FEATURE:
<223> OTHER INFORMATION: PCR primer 2 for NoKASIV

<400> SEQUENCE: 4
caagcttgca tgcctttact tgaacggttt gaag                                34

<210> SEQ ID NO 5
<211> LENGTH: 18
<212> TYPE: DNA
<213> ORGANISM: Artificial Sequence
<220> FEATURE:
<223> OTHER INFORMATION: PCR primer 1 for pSTV28

<400> SEQUENCE: 5
gtaccgagct cgaattcg                                                  18

<210> SEQ ID NO 6
<211> LENGTH: 20
<212> TYPE: DNA
<213> ORGANISM: Artificial Sequence
<220> FEATURE:
<223> OTHER INFORMATION: PCR primer 2 for pSTV28

<400> SEQUENCE: 6
```
aggcatgcaa gcttggcact                                              20

<210> SEQ ID NO 7
<211> LENGTH: 35
<212> TYPE: DNA
<213> ORGANISM: Artificial Sequence
<220> FEATURE:
<223> OTHER INFORMATION: PCR primer 1 for BTE

<400> SEQUENCE: 7
ggagaaaaaa ctataatgtc aggaacattc aatga                             35

<210> SEQ ID NO 8
<211> LENGTH: 35
<212> TYPE: DNA
<213> ORGANISM: Artificial Sequence
<220> FEATURE:
<223> OTHER INFORMATION: PCR primer 2 for BTE

<400> SEQUENCE: 8
ttataataca gttttttacc caactatctt caatt                             35

<210> SEQ ID NO 9
<211> LENGTH: 37
<212> TYPE: DNA
<213> ORGANISM: Artificial Sequence
<220> FEATURE:
<223> OTHER INFORMATION: PCR primer 1 for VCP1 promoter

<400> SEQUENCE: 9
cgagctcggt acccgggcgg tcttttgtcc tttcctc                           37

<210> SEQ ID NO 10
<211> LENGTH: 22
<212> TYPE: DNA
<213> ORGANISM: Artificial Sequence
<220> FEATURE:
<223> OTHER INFORMATION: PCR primer 2 for VCP1 promoter

<400> SEQUENCE: 10
aatctgctcg gagggagga tc                                            22

<210> SEQ ID NO 11
<211> LENGTH: 36
<212> TYPE: DNA
<213> ORGANISM: Artificial Sequence
<220> FEATURE:
<223> OTHER INFORMATION: PCR primer 1 for VCP1 chloroplast transit
      signal

<400> SEQUENCE: 11
ccctccgagc agattatgaa gaccgccgct ctcctc                            36

<210> SEQ ID NO 12
<211> LENGTH: 28
<212> TYPE: DNA
<213> ORGANISM: Artificial Sequence
<220> FEATURE:
<223> OTHER INFORMATION: PCR primer 2 for VCP1 chloroplast transit
      signal

<400> SEQUENCE: 12
gcgcgcaaca ccgcgggtgc gggagaac                                     28

<210> SEQ ID NO 13

```
<211> LENGTH: 21
<212> TYPE: DNA
<213> ORGANISM: Artificial Sequence
<220> FEATURE:
<223> OTHER INFORMATION: PCR primer 1 for VCP1 terminator

<400> SEQUENCE: 13
gcttctgtgg aagagccagt g                                            21

<210> SEQ ID NO 14
<211> LENGTH: 35
<212> TYPE: DNA
<213> ORGANISM: Artificial Sequence
<220> FEATURE:
<223> OTHER INFORMATION: PCR primer 2 for VCP1 terminator

<400> SEQUENCE: 14
actctagagg atcccctgat cttgtccatc tcgtg                             35

<210> SEQ ID NO 15
<211> LENGTH: 35
<212> TYPE: DNA
<213> ORGANISM: Artificial Sequence
<220> FEATURE:
<223> OTHER INFORMATION: PCR primer 1 for plasmid pUC19

<400> SEQUENCE: 15
gggatcctct agagtcgacc tgcaggcatg caagc                             35

<210> SEQ ID NO 16
<211> LENGTH: 20
<212> TYPE: DNA
<213> ORGANISM: Artificial Sequence
<220> FEATURE:
<223> OTHER INFORMATION: PCR primer 2 for plasmid pUC19

<400> SEQUENCE: 16
cgggtaccga gctcgaattc                                              20

<210> SEQ ID NO 17
<211> LENGTH: 35
<212> TYPE: DNA
<213> ORGANISM: Artificial Sequence
<220> FEATURE:
<223> OTHER INFORMATION: PCR primer 1 for Zeocin resistance gene

<400> SEQUENCE: 17
tccgagcaga ttatgatggc caagctgacc agcgc                             35

<210> SEQ ID NO 18
<211> LENGTH: 35
<212> TYPE: DNA
<213> ORGANISM: Artificial Sequence
<220> FEATURE:
<223> OTHER INFORMATION: PCR primer 2 for Zeocin resistance gene

<400> SEQUENCE: 18
ctcttccaca gaagcttagt cctgctcctc ggcca                             35

<210> SEQ ID NO 19
<211> LENGTH: 35
<212> TYPE: DNA
<213> ORGANISM: Artificial Sequence
<220> FEATURE:
<223> OTHER INFORMATION: PCR primer 3 for NoKASIV

<400> SEQUENCE: 19
```

```
aaatcataca gcaggatgcg ggtctccagt agcgc                          35
```

<210> SEQ ID NO 20
<211> LENGTH: 34
<212> TYPE: DNA
<213> ORGANISM: Artificial Sequence
<220> FEATURE:
<223> OTHER INFORMATION: PCR primer 4 for NoKASIV

<400> SEQUENCE: 20

```
ctcttccaca gaagcttact tgaacggttt gaag                           34
```

<210> SEQ ID NO 21
<211> LENGTH: 35
<212> TYPE: DNA
<213> ORGANISM: Artificial Sequence
<220> FEATURE:
<223> OTHER INFORMATION: PCR primer 1 for UEP promoter

<400> SEQUENCE: 21

```
cgagctcggt acccggctgc tgccccgacc gtatc                          35
```

<210> SEQ ID NO 22
<211> LENGTH: 21
<212> TYPE: DNA
<213> ORGANISM: Artificial Sequence
<220> FEATURE:
<223> OTHER INFORMATION: PCR primer 2 for UEP promoter

<400> SEQUENCE: 22

```
cctgctgtat gattttggca c                                         21
```

<210> SEQ ID NO 23
<211> LENGTH: 35
<212> TYPE: DNA
<213> ORGANISM: Artificial Sequence
<220> FEATURE:
<223> OTHER INFORMATION: PCR primer 1 for Paromomycin resistance gene

<400> SEQUENCE: 23

```
aagaagctgt cttttatggt cgagattcga agcat                          35
```

<210> SEQ ID NO 24
<211> LENGTH: 35
<212> TYPE: DNA
<213> ORGANISM: Artificial Sequence
<220> FEATURE:
<223> OTHER INFORMATION: PCR primer 2 for Paromomycin resistance gene

<400> SEQUENCE: 24

```
ctcttccaca gaagctcaga agaactcgtc caaca                          35
```

<210> SEQ ID NO 25
<211> LENGTH: 35
<212> TYPE: DNA
<213> ORGANISM: Artificial Sequence
<220> FEATURE:
<223> OTHER INFORMATION: PCR primer 1 for TUB promoter

<400> SEQUENCE: 25

```
cgagctcggt acccgactgc gcatggattg accga                          35
```

<210> SEQ ID NO 26
<211> LENGTH: 20
<212> TYPE: DNA

<213> ORGANISM: Artificial Sequence
<220> FEATURE:
<223> OTHER INFORMATION: PCR primer 2 for TUB promoter

<400> SEQUENCE: 26
atatcaagaa gctgtctttt                                                    20

<210> SEQ ID NO 27
<211> LENGTH: 27
<212> TYPE: DNA
<213> ORGANISM: Artificial Sequence
<220> FEATURE:
<223> OTHER INFORMATION: PCR primer 3 for VCP1 promoter

<400> SEQUENCE: 27
ggcggtcttt tgtcctttcc tctatag                                            27

<210> SEQ ID NO 28
<211> LENGTH: 26
<212> TYPE: DNA
<213> ORGANISM: Artificial Sequence
<220> FEATURE:
<223> OTHER INFORMATION: PCR primer 3 for VCP1 terminator

<400> SEQUENCE: 28
ctgatcttgt ccatctcgtg tgccac                                             26

<210> SEQ ID NO 29
<211> LENGTH: 20
<212> TYPE: DNA
<213> ORGANISM: Artificial Sequence
<220> FEATURE:
<223> OTHER INFORMATION: PCR primer 3 for UEP promoter

<400> SEQUENCE: 29
gctgctgccc cgaccgtatc                                                    20

<210> SEQ ID NO 30
<211> LENGTH: 21
<212> TYPE: DNA
<213> ORGANISM: Artificial Sequence
<220> FEATURE:
<223> OTHER INFORMATION: PCR primer 3 for TUB promoter

<400> SEQUENCE: 30
actgcgcatg gattgaccga c                                                  21

<210> SEQ ID NO 31
<211> LENGTH: 35
<212> TYPE: DNA
<213> ORGANISM: Artificial Sequence
<220> FEATURE:
<223> OTHER INFORMATION: PCR primer 1 for NgKASIV

<400> SEQUENCE: 31
acacaggaaa cagctatgga gaagctatcc ctcgc                                   35

<210> SEQ ID NO 32
<211> LENGTH: 35
<212> TYPE: DNA
<213> ORGANISM: Artificial Sequence
<220> FEATURE:
<223> OTHER INFORMATION: PCR primer 2 for NgKASIV

<400> SEQUENCE: 32 acaaatatt aacgcttaag gaacgtactt cttga                                    35

<210> SEQ ID NO 33
<211> LENGTH: 35
<212> TYPE: DNA
<213> ORGANISM: Artificial Sequence
<220> FEATURE:
<223> OTHER INFORMATION: PCR primer 1 for EKASI

<400> SEQUENCE: 33
attcgagctc ggtacatgaa acgtgcagtg attac                    35

<210> SEQ ID NO 34
<211> LENGTH: 35
<212> TYPE: DNA
<213> ORGANISM: Artificial Sequence
<220> FEATURE:
<223> OTHER INFORMATION: PCR primer 2 for EKASI

<400> SEQUENCE: 34
caagcttgca tgcctttaat ctttcagctt gcgca                    35

<210> SEQ ID NO 35
<211> LENGTH: 37
<212> TYPE: DNA
<213> ORGANISM: Artificial Sequence
<220> FEATURE:
<223> OTHER INFORMATION: PCR primer 1 for EKASII

<400> SEQUENCE: 35
attcgagctc ggtacatgtc taagcgtcgt gtagttg                  37

<210> SEQ ID NO 36
<211> LENGTH: 35
<212> TYPE: DNA
<213> ORGANISM: Artificial Sequence
<220> FEATURE:
<223> OTHER INFORMATION: PCR primer 2 for EKASII

<400> SEQUENCE: 36
caagcttgca tgcctttaga tcttttaaa gatca                     35

<210> SEQ ID NO 37
<211> LENGTH: 36
<212> TYPE: DNA
<213> ORGANISM: Artificial Sequence
<220> FEATURE:
<223> OTHER INFORMATION: PCR primer 1 for NoKASIorII

<400> SEQUENCE: 37
acacaggaaa cagctatggc ggacttgccc ccgctt                   36

<210> SEQ ID NO 38
<211> LENGTH: 35
<212> TYPE: DNA
<213> ORGANISM: Artificial Sequence
<220> FEATURE:
<223> OTHER INFORMATION: PCR primer 2 for NoKASIorII

<400> SEQUENCE: 38
acaaaatatt aacgcctagg caacatactt cttga                    35

<210> SEQ ID NO 39
<211> LENGTH: 802
<212> TYPE: DNA
<213> ORGANISM: Artificial Sequence
<220> FEATURE:

<223> OTHER INFORMATION: VCP1 promoter

<400> SEQUENCE: 39

```
ggcggtcttt tgtcctttcc tctatagccc gcccgtctag agggcacacg cgatgatctt      60
tatatctctt catgtgtctt tgttttaact aggatactgc cgggtgaatg cccatcggac     120
aagaggccaa actctatcta caccctttg acttctgttg tggtcgtagt gtgtgcttgc      180
atgccctgaa agtccaggca tcccacttgt gctctaaccc cattcaaaac agcagaagtg     240
cttaattaag atatagattc atgatctcct gtccctcct tcttacctt tcacaaacct      300
cacacagaag tctccactct tcgcctctaa aacctctttt taaattatgg taagttcgtg     360
cggcagtggg ttttcggatc tatatttgtc aagatccagt tcaaggtcag ggatgtagat     420
taagtacaga aggagaagca caagcgcgcc agttcgcccc tcacggcctg gagcagggca     480
tttaatccct ctatcttacc agaaccatac tatacaacca atcctgttgg catcgctctg     540
tctatttgtc gtgcgtgcat gtgtccatgg tgtggtgggg ggcagggggtt ttcggggttg    600
cggttgaagg caccttatca gaaagatgcc ctcagagata gaggtagccc cctccccccg     660
atcttcgacc agtcctgtca ggcgaacact ttcacccgtc gttcacctcg ttacacacaa     720
ggagtagacc tctgaagttc taattgtcat aaatgcccct ccccctccc tctttcccctt    780
gatcctcccc tccgagcaga tt                                             802
```

<210> SEQ ID NO 40
<211> LENGTH: 99
<212> TYPE: DNA
<213> ORGANISM: Artificial Sequence
<220> FEATURE:
<223> OTHER INFORMATION: VCP1 chloroplast transit signal

<400> SEQUENCE: 40

```
atgaagaccg ccgctctcct cactgtctcc accctcatgg gcgcccaggc ctttatggcc      60
cccgccccca gttctcccg cacccgcggt gttgcgcgc                             99
```

<210> SEQ ID NO 41
<211> LENGTH: 643
<212> TYPE: DNA
<213> ORGANISM: Artificial Sequence
<220> FEATURE:
<223> OTHER INFORMATION: VCP1 terminator

<400> SEQUENCE: 41

```
gcttctgtgg aagagccagt ggtagtagca gtagcagcag cagtagcagc cgcagcactc      60
agtgttggcg cgagagattg tccatccctt cttaacctac cggaagagaa ataaggcctt     120
tctcccgtag ctgtcttcgt ttgtttgtgc tgattgcttg atatgagagt gttgaattcc     180
tgcatcatgt ttttctctgt agtcctttcc tacccccgtc attttctttt ctccctggtt     240
cttcttttgt caccctattt ttacataaaa ttttctttgt ttatagtgag aggaaggtag     300
agagggaaa acaagaacaa cgaacgcaag cgtgtgaaag gagggcgagt agaagagaaa      360
cagatctgtt gagcattgag agtggagccg ggggaaaggc ttgtgtgttg tctttgaaaa     420
agttgtttaa atcacgaatc cgttagttct catgtgtacc tctttcacta catgtgatgg     480
agaaaacaaa agtgtgagga ttaattgaag aaaaagaaga gttcgacacg tcaaaccgcc     540
caaaagacgt cacaaagaga acttgattct ctttgccgtg ttgatcctgt cttttccccc     600
agcttttctt gccacccgtg gcacacgaga tggacaagat cag                       643
```

<210> SEQ ID NO 42
<211> LENGTH: 375
<212> TYPE: DNA
<213> ORGANISM: Artificial Sequence
<220> FEATURE:
<223> OTHER INFORMATION: Zeocin resistance gene

<400> SEQUENCE: 42

| | |
|---|---|
| atggccaagc tgaccagcgc cgttccggtg ctcaccgcgc gcgacgtcgc cggagcggtc | 60 |
| gagttctgga ccgaccggct cgggttctcc cgggacttcg tggaggacga cttcgccggt | 120 |
| gtggtccggg acgacgtgac cctgttcatc agcgcggtcc aggaccaggt ggtgccggac | 180 |
| aacaccctgg cctgggtgtg ggtgcgcggc ctggacgagc tgtacgccga gtggtcggag | 240 |
| gtcgtgtcca cgaacttccg ggacgcctcc gggccggcca tgaccgagat cggcgagcag | 300 |
| ccgtgggggc gggagttcgc cctgcgcgac ccggccggca actgcgtgca cttcgtggcc | 360 |
| gaggagcagg actaa | 375 |

<210> SEQ ID NO 43
<211> LENGTH: 822
<212> TYPE: DNA
<213> ORGANISM: Artificial Sequence
<220> FEATURE:
<223> OTHER INFORMATION: Paromomycin resistance gene

<400> SEQUENCE: 43

| | |
|---|---|
| atggtcgaga ttcgaagcat ggacgatgcg ttgcgtgcac tgcggggtcg gtatccggt | 60 |
| tgtgagtggg ttgttgtgga ggatggggcc tcggggctg tgtttatcg gcttcggggt | 120 |
| ggtgggcggg agttgtttgt caaggtggca gctctggggg ccggggtggg cttgttgggt | 180 |
| gaggctgaac ggctggtgtg gttggcgag gtgggattc ccgtacctcg tgttgtggag | 240 |
| ggtggtgggg acgagagggt cgcctggttg gtcaccgaag cggttccggg cgtccggcc | 300 |
| agtgcgcggt ggccgcggga gcagcggctg acgtggcgg tggcgctcgc ggggctcgct | 360 |
| cgttcgctgc acgcgctgga ctgggagcgg tgtccgttcg atcgcagtct cgcggtgacg | 420 |
| gtgccgcagg cggcccgtgc tgtcgctgaa gggagcgtcg acttggagga tctggacgag | 480 |
| gagcggaagg ggtggtcggg ggagcggctt ctcgccgagc tggagcggac tcggcctgcg | 540 |
| gacgaggatc tggcggtttg ccacggtgac ctgtgcccgg acaacgtgct gctcgaccct | 600 |
| cgtacctgcg aggtgaccgg gctgatcgac gtggggcggg tcggccgtgc ggaccggcac | 660 |
| tccgatctcg cgctggtgct gcgcgagctg gcccacgagg aggacccgtg gttcgggccg | 720 |
| gagtgttccg cggcgttcct gcgggagtac gggcgcgggt gggatgggc ggtatcggag | 780 |
| gaaaagctgg cgttttaccg gctgttggac gagttcttct ga | 822 |

<210> SEQ ID NO 44
<211> LENGTH: 490
<212> TYPE: DNA
<213> ORGANISM: Artificial Sequence
<220> FEATURE:
<223> OTHER INFORMATION: TUB promoter

<400> SEQUENCE: 44

| | |
|---|---|
| actgcgcatg gattgaccga cggccggttg ccaacttttg gggtcggccc cccttttcta | 60 |
| gcccttgccc gtccagcaat taaaaattat caacggcata ccggcactgg aagcttcggg | 120 |
| tttacaattt tggcttgcct tcctaatact gtaccgcgga gaacgtatga tattacagaa | 180 |
| aaatgccttg cacagttagc gcaaagggaa aacgtttctc cgccattgta cttttggaa | 240 |

-continued

```
gagggaaagc gattgtaaaa tatggctctc cgctacgaga gtttgggctg ttgatacatg    300
tgaaaataag tgtggacgac tttgaatgac ttgatcaggc tgtttgcaca tataaccagc    360
gcgcatgcac ttctgacatg tcaatgacga aatttcacac ttcaccaata aattgtatcc    420
ttacgttttg tctttctcac acgcacatat atgatcatag ataaaagcca atatcaagaa    480
gctgtctttt                                                            490
```

<210> SEQ ID NO 45
<211> LENGTH: 689
<212> TYPE: DNA
<213> ORGANISM: Artificial Sequence
<220> FEATURE:
<223> OTHER INFORMATION: UEP promoter

<400> SEQUENCE: 45

```
gctgctgccc cgaccgtatc tccaagtcag acatgaaatc ttcagttgcg ttaaaaactc     60
tacgatgcta ccagcgttaa ataaccttgc ccacgccttt aaacgtaccc gatcattaac    120
atatcgactg gctgccttgg ctttgcacca gccatcatca gacttaacga tgggtatgtt    180
gcttgccttt cctgcttgaa gggggtccga ctctctgctt tctcgatcgc gggtgtgacc    240
tctgaattgg aatgtaaaaa tgtaagaagc gacgtgtccg gtaaagaaat gcccaagctc    300
catcaaatct gcgttgtcgg cgaccaaacc atgctggctc gtcgacctgc ccggatgca     360 ggagcatggc actcggcggc atggcacttg agcctcgcgg gaggaatgtg tgtggttggg    420
cgcaggctgt ggacggcccc cctccagcga agcggtcgcc tccctttccg acgctttgtg    480
cacgttgtct ggtgtcctct gtctcacgca cctcttcacc gacgtggtgt ccctcttgtt    540
gctggtgagg gacttggaat gtggtcctgg ttctatcctg ggcgcgtgtg ttccttttt    600 tctctaccgt tattctctcc atttctgatg tctcaccacc atctccctca ccctccaacc    660
gcgtcgttgt gccaaaatca tacagcagg                                       689
```

<210> SEQ ID NO 46
<211> LENGTH: 303
<212> TYPE: PRT
<213> ORGANISM: Cocos nucifera

<400> SEQUENCE: 46

```
Leu Asp Ser Lys Lys Arg Gly Ala Asp Ala Val Ala Asp Ala Ser Gly
1               5                   10                  15

Val Gly Lys Met Val Lys Asn Gly Leu Val Tyr Arg Gln Asn Phe Ser
            20                  25                  30

Ile Arg Ser Tyr Glu Ile Gly Val Asp Lys Arg Ala Ser Val Glu Ala
        35                  40                  45

Leu Met Asn His Phe Gln Glu Thr Ser Leu Asn His Cys Lys Cys Ile
    50                  55                  60

Gly Leu Met His Gly Gly Phe Gly Cys Thr Pro Glu Met Thr Arg Arg
65                  70                  75                  80

Asn Leu Ile Trp Val Val Ala Lys Met Leu Val His Val Glu Arg Tyr
                85                  90                  95

Pro Trp Trp Gly Asp Val Val Gln Ile Asn Thr Trp Ile Ser Ser Ser
            100                 105                 110

Gly Lys Asn Gly Met Gly Arg Asp Trp His Val His Asp Cys Gln Thr
        115                 120                 125

Gly Leu Pro Ile Met Arg Gly Thr Ser Val Trp Val Met Met Asp Lys
    130                 135                 140
```

His Thr Arg Arg Leu Ser Lys Leu Pro Glu Glu Val Arg Ala Glu Ile
145                 150                 155                 160

Thr Pro Phe Phe Ser Glu Arg Asp Ala Val Leu Asp Asp Asn Gly Arg
            165                 170                 175

Lys Leu Pro Lys Phe Asp Asp Ser Ala Ala His Val Arg Arg Gly
            180                 185                 190

Leu Thr Pro Arg Trp His Asp Phe Asp Val Asn Gln His Val Asn Asn
        195                 200                 205

Val Lys Tyr Val Gly Trp Ile Leu Glu Ser Val Pro Val Trp Met Leu
210                 215                 220

Asp Gly Tyr Glu Val Ala Thr Met Ser Leu Glu Tyr Arg Arg Glu Cys
225                 230                 235                 240

Arg Met Asp Ser Val Val Gln Ser Leu Thr Ala Val Ser Ser Asp His
                245                 250                 255

Ala Asp Gly Ser Pro Ile Val Cys Gln His Leu Leu Arg Leu Glu Asp
            260                 265                 270

Gly Thr Glu Ile Val Arg Gly Gln Thr Glu Trp Arg Pro Lys Gln Gln
        275                 280                 285

Ala Cys Asp Leu Gly Asn Met Gly Leu His Pro Thr Glu Ser Lys
290                 295                 300

<210> SEQ ID NO 47
<211> LENGTH: 912
<212> TYPE: DNA
<213> ORGANISM: Cocos nucifera

<400> SEQUENCE: 47
ctcgattcca agaagagggg ggccgacgcg gtcgcagatg cctctggggt cgggaagatg    60
gtcaagaatg gacttgttta caggcagaat ttttctatcc ggtcctacga aatcggggtt   120
gataaacgtg cttcggtaga ggcattgatg aatcatttcc aggaaacgtc gcttaaccat   180
tgcaagtgta ttggccttat gcatggcggc tttggttgta caccagagat gactcgaaga   240
aatctgatat gggttgttgc caaaatgctg gttcatgtcg aacgttatcc ttggtgggga   300
gacgtggttc aaataaatac gtggattagt tcatctggaa agaatggtat gggacgtgat   360
tggcatgttc atgactgcca aactggccta cctattatga ggggtaccag tgtctgggtc   420
atgatggata acacacgag gagactgtct aaacttcctg aagaagttag agcagagata   480
acccctttct tttcagagcg tgatgctgtt ttggacgata acggcagaaa acttcccaag   540
ttcgatgatg attctgcagc tcatgttcga aggggcttga ctcctcgttg catgatttc   600
gatgtaaatc agcatgtgaa caatgtcaaa tacgtcggct ggattcttga gagcgttcct   660
gtgtggatgt tggatggcta cgaggttgca accatgagtc tggaataccg agggagtgt   720
aggatggata gtgtggtgca gtctctcacc gccgtctctt ccgaccacgc cgacggctcc   780
cccatcgtgt gccagcatct tctgcggctc gaggatggga ctgagattgt gaggggtcaa   840
acagaatgga ggcctaagca gcaggcttgt gatcttggga catgggtct gcacccaact   900
gagagtaaat ga                                                        912

<210> SEQ ID NO 48
<211> LENGTH: 287
<212> TYPE: PRT
<213> ORGANISM: Nannochloropsis oculata NIES2145

<400> SEQUENCE: 48

Met Thr Pro Leu Ala Phe Thr Val Leu Gly Lys Leu Gly Gly Thr Leu

|  1 |  |  |  | 5 |  |  |  |  | 10 |  |  |  |  | 15 |  |
|---|---|---|---|---|---|---|---|---|---|---|---|---|---|---|---|

Thr Phe Ala Cys Val Arg Arg Arg Leu Tyr His Leu Leu Arg Arg Ala
          20                  25                  30

Thr Leu Ser Ser His Tyr Gln Val Thr Arg Pro Tyr Gly His Ser Asn
          35                  40                  45

Ser Gly Cys Ser His Ser Thr Thr Leu Arg Thr Ser Phe Pro Val
     50                  55                  60

Leu Phe Ala Gln Leu Ala Ala Ala Thr Ala Ala Val Val Ala Ala Ile
65                  70                  75                  80

Ser Leu Pro Ser Pro Ser Leu Cys Glu Thr Ala His Ala Gly Thr Glu
                  85                  90                  95

Glu Arg Arg Gly Glu Arg Lys Ala Met Arg Glu Asp Gly Gly Lys Gly
            100               105               110

Glu Ala Thr Ser Ser Ala Thr Cys Asn Pro Ser Leu Phe Glu His His
            115               120               125

Asp Arg Val Asp Thr Lys Leu His Arg Ala Tyr Pro Glu Phe Leu Lys
          130               135               140

Phe His Leu Ile His Glu Thr Leu Arg Gly Lys Glu Lys Ile Asp Gly
145                150               155              160

Tyr Glu Val Tyr Lys Asp Arg Arg Asp Asp Ser Ile Val Ala Tyr Ala
            165               170               175

Arg Leu Gly Lys Leu Leu Ser Gly His Pro Asp Ile Ile His Gly Gly
          180               185               190

Ser Ile Ala Ala Leu Leu Asp Asn Thr Met Gly Val Ala Phe Phe Ala
          195               200               205

Ala Lys Arg Gly Asn Gly Phe Thr Ala Asn Leu Thr Ile Asn Tyr Lys
          210               215               220

Arg Pro Ile Thr Cys Gly Thr Glu Val Lys Val Leu Ala Arg Val Glu
225                230               235              240

Lys Val Glu Gly Arg Lys Val Phe Leu Arg Ala Glu Ile Arg Asp Ala
            245               250               255

Lys Asp Glu Ala Ile Leu Tyr Thr Glu Ala Lys Ser Leu Phe Ile Thr
          260               265               270

Ser Gln Ser Pro Leu Leu Lys Gly Pro Lys Lys Ile Asp Ile Ser
     275                  280                  285

<210> SEQ ID NO 49
<211> LENGTH: 864
<212> TYPE: DNA
<213> ORGANISM: Nannochloropsis oculata NIES2145

<400> SEQUENCE: 49

```
atgacgcctt tggccttcac ggtgctcggc aagcttggtg cacgttgac ttttgcttgt      60
gtacgacgga ggctttatca cttgttacgg cgggcaactt tgtcctccca ttatcaggtc    120
actcggcctt acggtcacag caattccggc tgttcacata gcactaccac acttagaacc    180
agcttcccag tcctctttgc gcaattggca gcagccactg ctgccgtcgt cgctgccatt    240
tccctgccgt cgcctagtct atgcgagacg gcccacgccg ggactgagga gagacgaggt    300
gagaggaagg caatgaggga ggatggtgga aaaggcgagg ccacctcgtc tgctacatgc    360
aatccatcct tattcgaaca tcatgatcgc gtcgacacca agctgcatcg ggcctatcct    420
gaattcctga agtccaccct tatccacgag acgctccgag gcaaagagaa aattgatggc    480
tacgaagttt acaaagacag gcgggatgat tcaattgtgg cgtatgctcg ccttggcaaa    540
```

```
ctgctgagcg acaccccga cataatccac ggagggtcca ttgcggcttt gctggacaat    600
accatgggag ttgccttttt cgccgccaag cgtggcaatg gttttacagc aaatctcacc    660
atcaactaca agcgacccat cacgtgtggc accgaagtca agttttagc tcgagtagag     720 aaggtggaag ggcgcaaggt cttcttgcgg gccgagattc gagacgctaa ggatgaggct    780
atcctctaca ctgaagccaa atccctcttc atcacgtctc aaagtccttt attgaagggc    840
ccaaagaaaa ttgatattag ctag                                           864
```

```
<210> SEQ ID NO 50
<211> LENGTH: 382
<212> TYPE: PRT
<213> ORGANISM: Umbellularia californica

<400> SEQUENCE: 50

Met Ala Thr Thr Ser Leu Ala Ser Ala Phe Cys Ser Met Lys Ala Val
1               5                   10                  15

Met Leu Ala Arg Asp Gly Arg Gly Met Lys Pro Arg Ser Ser Asp Leu
            20                  25                  30

Gln Leu Arg Ala Gly Asn Ala Pro Thr Ser Leu Lys Met Ile Asn Gly
        35                  40                  45

Thr Lys Phe Ser Tyr Thr Glu Ser Leu Lys Arg Leu Pro Asp Trp Ser
    50                  55                  60

Met Leu Phe Ala Val Ile Thr Thr Ile Phe Ser Ala Ala Glu Lys Gln
65                  70                  75                  80

Trp Thr Asn Leu Glu Trp Lys Pro Lys Pro Lys Leu Pro Gln Leu Leu
                85                  90                  95

Asp Asp His Phe Gly Leu His Gly Leu Val Phe Arg Arg Thr Phe Ala
            100                 105                 110

Ile Arg Ser Tyr Glu Val Gly Pro Asp Arg Ser Thr Ser Ile Leu Ala
        115                 120                 125

Val Met Asn His Met Gln Glu Ala Thr Leu Asn His Ala Lys Ser Val
    130                 135                 140

Gly Ile Leu Gly Asp Gly Phe Gly Thr Thr Leu Glu Met Ser Lys Arg
145                 150                 155                 160

Asp Leu Met Trp Val Val Arg Arg Thr His Val Ala Val Glu Arg Tyr
                165                 170                 175

Pro Thr Trp Gly Asp Thr Val Glu Val Glu Cys Trp Ile Gly Ala Ser
            180                 185                 190

Gly Asn Asn Gly Met Arg Arg Asp Phe Leu Val Arg Asp Cys Lys Thr
        195                 200                 205

Gly Glu Ile Leu Thr Arg Cys Thr Ser Leu Ser Val Leu Met Asn Thr
    210                 215                 220

Arg Thr Arg Arg Leu Ser Thr Ile Pro Asp Glu Val Arg Gly Glu Ile
225                 230                 235                 240

Gly Pro Ala Phe Ile Asp Asn Val Ala Val Lys Asp Asp Glu Ile Lys
                245                 250                 255

Lys Leu Gln Lys Leu Asn Asp Ser Thr Ala Asp Tyr Ile Gln Gly Gly
            260                 265                 270

Leu Thr Pro Arg Trp Asn Asp Leu Asp Val Asn Gln His Val Asn Asn
        275                 280                 285

Leu Lys Tyr Val Ala Trp Val Phe Glu Thr Val Pro Asp Ser Ile Phe
    290                 295                 300

Glu Ser His His Ile Ser Ser Phe Thr Leu Glu Tyr Arg Arg Glu Cys
305                 310                 315                 320
```

```
Thr Arg Asp Ser Val Leu Arg Ser Leu Thr Thr Val Ser Gly Gly Ser
            325                 330                 335

Ser Glu Ala Gly Leu Val Cys Asp His Leu Leu Gln Leu Glu Gly Gly
        340                 345                 350

Ser Glu Val Leu Arg Ala Arg Thr Glu Trp Arg Pro Lys Leu Thr Asp
    355                 360                 365

Ser Phe Arg Gly Ile Ser Val Ile Pro Ala Glu Pro Arg Val
370                 375                 380
```

<210> SEQ ID NO 51
<211> LENGTH: 1149
<212> TYPE: DNA
<213> ORGANISM: Umbellularia californica

<400> SEQUENCE: 51

```
atggccacca cctctttagc ttccgctttc tgctcgatga aagctgtaat gttggctcgt        60
gatggccggg gcatgaaacc caggagcagt gatttgcagc tgagggcggg aaatgcgcca       120
acctctttga agatgatcaa tggaccaagt tcagttaca cggagagctt gaaaaggttg        180
cctgactgga gcatgctctt tgcagtgatc acaaccatct tttcggctgc tgagaagcag       240
tggaccaatc tagagtggaa gccgaagccg aagctacccc agttgcttga tgaccatttt       300
ggactgcatg ggttagtttt caggcgcacc tttgccatca gatcttatga ggtgggacct       360
gaccgctcca catctatact ggctgttatg aatcacatgc aggaggctac acttaatcat       420
gcgaagagtg tgggaattct aggagatgga ttcgggacga cgctagagat gagtaagaga       480
gatctgatgt gggttgtgag acgcacgcat gttgctgtgg aacggtaccc tacttggggt       540
gatactgtag aagtagagtg ctggattggt gcatctggaa ataatggcat gcgacgtgat       600
ttccttgtcc gggactgcaa aacaggcgaa attcttacaa gatgtaccag cctttcggtg       660
ctgatgaata caaggacaag gaggttgtcc acaatccctg acgaagttag aggggagata       720
gggcctgcat tcattgataa tgtggctgtc aaggacgatg aaattaagaa actacagaag       780
ctcaatgaca gcactgcaga ttacatccaa ggaggttttga ctcctcgatg gaatgatttg       840
gatgtcaatc agcatgtgaa caacctcaaa tacgttgcct gggttttttga gaccgtccca       900
gactccatct tgagagtca tcatatttcc agcttcactc ttgaatacag agagagtgc        960
acgagggata gcgtgctgcg gtccctgacc actgtctctg gtggctcgtc ggaggctggg      1020
ttagtgtgcg atcacttgct ccagcttgaa ggtgggtctg aggtattgag ggcaagaaca      1080
gagtggaggc ctaagcttac cgatagtttc agagggatta gtgtgatacc cgcagaaccg      1140
agggtgtaa                                                             1149
```

<210> SEQ ID NO 52
<211> LENGTH: 274
<212> TYPE: PRT
<213> ORGANISM: Nannochloropsis gaditana CCMP526

<400> SEQUENCE: 52

```
Met Leu Cys Cys Ala Cys Lys Ser Val His Ala Thr Ile Ser Val Ala
1               5                   10                  15

Phe Ile Gly Thr Arg Lys Pro His Arg Leu Pro Ala Leu Phe Pro Leu
            20                  25                  30

Phe Leu Ala Pro Ala Arg Ala Leu Ser His Gln Glu Pro Asn Pro Ala
        35                  40                  45

Thr Cys Gly Thr Gln Asn Ser Ser Phe Ser Ile Leu Leu Lys Thr Val
```

```
            50                  55                  60
Val Ala Gly Ser Phe Val Gly Ala Phe Ile Ala Gly His Thr Ala
 65                  70                  75                  80

Gly Ala Ser Cys Asp Glu Val Lys Ser Pro Gln Val Asn Asn Val
                 85                  90                  95

Gly Gly Gly Ala Pro Val Thr Ala Pro Tyr Val Thr Phe Ala Ser
                100                 105                 110

Asn Tyr His Asp Arg Val Asp Thr Lys Leu His Arg Ala Tyr Pro Glu
            115                 120                 125

Phe Leu Gln Tyr His Leu Ile His Glu Thr Leu Arg Gly Lys Glu Lys
            130                 135                 140

Ile Glu Gly Tyr Glu Val Tyr Lys Asp Arg Arg Asp Asp Ser Ile Val
145                 150                 155                 160

Ala Phe Ala Arg Leu Gly Lys Leu Leu Ser Gly His Pro Asp Ile Ile
                165                 170                 175

His Gly Gly Ser Ile Ala Ala Leu Leu Asp Asn Thr Met Gly Val Ala
                180                 185                 190

Phe Phe Ala Ala Asn Lys Gly Asn Gly Phe Thr Ala Asn Leu Thr Ile
                195                 200                 205

Asn Tyr Lys Arg Pro Ile Ile Cys Gly Thr Glu Ile Lys Val Leu Ala
            210                 215                 220

Arg Val Glu Arg Phe Glu Gly Arg Lys Val Phe Leu Arg Ala Glu Ile
225                 230                 235                 240

Arg Asp Ala Lys Asp Glu Ala Val Leu Tyr Thr Glu Ala Thr Ser Leu
                245                 250                 255

Phe Ile Thr Ser Gln Ser Pro Leu Leu Thr Gly Pro Lys Lys Val Asp
                260                 265                 270

Ile Ser

<210> SEQ ID NO 53
<211> LENGTH: 825
<212> TYPE: DNA
<213> ORGANISM: Nannochloropsis gaditana CCMP526

<400> SEQUENCE: 53
atgctatgtt gcgcctgtaa atcagtgcat gcgactatta gtgtcgcctt tattggtact    60
cggaagccac atcgtttgcc tgcattgttt ccattgttcc ttgccccggc ccgagcactc   120
agccatcagg agccgaaccc tgcaacgtgc gggacgcaaa actcatcctt ctcgatcttg   180
ttgaaaacgg tagtagcagg atcattcgtc ggtgcggcat tcatcgctgg catacagca   240
ggggctagct gtgatgaagt aaagtctccg caggaggtga acaatgtagg aggcggcgcc   300
ccagtgactg cccctacac ggtcactttt gcgtccaatt atcatgatcg agtggacaca   360
aaacttcata gagcttatcc tgagttttta cagtaccatc ttattcatga aacgcttcga   420
ggcaaggaaa agatagaggg ctacgaggtg tacaaagata gcgtgacga ttctatcgta   480
gcatttgctc gcctcgggaa gcttctcagc gggcatccgg atataatcca tggaggctct   540
atagccgcct tactcgacaa cactatgggc gtggcattct tcgctgccaa taaaggtaat   600
ggcttcactg ccaacctcac aatcaattac aagaggccga tcatttgtgg caccgagatc   660
aaggtcttgg cccgagtgga gcggtttgaa ggacgcaagg ttttcctacg agcagagatt   720
cgagatgcta aggacgaggc agtgttgtac acgaagccca tccctcttta taacttca   780
caaagtcctc tgcttacggg accgaagaag gtggacatca gttag                  825
```

<210> SEQ ID NO 54
<211> LENGTH: 285
<212> TYPE: PRT
<213> ORGANISM: Nannochloropsis granulata NIES2588

<400> SEQUENCE: 54

Met Thr Pro Leu Ala Phe Thr Ala Leu Gly Glu Val Gly Gly Met Leu
1               5                   10                  15

Ala Ala Ala Cys Val Arg Arg Lys Leu His His Leu Leu Arg Arg Ala
            20                  25                  30

Ala Ser Ser Ser Gln Val Thr Arg Pro Tyr Ser His Ser Thr Ala Asn
        35                  40                  45

Ser Thr His Ser Thr Thr Thr Leu Ser Asn Ser Phe Pro Val Leu Phe
    50                  55                  60

Ala Gln Leu Ala Ala Ala Ala Val Met Ala Ala Thr Ser Leu
65                  70                  75                  80

Ser Ser Pro Ser Leu Cys Glu Thr Ala His Thr Asn Thr Glu Glu Arg
                85                  90                  95

Gly Gly Glu Gly Glu Ala Met Arg Glu Lys Gly Gly Glu Gly Glu Ala
            100                 105                 110

Thr Ser Ser Ala Thr Cys Ala Pro Ser Phe Phe Glu His His Asp Arg
        115                 120                 125

Val Asp Thr Lys Leu His Arg Ala Tyr Pro Gly Phe Leu Lys Phe His
    130                 135                 140

Leu Ile His Glu Thr Leu Arg Gly Lys Glu Lys Ile Asp Gly Tyr Glu
145                 150                 155                 160

Val Tyr Lys Asn Arg Arg Asp Asp Ser Val Val Ala Tyr Ala Arg Leu
                165                 170                 175

Gly Lys Leu Leu Ser Gly His Pro Asp Ile Ile His Gly Gly Ser Ile
            180                 185                 190

Ala Ala Leu Leu Asp Asn Thr Met Gly Val Ala Phe Phe Ala Ala Lys
        195                 200                 205

Arg Gly Asn Gly Phe Thr Ala Asn Leu Thr Ile Asn Tyr Lys Arg Pro
    210                 215                 220

Ile Thr Cys Gly Thr Glu Val Lys Val Leu Ala Arg Val Glu Lys Val
225                 230                 235                 240

Glu Gly Arg Lys Val Phe Leu Arg Ala Glu Ile Arg Asp Ala Lys Asp
                245                 250                 255

Glu Ala Ile Leu Tyr Thr Glu Ala Asn Ser Leu Phe Ile Thr Ser Gln
            260                 265                 270

Ser Pro Leu Leu Lys Gly Pro Lys Lys Ile Asp Ile Ser
        275                 280                 285

<210> SEQ ID NO 55
<211> LENGTH: 858
<212> TYPE: DNA
<213> ORGANISM: Nannochloropsis granulata NIES2588

<400> SEQUENCE: 55
atgacgcctt tggccttcac ggcgctcggc gaggtcggtg gcatgttggc tgctgcctgt    60
gtacgacgga agcttcatca cttgttgcgg cgggcagctt cgtcctccca ggtcactcga   120
ccttacagtc acagcaccgc caacagcaca catagcacca ccacacttag caacagcttt   180
ccagtcctct tgcgcaaact cgcagcagcc gctgctgccg tcatggctgc cacttccctg   240
tcgtcgccca gtctatgtga gacggcccac accaatactg aggagagagg aggcgaaggg   300

```
gaggcaatga gggagaaggg tggggaaggc gaggccactt cgtctgctac atgcgctcca    360
tctttcttcg agcatcatga tcgcgtcgac acgaagctgc atcgggccta tcccgagttt    420
ctgaagttcc acctcatcca cgagacgctc cgagggaaag agaaaattga tggctacgaa    480
gtatacaaaa acaggcggga cgattcagtt gtggcgtatg ctcgcctggg caaactgctg    540
agcggacacc ctgacataat tcacggaggg tccatcgctg ctttgctgga acaccatg     600 ggagttgcct ttttcgccgc caagcgcggc aatggtttca cagcaaatct caccatcaac    660
tacaagcgac ccatcacgtg tggcaccgag gtcaaagttc tggctcgagt agagaaggtg    720
gaggggcgca aggtcttttt gcgggctgag atcagggacg ccaaggatga ggctatcctt    780
tacactgaag ccaactccct cttcatcacg tcgcaaagcc ctctattgaa gggcccaaag    840
aaaattgaca ttagctag                                                  858
```

<210> SEQ ID NO 56
<211> LENGTH: 233
<212> TYPE: PRT
<213> ORGANISM: Symbiodinium microadriaticum

<400> SEQUENCE: 56

```
Met Ala Phe Arg Leu Cys Ser Leu Ser Arg Arg Phe Ala Ala His Ala
1               5                   10                  15

Gln Gln Val Leu Arg Lys Glu Ala Gly Phe Glu Phe Arg Ala Ser Cys
            20                  25                  30

Ile Ala Ile Thr Ala Gly Ile Ser Ala Gly Trp Cys Met Gln Gln Ala
        35                  40                  45

Ala Arg Ala Glu Gly Ile Trp Thr Pro His Leu Gly Glu Glu Ala Lys
    50                  55                  60

Leu Leu Asn Leu Gln Arg Glu Met Ala Leu Arg Asp Arg His Asp Lys
65                  70                  75                  80

Gln Phe Val Trp Gln Thr Cys Ser Gly Gln Gly Lys Ile Glu Asp Cys
                85                  90                  95

Arg Ile Tyr His Cys Lys Arg Glu Glu Val Asp Arg Glu Val Ser Leu
            100                 105                 110

Asp Ala Pro Glu Met Val Glu Gly Lys Thr Arg Ile Cys Ala Val Met
        115                 120                 125

Arg Val Gly Asp Glu Leu Asn Gly His Pro Gly Leu Leu His Gly Gly
    130                 135                 140

Phe Thr Ala Ala Val Leu Asp Asp Phe Thr Gly Leu Ala Thr Trp Met
145                 150                 155                 160

Glu Lys Gln Ala Gln Ala Leu Asp Lys Asp Ala Ala Ile Phe Thr Ala
                165                 170                 175

His Met Asp Leu Ser Tyr Arg Arg Pro Leu Lys Ala Lys Ser Glu Tyr
            180                 185                 190

Leu Val Glu Val Cys Val Asp Arg Val Glu Arg Gln Lys Lys Val Phe
        195                 200                 205

Leu Asn Ala Ala Ile Tyr Asp Lys Asp Ser His Ala Cys Val Lys Ala
    210                 215                 220

Lys Val Leu Tyr Ile Val Lys Lys Lys
225                 230
```

<210> SEQ ID NO 57
<211> LENGTH: 702
<212> TYPE: DNA
<213> ORGANISM: Symbiodinium microadriaticum

<400> SEQUENCE: 57

```
atggctttca ggctatgctc tctttcccgg cggtttgctg cgcacgcgca gcaggtgctg      60
cggaaggagg ctggctttga gttccgcgca agctgcatcg ccattaccgc tggcatctct     120
gctggatggt gcatgcagca ggcagcgcgg gcggagggca tctggactcc gcacctgggc     180
gaggaggcca agttgttgaa cctccagcgc gagatggcgc tgagagacag cacgacaag     240
caatttgtgt ggcagacctg cagtggccag ggcaaaattg aggactgccg catatatcac     300
tgcaagcgag aagaagttga tcgtgaggtt cgctggacg cgccggaaat ggtggagggc     360
aaaacacgga tttgtgcagt gatgcgcgtt ggcgacgagc tgaacggcca tcctgggctt     420
ttgcatggcg gcttcactgc cgccgtgctg acgatttca caggcctggc gacctggatg     480
gagaagcaag cgcaggcgct ggacaaggat gcggccattt tcaccgctca catggatctc     540
agctatcggc gaccctgaa ggcgaagtcg gagtacttgg ttgaggtttg cgttgaccgt     600
gttgagcggc aaaagaaggt ctttctgaat gctgccatct atgacaagga cagccatgcc     660
tgcgtgaaag caaaggtgtt gtacatcgtc aaaaagaagt ga                        702
```

<210> SEQ ID NO 58
<211> LENGTH: 458
<212> TYPE: PRT
<213> ORGANISM: Nannochloropsis gaditana CCMP526

<400> SEQUENCE: 58

```
Met Arg Leu Ser Thr Leu Ser Val Leu Gly Pro Ala Leu Gly Cys Ala
1               5                   10                  15

Phe Leu Leu Phe Asp Ser Ser Leu Ala Tyr Leu Pro Ser Tyr Met Arg
                20                  25                  30

Gly Ser Lys Gly Gln Ile Tyr Met Lys Glu Lys Ser Gln Arg Val Val
            35                  40                  45

Val Thr Gly Leu Gly Pro Ile Ser Ala Val Gly Ile Gly Lys Asp Ala
        50                  55                  60

Phe Trp Lys Ala Leu Leu Glu Gly Lys Ser Gly Ile Asp Arg Ile Ser
65                  70                  75                  80

Gly Phe Asp Pro Ser Gly Leu Thr Cys Gln Ile Gly Ala Glu Val Lys
                85                  90                  95

Asp Phe Asp Ala Lys Pro Tyr Phe Lys Asp Arg Lys Ser Ala Val Arg
                100                 105                 110

Asn Asp Arg Val Thr Leu Met Gly Val Ala Ser Arg Ile Ala Val
            115                 120                 125

Asp Asp Ala Lys Leu Asp Leu Ser Val Glu Gly Arg Phe Gly
        130                 135                 140

Val Val Val Gly Ser Ala Phe Gly Gly Leu Gln Thr Leu Glu Thr Gln
145                 150                 155                 160

Ile Gln Thr Met Asn Glu Lys Gly Pro Gly Ser Val Ser Pro Phe Ala
                165                 170                 175

Val Pro Ser Leu Leu Ser Asn Leu Ile Ser Gly Val Ile Ala Leu Glu
                180                 185                 190

Asn Gly Ala Lys Gly Pro Asn Tyr Val Val Asn Ser Ala Cys Ala Ala
            195                 200                 205

Ser Thr His Ala Leu Gly Leu Ala Tyr Ala His Ile Ala His Gly Glu
        210                 215                 220

Ala Asp Val Cys Leu Ala Gly Gly Ser Glu Ala Ala Val Thr Pro Phe
225                 230                 235                 240
```

Gly Phe Ala Gly Phe Cys Ser Met Lys Ala Met Ala Thr Lys Tyr Asn
                245                 250                 255

Asp Asn Pro Ser Gln Gly Ser Arg Pro Phe Asp Lys Asp Arg Cys Gly
            260                 265                 270

Phe Val Met Gly Glu Gly Ala Gly Met Val Val Leu Glu Ser Leu Glu
        275                 280                 285

His Ala Gln Lys Arg Gly Ala His Ile Tyr Ala Glu Val Ala Gly Phe
    290                 295                 300

Gly Gln Ala Cys Asp Ala His His Ile Thr Thr Pro His Pro Glu Gly
305                 310                 315                 320

Ala Gly Leu Ala Gln Ala Ile Thr Leu Ala Leu Glu Asp Ala Gly Met
                325                 330                 335

Ala Lys Glu Asp Leu Thr Tyr Ile Asn Ala His Gly Thr Ser Thr Ala
            340                 345                 350

Tyr Asn Asp Lys Phe Glu Thr Leu Ala Val Lys Lys Ala Leu Gly Glu
        355                 360                 365

Glu Val Ala Lys Lys Met Tyr Leu Ser Ser Thr Lys Gly Ser Thr Gly
    370                 375                 380

His Thr Leu Gly Ala Ala Gly Gly Leu Glu Ala Ile Ala Thr Val Leu
385                 390                 395                 400

Ala Ile Glu Thr Lys Thr Leu Pro Pro Thr Ile Asn Tyr Glu Thr Pro
                405                 410                 415

Asp Pro Asp Cys Asp Leu Asn Val Val Pro Asn Lys Pro Ile Thr Leu
            420                 425                 430

Asn Glu Ile Thr Gly Ala Ala Ser Gln Ser Ala Gly Phe Gly Gly His
        435                 440                 445

Asp Ser Val Val Val Phe Lys Pro Phe Lys
    450                 455

<210> SEQ ID NO 59
<211> LENGTH: 1377
<212> TYPE: DNA
<213> ORGANISM: Nannochloropsis gaditana CCMP526

<400> SEQUENCE: 59
atgcggcttt cgactctcag cgtcttgggc cctgcactag gatgcgcctt cctactattc    60
gattcaagcc tggcatatct accgagctat atgcgtgggt ctaagggaca aatctatatg   120
aaggaaaaaa gtcagcgtgt cgtcgtaacg ggtcttggac ccatatccgc tgtgggtatt   180
gggaaagatg ccttctggaa agcgctgttg aagggaaaaa gtggtatcga tcgcatcagc   240
ggctttgacc cctccggcct cacttgccag attggcgccg aagtaaaaga tttcgatgcc   300
aagccttatt tcaaggatag gaagagcgca gttcgtaacg acagggtgac cttgatggga   360
gtggccgcct cgcgcattgc tgtggacgat gccaagctgg atttgtcgtc ggtggagggg   420
gaacgcttcg gggttgtggt agggtccgcg ttcgagggc ttcaaacgct gagacccag   480
attcagacca tgaacgaaaa gggtccgggc tccgtgtctc ccttcgccgt gccaagtttg   540
ttgtccaact tgatttcggg ggtgattgcg ttggaaaatg gcgcgaaagg ccccaactac   600
gtcgtgaaca gcgcctgtgc cgcgtccacc cacgccctgg ggctggccta cgcacacatt   660
gcccacggag aggcggacgt gtgcctggcg ggcgggtcgg aagcggctgt gaccccgttc   720
ggattcgcgg gcttttgctc gatgaaagca atggccacaa agtacaatga caaccccagc   780
caaggctccc gacctttcga taaggaccgt tgcggttttg tcatgggaga gggggccggg   840

```
atggtggtgc tggaaagctt ggagcatgcg cagaaacggg gcgcgcatat ttacgccgag    900
gtggcgggct ttgggcaggc gtgcgacgcc caccatatca ccactccgca ccctgaggga    960
gcgggcttgg cccaggcaat cacgttggca ttggaggacg cgggtatggc gaaagaggac   1020
ttgacctaca ttaatgccca tggcaccagc accgcctaca atgacaaatt cgagacgctg   1080
gcggtcaaga aggccttggg agaggaggtg gccaaaaaga tgtacttgtc gtcgaccaag   1140
ggatcgacgg gccacacgct gggagcggcg ggtggactgg aagcaatcgc gacagtcctg   1200
gccatagaga cgaagacact gccgcctacg atcaattacg agacgcctga cccggattgc   1260
gacctaaacg tagtgccgaa caagcccatc accctgaatg agatcacagg gccgcctct   1320
cagtccgctg gcttcggcgg gcatgactcg gtggtggtgt tcaaaccatt caaataa     1377
```

<210> SEQ ID NO 60
<211> LENGTH: 425
<212> TYPE: PRT
<213> ORGANISM: Nannochloropsis oculata NIES2145

<400> SEQUENCE: 60

```
Met Ala Asp Leu Pro Pro Leu Val Arg Lys Arg Val Val Ile Thr Gly
1               5                   10                  15

Val Gly Ala Val Ser Pro Leu Gly Trp Gly Asp Phe Trp Asn Gly
            20                  25                  30

Leu Val Glu Gly Arg Ser Gly Ile Val Arg Leu Pro Ser Trp Ala Asp
        35                  40                  45

Glu Tyr Pro Ala Arg Ile Gly Gly Leu Val Pro Asp His Phe Lys Pro
    50                  55                  60

Ser Asp Tyr Met Asn Ala Lys Glu Val Lys Arg Gln Ala Arg Phe Thr
65                  70                  75                  80

His Phe Ala Met Ala Ala Arg Met Ala Val Glu Asp Ala Lys Leu
                85                  90                  95

Asp Leu Glu Lys Val Asp Arg Ser Arg Ala Gly Cys Met Ile Gly Ser
            100                 105                 110

Gly Ile Gly Gly Val Glu Ile Phe Glu Lys Asn Cys Gly Glu Phe Asp
        115                 120                 125

Lys Lys Gly Gly Gly Leu Pro Gly Leu Lys Ala Val Ser Pro Phe Leu
    130                 135                 140

Ile Pro Ala Leu Ile Ala Asn Thr Ala Ala Gly Thr Val Ala Ile Glu
145                 150                 155                 160

Leu Gly Leu Lys Gly Pro Asn Tyr Cys Ser Val Ser Ala Cys Ala Ser
                165                 170                 175

Gly Thr His Thr Ile Gly Asp Ala Phe Phe Phe Leu Gln Asn Gly Met
            180                 185                 190

Ala Asp Val Cys Val Thr Gly Gly Thr Glu Ala Ala Ile Thr Pro Leu
        195                 200                 205

Cys Phe Ala Gly Phe Val Ala Ile Arg Ala Leu Thr Thr Ser Gly Asn
    210                 215                 220

Asp Asp Pro Thr Lys Ala Ser Lys Pro Phe Asp Lys Asn Arg Ala Gly
225                 230                 235                 240

Phe Val Met Ala Glu Gly Ala Gly Met Leu Val Leu Glu Thr Glu Glu
                245                 250                 255

His Ala Lys Ala Arg Gly Ala Thr Ile Tyr Ala Glu Leu Ala Gly Tyr
            260                 265                 270

Gly Ala Ser Cys Asp Ala His His Ile Thr Ala Pro His Pro Glu Gly
        275                 280                 285
```

```
Glu Gly Leu Ala Asn Ala Met Asn Met Ala Leu Thr Ser Ala Gly Leu
    290                 295                 300

Lys Pro Thr Asp Val Asp Tyr Ile Asn Ala His Gly Thr Ser Thr Ala
305                 310                 315                 320

Tyr Asn Asp Lys Phe Glu Thr Leu Ala Ile His Arg Val Phe Gly Glu
                325                 330                 335

His Ala Lys Lys Leu Lys Val Ser Ser Ile Lys Ser Met Thr Gly His
            340                 345                 350

Ser Leu Gly Ala Ala Gly Ala Phe Glu Ala Val Ala Cys Ala Lys Ala
        355                 360                 365

Ile Lys Glu Gly Ile Ile Pro Pro Thr Ile Asn Tyr Glu Thr Pro Asp
    370                 375                 380

Pro Asp Cys Asp Leu Asp Tyr Val Pro Asn Lys Ala Ile Lys His Asp
385                 390                 395                 400

Val Asn Val Ala Ile Ser Asp Asn Leu Gly Phe Gly Gly His Asn Ala
                405                 410                 415

Ala Leu Val Phe Lys Lys Tyr Val Ala
            420                 425

<210> SEQ ID NO 61
<211> LENGTH: 1278
<212> TYPE: DNA
<213> ORGANISM: Nannochloropsis oculata NIES2145

<400> SEQUENCE: 61
atggcggact tgcccccgct tgtccgcaag agggtggtga tcacgggtgt cggcgccgtg      60
tctcctctcg ggtggggaga cgacttctgg aacggtctcg tggagggaag gagcggcatt     120
gtccgcctcc cttcgtgggc ggacgagtac cccgcgcgaa tcgaggcctt ggtcccggat     180
cactttaagc cgagcgacta catgaatgcc aaggaggtga acgacaggc ccgcttcacc      240 catttttgcca tggcagctgc ccgtatggcc gtggaagacg ccaagctcga cctggagaag     300
gtggaccgct cgcgtgccgg gtgcatgata ggatccggca ttggtggtgt agaaatcttc     360
gagaaaaact gtggggaatt cgacaagaag gcgagggc tccctggcct caaggctgtc       420
tcccccttcc tgattccggc cctcatcgcc acaccgcag ccgggacagt ggctattgaa      480
ctcggcttga agggcccgaa ctactgctct gtctccgcct cgcctcgg cacgcatacc        540 atcggtgatg ccttcttctt cctccaaaac ggcatggcgg acgtttgtgt aacgggcggg     600
acggaagccg ccatcacccc cctctgtttt gcgggatttg tcgccattcg cgcccttacc    660
accagtggca acgacgaccc caccaaggcc tccaagccgt tcgacaagaa ccgagccggt     720
ttcgttatgg ccgagggagc ggggatgctc gtccttgaga cggaggaaca cgcgaaggcc     780
cgaggtgcca ccatctatgc cgagcttgct ggctacggcg catcctgcga cgcccaccac    840
atcaccgccc ccatcccga aggcgagggg ctggcgaacg cgatgaatat ggctctgacg     900
tccgccggcc tcaagcctac ggacgtggac tacattaatg cccatggaac cagcacggcc    960
tacaacgaca aattcgagac gctggccatt caccgcgtct ttggcgagca cgccaagaag   1020
ctgaaggttt cttccatcaa gtcaatgact ggtcactccc tcggggccgc cggtgccttc    1080
gaggccgtgg cgtgcgcgaa ggcaatcaag gagggcatca tcccgcccac catcaactac   1140
gagactcccg atccagactg cgacttggac tatgttccca acaaggcgat caagcacgac   1200
gtgaatgtgg ccatctccga taacctgggc ttcggcgggc acaacgcggc tttggtcttc    1260
aagaagtatg ttgcctag                                                  1278
```

<210> SEQ ID NO 62
<211> LENGTH: 406
<212> TYPE: PRT
<213> ORGANISM: Escherichia coli

<400> SEQUENCE: 62

Met Lys Arg Ala Val Ile Thr Gly Leu Gly Ile Val Ser Ser Ile Gly
1               5                   10                  15

Asn Asn Gln Gln Glu Val Leu Ala Ser Leu Arg Glu Gly Arg Ser Gly
            20                  25                  30

Ile Thr Phe Ser Gln Glu Leu Lys Asp Ser Gly Met Arg Ser His Val
        35                  40                  45

Trp Gly Asn Val Lys Leu Asp Thr Thr Gly Leu Ile Asp Arg Lys Val
    50                  55                  60

Val Arg Phe Met Ser Asp Ala Ser Ile Tyr Ala Phe Leu Ser Met Glu
65                  70                  75                  80

Gln Ala Ile Ala Asp Ala Gly Leu Ser Pro Glu Ala Tyr Gln Asn Asn
                85                  90                  95

Pro Arg Val Gly Leu Ile Ala Gly Ser Gly Gly Gly Ser Pro Arg Phe
            100                 105                 110

Gln Val Phe Gly Ala Asp Ala Met Arg Gly Pro Arg Gly Leu Lys Ala
        115                 120                 125

Val Gly Pro Tyr Val Val Thr Lys Ala Met Ala Ser Gly Val Ser Ala
    130                 135                 140

Cys Leu Ala Thr Pro Phe Lys Ile His Gly Val Asn Tyr Ser Ile Ser
145                 150                 155                 160

Ser Ala Cys Ala Thr Ser Ala His Cys Ile Gly Asn Ala Val Glu Gln
                165                 170                 175

Ile Gln Leu Gly Lys Gln Asp Ile Val Phe Ala Gly Gly Gly Glu Glu
            180                 185                 190

Leu Cys Trp Glu Met Ala Cys Glu Phe Asp Ala Met Gly Ala Leu Ser
        195                 200                 205

Thr Lys Tyr Asn Asp Thr Pro Glu Lys Ala Ser Arg Thr Tyr Asp Ala
    210                 215                 220

His Arg Asp Gly Phe Val Ile Ala Gly Gly Gly Met Val Val Val
225                 230                 235                 240

Glu Glu Leu Glu His Ala Leu Ala Arg Gly Ala His Ile Tyr Ala Glu
                245                 250                 255

Ile Val Gly Tyr Gly Ala Thr Ser Asp Gly Ala Asp Met Val Ala Pro
            260                 265                 270

Ser Gly Glu Gly Ala Val Arg Cys Met Lys Met Ala Met His Gly Val
        275                 280                 285

Asp Thr Pro Ile Asp Tyr Leu Asn Ser His Gly Thr Ser Thr Pro Val
    290                 295                 300

Gly Asp Val Lys Glu Leu Ala Ala Ile Arg Glu Val Phe Gly Asp Lys
305                 310                 315                 320

Ser Pro Ala Ile Ser Ala Thr Lys Ala Met Thr Gly His Ser Leu Gly
                325                 330                 335

Ala Ala Gly Val Gln Glu Ala Ile Tyr Ser Leu Leu Met Leu Glu His
            340                 345                 350

Gly Phe Ile Ala Pro Ser Ile Asn Ile Glu Glu Leu Asp Glu Gln Ala
        355                 360                 365

Ala Gly Leu Asn Ile Val Thr Glu Thr Thr Asp Arg Glu Leu Thr Thr

```
             370                375                380
Val Met Ser Asn Ser Phe Gly Phe Gly Gly Thr Asn Ala Thr Leu Val
385                390                395                400

Met Arg Lys Leu Lys Asp
                405
```

<210> SEQ ID NO 63
<211> LENGTH: 1221
<212> TYPE: DNA
<213> ORGANISM: Escherichia coli

<400> SEQUENCE: 63

```
atgaaacgtg cagtgattac tggcctgggc attgtttcca gcatcggtaa taaccagcag    60
gaagtcctgg catctctgcg tgaaggacgt tcagggatca ctttctctca ggagctgaag   120
gattccggca tgcgtagcca cgtctggggc aacgtaaaac tggataccac tggcctcatt   180
gaccgcaaag ttgtgcgctt tatgagcgac gcatccattt atgcattcct ttctatggag   240
caggcaatcg ctgatgcggg cctctctccg gaagcttacc agaataaccc cgcgttggc    300
ctgattgcag gttccggcgg cggctccccg cgtttccagg tgttcggcgc tgacgcaatg   360
cgcggcccgc gcggcctgaa agcggttggc ccgtatgtgg tcaccaaagc gatggcatcc   420
ggcgtttctg cctgcctcgc caccccgttt aaaattcatg gcgttaacta ctccatcagc   480
tccgcgtgtg cgacttccgc acactgtatc ggtaacgcag tagagcagat ccaactgggc   540
aaacaggaca tcgtgtttgc tggcggcggc gaagagctgt gctgggaaat ggcttgcgaa   600
ttcgacgcaa tgggtgcgct gtctactaaa tacaacgaca ccccggaaaa agcctcccgt   660
acttacgacg ctcaccgtga cggtttcgtt atcgctggcg gcggcggtat ggtagtggtt   720
gaagagctgg aacacgcgct ggcgcgtggt gctcacatct atgctgaaat cgttggctac   780
ggcgcaacct ctgatggtgc agacatggtt gctccgtctg cgaaggcgc agtacgctgc   840
atgaagatgg cgatgcatgg cgttgatacc ccaatcgatt acctgaactc ccacggtact   900
tcgactccgg ttggcgacgt gaaagagctg gcagctatcc gtgaagtgtt cggcgataag   960
agcccggcga tttctgcaac caaagccatg accggtcact ctctgggcgc tgctggcgta  1020
caggaagcta tctactctct gctgatgctg aacacggct tcatcgcccc gagcatcaac  1080
attgaagagc tggacgagca ggctgcaggt ctgaacatcg tgaccgaaac gaccgatcgc  1140
gaactgacca ccgttatgtc taacagcttc ggcttcggcg gcaccaacgc cacgctggta  1200
atgcgcaagc tgaaagatta a                                            1221
```

<210> SEQ ID NO 64
<211> LENGTH: 413
<212> TYPE: PRT
<213> ORGANISM: Escherichia coli

<400> SEQUENCE: 64

```
Met Ser Lys Arg Arg Val Val Thr Gly Leu Gly Met Leu Ser Pro
1               5                  10                  15

Val Gly Asn Thr Val Glu Ser Thr Trp Lys Ala Leu Leu Ala Gly Gln
                20                  25                  30

Ser Gly Ile Ser Leu Ile Asp His Phe Asp Thr Ser Ala Tyr Ala Thr
            35                  40                  45

Lys Phe Ala Gly Leu Val Lys Asp Phe Asn Cys Glu Asp Ile Ile Ser
        50                  55                  60

Arg Lys Glu Gln Arg Lys Met Asp Ala Phe Ile Gln Tyr Gly Ile Val
```

```
            65                  70                  75                  80
Ala Gly Val Gln Ala Met Gln Asp Ser Gly Leu Glu Ile Thr Glu Glu
                    85                  90                  95

Asn Ala Thr Arg Ile Gly Ala Ala Ile Gly Ser Gly Ile Gly Gly Leu
                100                 105                 110

Gly Leu Ile Glu Glu Asn His Thr Ser Leu Met Asn Gly Gly Pro Arg
                115                 120                 125

Lys Ile Ser Pro Phe Phe Val Pro Ser Thr Ile Val Asn Met Val Ala
130                 135                 140

Gly His Leu Thr Ile Met Tyr Gly Leu Arg Gly Pro Ser Ile Ser Ile
145                 150                 155                 160

Ala Thr Ala Cys Thr Ser Gly Val His Asn Ile Gly His Ala Ala Arg
                165                 170                 175

Ile Ile Ala Tyr Gly Asp Ala Asp Val Met Val Ala Gly Gly Ala Glu
                180                 185                 190

Lys Ala Ser Thr Pro Leu Gly Val Gly Gly Phe Gly Ala Ala Arg Ala
                195                 200                 205

Leu Ser Thr Arg Asn Asp Asn Pro Gln Ala Ala Ser Arg Pro Trp Asp
210                 215                 220

Lys Glu Arg Asp Gly Phe Val Leu Gly Asp Gly Ala Gly Met Leu Val
225                 230                 235                 240

Leu Glu Glu Tyr Glu His Ala Lys Lys Arg Gly Ala Lys Ile Tyr Ala
                245                 250                 255

Glu Leu Val Gly Phe Gly Met Ser Ser Asp Ala Tyr His Met Thr Ser
                260                 265                 270

Pro Pro Glu Asn Gly Ala Gly Ala Ala Leu Ala Met Ala Asn Ala Leu
                275                 280                 285

Arg Asp Ala Gly Ile Glu Ala Ser Gln Ile Gly Tyr Val Asn Ala His
290                 295                 300

Gly Thr Ser Thr Pro Ala Gly Asp Lys Ala Glu Ala Gln Ala Val Lys
305                 310                 315                 320

Thr Ile Phe Gly Glu Ala Ala Ser Arg Val Leu Val Ser Ser Thr Lys
                325                 330                 335

Ser Met Thr Gly His Leu Leu Gly Ala Ala Gly Ala Val Glu Ser Ile
                340                 345                 350

Tyr Ser Ile Leu Ala Leu Arg Asp Gln Ala Val Pro Pro Thr Ile Asn
                355                 360                 365

Leu Asp Asn Pro Asp Glu Gly Cys Asp Leu Asp Phe Val Pro His Glu
370                 375                 380

Ala Arg Gln Val Ser Gly Met Glu Tyr Thr Leu Cys Asn Ser Phe Gly
385                 390                 395                 400

Phe Gly Gly Thr Asn Gly Ser Leu Ile Phe Lys Lys Ile
                405                 410

<210> SEQ ID NO 65
<211> LENGTH: 1242
<212> TYPE: DNA
<213> ORGANISM: Escherichia coli

<400> SEQUENCE: 65
atgtctaagc gtcgtgtagt tgtgaccgga ctgggcatgt tgtctcctgt cggcaatacc     60
gtagagtcta cctggaaagc tctgcttgcc ggtcagagtg gcatcagcct aatcgaccat    120
ttcgatacta gcgcctatgc aacgaaattt gctggcttag taaaggattt taactgtgag    180
```

-continued

| | | |
|---|---|---|
| gacattatct cgcgcaaaga acagcgcaag atgatgcct tcattcaata tggaattgtc | 240 | |
| gctggcgttc aggccatgca ggattctggc cttgaaataa cggaagagaa cgcaacccgc | 300 | |
| attggtgccg caattggctc cgggattggc ggcctcggac tgatcgaaga aaaccacaca | 360 | |
| tctctgatga acgtggtcc acgtaagatc agcccattct tcgttccgtc aacgattgtg | 420 | |
| aacatggtgg caggtcatct gactatcatg tatggcctgc gtggcccgag catctctatc | 480 | |
| gcgactgcct gtacttccgg cgtgcacaac attggccatg ctgcgcgtat tatcgcgtat | 540 | |
| ggcgatgctg acgtgatggt tgcaggtggc gcagagaaag ccagtacgcc gctgggcgtt | 600 | |
| ggtggttttg gcgcggcacg tgcattatct acccgcaatg ataacccgca agcggcgagc | 660 | |
| cgcccgtggg ataaagagcg tgatggtttc gtactgggcg atggtgccgg tatgctggta | 720 | |
| cttgaagagt acgaacacgc gaaaaaacgc ggtgcgaaaa tttacgctga actcgtcggc | 780 | |
| tttggtatga gcagcgatgc ttatcatatg acgtcaccgc cagaaaatgg cgcaggcgca | 840 | |
| gctctggcga tggcaaatgc tctgcgtgat gcaggcattg aagcgagtca gattggctac | 900 | |
| gttaacgcgc acggtacttc tacgccggct ggcgataaag ctgaagcgca ggcggtgaaa | 960 | |
| accatcttcg gtgaagctgc aagccgtgtg ttggtaagct ccacgaaatc tatgaccggt | 1020 | |
| cacctgttag gtgcggcggg tgcagtagaa tctatctact ccatcctggc gctgcgcgat | 1080 | |
| caggctgttc cgccaaccat caacctggat aacccggatg aaggttgcga tctggatttc | 1140 | |
| gtaccgcacg aagcgcgtca ggttagcgga atggaataca ctctgtgtaa ctccttcggc | 1200 | |
| ttcggtggca ctaatggttc tttgatcttt aaaaagatct aa | 1242 | |

<210> SEQ ID NO 66
<211> LENGTH: 35
<212> TYPE: DNA
<213> ORGANISM: Artificial Sequence
<220> FEATURE:
<223> OTHER INFORMATION: PCR primer 1 for NoTE

<400> SEQUENCE: 66
gcggccgctc tagagatgac gcctttggcc ttcac         35

<210> SEQ ID NO 67
<211> LENGTH: 39
<212> TYPE: DNA
<213> ORGANISM: Artificial Sequence
<220> FEATURE:
<223> OTHER INFORMATION: PCR primer 2 for NoTE

<400> SEQUENCE: 67
tgcttctttc attagctagc taatatcaat tttctttgg     39

<210> SEQ ID NO 68
<211> LENGTH: 20
<212> TYPE: DNA
<213> ORGANISM: Artificial Sequence
<220> FEATURE:
<223> OTHER INFORMATION: PCR primer 1 for pBluescriptII

<400> SEQUENCE: 68
ctctagagcg gccgccaccg              20

<210> SEQ ID NO 69
<211> LENGTH: 24
<212> TYPE: DNA
<213> ORGANISM: Artificial Sequence
<220> FEATURE:
<223> OTHER INFORMATION: PCR primer 2 for pBluescriptII

<400> SEQUENCE: 69
gcgttaatat tttgttaaaa ttcg        24

<210> SEQ ID NO 70
<211> LENGTH: 532
<212> TYPE: PRT
<213> ORGANISM: Cuphea lanceolata

<400> SEQUENCE: 70

```
Met Ala Ala Ser Pro Phe Cys Thr Trp Leu Val Ala Ala Cys Met Ser
1               5                   10                  15

Thr Ser Phe Glu Asn Asn Pro Arg Ser Pro Ser Ile Lys Arg Leu Pro
            20                  25                  30

Arg Arg Arg Arg Val Leu Ser His Cys Ser Leu Arg Gly Ser Thr Phe
        35                  40                  45

Gln Cys Leu Val Thr Ser His Ile Asp Pro Cys Asn Gln Asn Cys Ser
    50                  55                  60

Ser Asp Ser Leu Ser Phe Ile Gly Val Asn Gly Phe Gly Ser Lys Pro
65                  70                  75                  80

Phe Arg Ser Asn Arg Gly His Arg Leu Gly Arg Ala Ser His Ser
            85                  90                  95

Gly Glu Ala Met Ala Val Ala Leu Gln Pro Ala Gln Glu Val Ala Thr
            100                 105                 110

Lys Lys Lys Pro Ala Ile Lys Gln Arg Arg Val Val Thr Gly Met
        115                 120                 125

Gly Val Val Thr Pro Leu Gly His Glu Pro Asp Val Phe Tyr Asn Asn
    130                 135                 140

Leu Leu Asp Gly Val Ser Gly Ile Ser Glu Ile Glu Asn Phe Asp Ser
145                 150                 155                 160

Thr Gln Phe Pro Thr Arg Ile Ala Gly Glu Ile Lys Ser Phe Ser Thr
            165                 170                 175

Asp Gly Trp Val Ala Pro Lys Leu Ser Lys Arg Met Asp Lys Leu Met
            180                 185                 190

Leu Tyr Leu Leu Thr Ala Gly Lys Lys Ala Leu Ala Asp Ala Gly Ile
        195                 200                 205

Thr Asp Asp Val Met Lys Glu Leu Asp Lys Arg Lys Cys Gly Val Leu
    210                 215                 220

Ile Gly Ser Gly Met Gly Gly Met Lys Leu Phe Tyr Asp Ala Leu Glu
225                 230                 235                 240

Ala Leu Lys Ile Ser Tyr Arg Lys Met Asn Pro Phe Cys Val Pro Phe
            245                 250                 255

Ala Thr Thr Asn Met Gly Ser Ala Met Leu Ala Met Asp Leu Gly Trp
            260                 265                 270

Met Gly Pro Asn Tyr Ser Ile Ser Thr Ala Cys Ala Thr Ser Asn Phe
        275                 280                 285

Cys Ile Leu Asn Ala Ala Asn His Ile Ile Arg Gly Glu Ala Asp Met
    290                 295                 300

Met Leu Cys Gly Gly Ser Asp Ala Val Ile Ile Pro Ile Gly Leu Gly
305                 310                 315                 320

Gly Phe Val Ala Cys Arg Ala Leu Ser Gln Arg Asn Asn Asp Pro Thr
            325                 330                 335

Lys Ala Ser Arg Pro Trp Asp Ser Asn Arg Asp Gly Phe Val Met Gly
            340                 345                 350
```

Glu Gly Ala Gly Val Leu Leu Glu Glu Leu Glu His Ala Lys Lys
                355                 360                 365

Arg Gly Ala Thr Ile Tyr Ala Glu Phe Leu Gly Ser Phe Thr Cys
        370                 375                 380

Asp Ala Tyr His Met Thr Glu Pro His Pro Glu Gly Ala Gly Val Ile
385                 390                 395                 400

Leu Cys Ile Glu Lys Ala Met Ala Gln Ala Gly Val Ser Arg Glu Asp
                405                 410                 415

Val Asn Tyr Ile Asn Ala His Ala Thr Ser Thr Pro Ala Gly Asp Ile
                420                 425                 430

Lys Glu Tyr Gln Ala Leu Ala His Cys Phe Gly Gln Asn Ser Glu Leu
            435                 440                 445

Arg Val Asn Ser Thr Lys Ser Met Ile Gly His Leu Leu Gly Ala Ala
        450                 455                 460

Gly Gly Val Glu Ala Val Thr Val Ile Gln Ala Ile Arg Thr Gly Trp
465                 470                 475                 480

Ile His Pro Asn Leu Asn Leu Glu Asp Pro Asp Lys Ala Val Asp Ala
                485                 490                 495

Lys Phe Leu Val Gly Pro Glu Lys Glu Arg Leu Asn Val Lys Val Gly
            500                 505                 510

Leu Ser Asn Ser Phe Gly Phe Gly Gly His Asn Ser Ser Ile Leu Phe
        515                 520                 525

Ala Pro Tyr Asn
    530

<210> SEQ ID NO 71
<211> LENGTH: 1599
<212> TYPE: DNA
<213> ORGANISM: Cuphea lanceolata

<400> SEQUENCE: 71
atggctgcgt caccgttctg tacgtggctc gtagctgctt gcatgtccac ttccttcgaa      60
aacaacccac gttcgccctc catcaagcgt ctcccccgcc ggaggagggt tctctcccat     120
tgctccctcc gtggatccac cttccaatgc ctcgtcacct cacacatcga cccttgcaat     180
cagaactgct cctccgactc ccttagcttc atcggggtta acggattcgg atccaagcca     240
ttccggtcca atcgcggcca ccggaggctc ggccgtgctt cccattccgg ggaggccatg     300
gctgtggctc tgcaacctgc acaggaagtc gccacgaaga gaaacctgc tatcaagcaa      360 aggcgagtag ttgttacagg aatgggtgtg gtgactcctc taggccatga acctgatgtt     420
ttctacaaca atctcctaga tggagtaagc ggcataagtg agatagagaa cttcgacagc     480
actcagtttc ccacgagaat tgccggagag atcaagtctt tttccacaga tggctgggtg     540
gccccaaagc tctccaagag gatggacaag ctcatgcttt acttgttgac tgctggcaag     600
aaagcattag cagatgctgg aatcaccgat gatgtgatga agagcttga taaaagaaag      660 tgtggagttc tcattggctc cggaatgggc ggcatgaagt tgttctacga tgcgcttgaa     720
gccctgaaaa tctcttacag gaagatgaac ccttttttgtg taccttttgc caccacaaat     780
atgggatcag ctatgcttgc aatggatctg gatggatgg gtccaaacta ctctatttca      840 actgctgtg caacaagtaa tttctgtata ctgaatgctg caaccacat aatcagaggc       900 gaagctgaca tgatgctttg tggtggctcg gatgcggtca ttatacctat cggtttggga     960
ggttttgtgg cgtgccgagc tttgtcacag aggaataatg accctaccaa agcttcgaga    1020
ccatgggata gtaatcgtga tggatttgta atgggcgaag agctggagt gttacttctc    1080

```
gaggagttag agcatgcaaa gaaaagaggt gcaaccattt atgcagaatt tttaggggc    1140 agtttcactt gcgatgccta ccacatgacc gagcctcacc ctgaaggagc tggagtgatc    1200
ctctgcatag agaaggccat ggctcaggcc ggagtctcta gagaagatgt aaattacata    1260
aatgcccatg caacttccac tcctgctgga gatatcaaag aataccaagc tctcgcccac    1320
tgtttcggcc aaaacagcga gctgagagtg aattccacta atcgatgat cggtcatctt     1380 cttgagcag ctggtggcgt agaagcagtt actgtaattc aggcgataag gactgggtgg     1440
atccatccaa atcttaattt ggaagacccg gacaaagccg tggatgcaaa atttctcgtg    1500
ggacctgaga aggagagact gaatgtcaag gtcggtttgt ccaattcatt tgggttcggt    1560
gggcataact cgtctatact cttcgcccct tacaattag                           1599
```

<210> SEQ ID NO 72
<211> LENGTH: 35
<212> TYPE: DNA
<213> ORGANISM: Artificial Sequence
<220> FEATURE:
<223> OTHER INFORMATION: PCR primer 1 for C1KASIV

<400> SEQUENCE: 72

```
aaatcataca gcaggatggc ggcggcctct tccat                               35
```

<210> SEQ ID NO 73
<211> LENGTH: 35
<212> TYPE: DNA
<213> ORGANISM: Artificial Sequence
<220> FEATURE:
<223> OTHER INFORMATION: PCR primer 2 for C1KASIV

<400> SEQUENCE: 73

```
ctcttccaca gaagcctaat tgtaagggc gaaga                                35
```

<210> SEQ ID NO 74
<211> LENGTH: 1747
<212> TYPE: DNA
<213> ORGANISM: Brassica rapa

<400> SEQUENCE: 74

```
gatatcacta caatgtcgga gagacaaggc tgcgccagca tatacaaaag ggaaatgaag    60
atggcctttt gattagctgt gtagcatcag cagctaatct ctgggctctc atcatggatg    120
ctggaactgg attcacttct caagtttatg agttgtcacc ggtcttccta cacaaggtaa    180
taatcagttg aagcaattaa gaatcaattt gatttgtagt aaactaagaa gaacttacct    240
tatgttttcc ccgcaggact ggattatgga caatgggaa aagaactact atataagctc     300
catagctggt tcagataacg ggagctcttt agttgttatg tcaaaaggtt agtgtttagt    360
gaataataaa cttataccac aaagtcttca ttgacttatt tatatacttg ttgtgaattg    420
ctaggaacta cttattctca gcagtcatac aaagtgagtg actcatttcc gttcaagtgg    480
ataaataaga aatggaaaga agattttcat gtaacctcca tgacaactgc tggtaatcgt    540
tggggtgtgg taatgtcgag gaactctggc ttctctgatc aggtaggttt ttgtctctta    600
tggtctgggg gtttttattt cccctgatag tctaatatga taaactctgc gttgtgaaag    660
gtggtggagc ttgactttt gtacccaagc gatgggatac ataggaggtg ggagaatggg    720
tatagaataa catcaatggc agcaactgcg gatcaagcag ctttcatatt aagcatacca    780
aagcgtaaga tggtggatga aactcaagag actctccgca ccaccgcctt tccaagtact    840
```

```
catgtcaagg ttggtttctt tagctttgaa cacagatttg gatctttttg ttttgtttcc      900
atatacttag gacctgagag cttttggttg attttttttt caggacaaat gggcgaagaa      960
tctgtacatt gcatcaatat gctatggcag gacagtgtgc tgatacacac ttaagcatca     1020
tgtggaaagc caaagacaat tggagcgaga ctcagggtcg tcataatacc aatcaaagac     1080
gtaaaaccag acgcaaccte tttggttgaa tgtaatgaaa gggatgtgtc ttggtatgta     1140
tgtacgaata acaaaagaga agatggaatt agtagtagaa atatttggga gcttttaag      1200 cccttcaagt gtgcttttta tcttattgat atcatccatt tgcgttgttt aatgcgtctc     1260
tagatatgtt cctatatctt tctcagtgtc tgataagtga atgtgagaa accatacca       1320 aaccaaaata ttcaaatctt atttttaata atgttgaatc actcggagtt gccaccttct     1380
gtgccaattg tgctgaatct atcacactag aaaaaaacat ttcttcaagg taatgacttg     1440
tggactatgt tctgaattct cattaagttt ttattttctg aagtttaagt ttttaccttc     1500
tgttttgaaa tatatcgttc ataagatgtc acgccaggac atgagctaca catcgcacat     1560
agcatgcaga tcaggacgat ttgtcactca cttcaaacac ctaagagctt ctctctcaca     1620
gcgcacacac atatgcatgc aatatttaca cgtgatcgcc atgcaaatct ccattctcac     1680
ctataaatta gagcctcggc ttcactcttt actcaaacca aaactcatca ctacagaaca     1740
tacacaa                                                               1747

<210> SEQ ID NO 75
<211> LENGTH: 1255
<212> TYPE: DNA
<213> ORGANISM: Brassica rapa

<400> SEQUENCE: 75
gtgtgtatac cacggtgata tgagtgtggt tgttgatgta tgttaacact acatagtcat       60
ggtgtgtgtt ccataaataa tgtactaatg taataagaac tactccgtag acggtaataa      120
aagagaagtt ttttttttta ctcttgctac tttcctataa agtgatgatt aacaacagat      180
acaccaaaaa gaaacaatt aatctatatt cacaatgaag cagtactagt ctattgaaca      240
tgtcagattt tcttttttcta aatgtctaat taagccttca aggctagtga tgataaaaga     300
tcatccaatg ggatccaaca aagactcaaa tctggttttg atcagatact tcaaaactat      360
ttttgtattc attaaattat gcaagtgttc tttttatttgg tgaagactct ttagaagcaa     420
agaacgacaa gcagtaataa aaaaaacaaa gttcagtttt aagatttgtt attgacttat      480
tgtcatttga aaatatagt atgatattaa tatgttttta tttatataat gcttgtctat       540
tcaagatttg agaacattaa tatgatactg tccacatatc aatatatta agtttcattt       600 ctgttcaaac atatgataga tggtcaaatg attatgagtt tgttattta cctgaagaaa       660 gataagtgag cttcgagttt ctgaagggta cgtgatcttc atttcttggc taaaagcgaa     720
tatgacatca cctagagaaa gccgataata gtaaactctg ttcttggttt ttggtttaat     780
caaaccgaac cggtagctga gtgtcaagtc agcaaacatc gcaaaccata tgtcaattcg     840
ttagattccc ggtttaagtt gtaaaccggt atttcatttg gtgaaaaccc tagaagccag     900 ccacccttt taatctaatt tttgtaaacg agaagtcacc acacctctcc actaaaaccc      960
tgaaccttac tgagagaagc agagcgcagc tcaaagaaca aataaaaccc gaagatgaga    1020
ccaccacgtg gcggcgggag cttcagggga cggggaggaa gagatggcgg cggacgcttt    1080
ggtggcggcg gcgacgtttt tggtggcggc ggtggacgct tggtggcggc ggtggacgc     1140 tttggtggtg gtggatatcg tgacgaaggg cctcccagcg aagtcattgg ttcgtttact    1200
```

```
ctttacttag tcgaatctta ttcttgctct gctcgttgtt ttaccgataa agctt          1255

<210> SEQ ID NO 76
<211> LENGTH: 1167
<212> TYPE: DNA
<213> ORGANISM: Artificial Sequence
<220> FEATURE:
<223> OTHER INFORMATION: BTE chloroplast transit signal and CTE

<400> SEQUENCE: 76
atggccacca cctctttagc ttccgctttc tgctcgatga agctgtaat gttggctcgt       60 gatggccggg gcatgaaacc caggagcagt gatttgcagc tgagggcggg aaatgcgcca     120
acctctttga agatgatcaa tggaccaag ttcagttaca cggagagctt gaaaaggttg      180
cctgactgga gcatgctctt tgcagtgatc acaaccatct tttcggctgc tgagaagcag    240
tggaccaatc tagagctcga ttccaagaag agggggggccg acgcggtcgc agatgcctct    300
ggggtcggga gatggtcaa gaatggactt gtttacaggc agaattttc tatccggtcc       360 tacgaaatcg gggttgataa acgtgcttcg gtagaggcat tgatgaatca tttccaggaa    420
acgtcgctta accattgcaa gtgtattggc cttatgcatg gcggctttgg ttgtacacca    480
gagatgactc gaagaaatct gatatgggtt gttgccaaaa tgctggttca tgtcgaacgt    540
tatccttggt ggggagacgt ggttcaaata aatacgtgga ttagttcatc tggaaagaat    600
ggtatgggac gtgattggca tgttcatgac tgccaaactg gcctaccat atgaggggt      660 accagtgtct gggtcatgat ggataaacac acgaggagac tgtctaaact tcctgaagaa    720
gttagagcag agataacccc tttcttttca gagcgtgatg ctgttttgga cgataacggc    780
agaaaacttc ccaagttcga tgatgattct gcagctcatg ttcgaagggg cttgactcct    840
cgttggcatg atttcgatgt aaatcagcat gtgaacaatg tcaaatacgt cggctggatt    900
cttgagagcg ttcctgtgtg gatgttggat ggctacgagg ttgcaaccat gagtctggaa    960
taccggaggg agtgtaggat ggatagtgtg gtgcagtctc tcaccgccgt ctcttccgac   1020
cacgccgacg gctccccccat cgtgtgccag catcttctgc ggctcgagga tgggactgag  1080
attgtgaggg gtcaaacaga atggaggcct aagcagcagg cttgtgatct tgggaacatg  1140
ggtctgcacc caactgagag taaatga                                       1167

<210> SEQ ID NO 77
<211> LENGTH: 836
<212> TYPE: DNA
<213> ORGANISM: Streptomyces

<400> SEQUENCE: 77
atgagcccag aacgacgccc ggccgacatc cgccgtgcca ccgaggcgga catgccggcg     60
gtctgcacca tcgtcaacca ctacatcgag acaagcacgg tcaacttccg taccgagccg    120
caggaaccgc aggagtggac ggacgacctc gtccgtctgc gggagcgcta tccctggctc    180
gtcgccgagg tggacggcga gtcgccggc atcgcctacg cgggcccctg gaaggcacgc    240
aacgcctacg actggacggc cgagtcgacc gtgtacgtct cccccgcca ccagcggacg    300 ggactgggct ccacgctcta caccaccctg ctgaagtccc tggaggcaca gggcttcaag    360
agcgtggtcg ctgtcatcgg gctgcccaac gacccgagcg tgcgcatgca cgaggcgctc    420
ggatatgccc ccgcggcat gctgcggcg gccggcttca gcacgggaa ctggcatgac    480 gtgggtttct ggcagctgga cttcagcctg ccggtaccgc ccgtccggt cctgccgtc    540
```

```
accgagatct gatgacccgg gtaccgagct cgaatttccc cgatcgttca acatttggc     600 aataaagttt cttaagattg aatcctgttg ccggtcttgc gatgattatc atataatttc    660
tgttgaatta cgttaagcat gtaataatta acatgtaatg catgacgtta tttatgagat    720
gggtttttat gattagagtc ccgcaattat acatttaata cgcgatagaa acaaaatat    780 agcgcgcaaa ctaggataaa ttatcgcgcg cggtgtcatc tatgttacta gatcgg       836
```

<210> SEQ ID NO 78
<211> LENGTH: 1720
<212> TYPE: DNA
<213> ORGANISM: Brassica napus

<400> SEQUENCE: 78

```
taccgagggg aatttatgga acgtcagtgg agcatttttg acaagaaata tttgctagct    60
gatagtgacc ttaggcgact tttgaacgcg caataatggt ttctgacgta tgtgcttagc   120
tcattaaact ccagaaaccc gcggctgagt ggctccttca acgttgcggt tctgtcagtt   180
ccaaacgtaa aacggcttgt cccgcgtcat cggcgggggt cataacgtga ctcccttaat   240
tctccgctca tgatcttgat cccctgcgcc atcagatcct tggcggcaag aaagccatcc   300
agtttacttt gcagggcttc ccaaccttac cagagggcgc cccagctggc aattccggtt   360
cgcttgctgt ccataaaacc gcccagtcta gctatcgcca tgtaagccca ctgcaagcta   420
cctgctttct ctttgcgctt gcgttttccc ttgtccagat agcccagtag ctgacattca   480
tccggggtca gcaccgtttc tgcggactgg cttttctacgt gttccgcttc ctttagcagc   540
ccttgcgccc tgagtgcttg cggcagcgtg aagctttctt catcggtgat tgattccttt   600
aaagacttat gtttcttatc ttgcttctga ggcaagtatt cagttaccag ttaccactta   660
tattctggac tttctgactg catcctcatt tttccaacat tttaaatttc actattggct   720
gaatgcttct tctttgagga agaaacaatt cagatggcag aaatgtatca accaatgcat   780
atatacaaat gtacctcttg ttctcaaaac atctatcgga tggttccatt tgctttgtca   840
tccaattagt gactacttta tattattcac tcctctttat tactatttc atgcgaggtt    900 gccatgtaca ttatatttgt aaggattgac gctattgagc gttttcttc aattttcttt    960 attttagaca tgggtatgaa atgtgtgtta gagttgggtt gaatgagata tacgttcaag  1020
tgaatggcat accgttctcg agtaaggatg acctacccat tcttgagaca atgttacat  1080 tttagtatca gagtaaaatg tgtacctata actcaaattc gattgacatg tatccattca  1140
acataaaatt aaaccagcct gcacctgcat ccacatttca agtattttca aaccgttcgg  1200
ctcctatcca ccgggtgtaa caagacggat tccgaatttg gaagattttg actcaaattc  1260
ccaatttata ttgaccgtga ctaaatcaac tttaacttct ataattctga ttaagctccc  1320
aatttatatt cccaacggca ctacctccaa aatttataga ctctcatccc cttttaaacc  1380
aacttagtaa acgttttttt ttttaatttt atgaagttaa gttttttacct tgtttttaaa  1440 aagaatcgtt cataagatgc catgccagaa cattagctac acgttacaca tagcatgcag  1500
ccgcggagaa ttgttttttct tcgccacttg tcactcccctt caaacaccta agagcttctc  1560
tctcacagca cacacataca atcacatgcg tgcatgcatt attacacgtg atcgccatgc  1620
aaatctcctt tatagcctat aaattaactc atccgcttca ctctttactc aaaccaaaac  1680
tcatcaatac aaacaagatt aaaaacatac acgaggatcc                        1720
```

<210> SEQ ID NO 79
<211> LENGTH: 33

```
<212> TYPE: DNA
<213> ORGANISM: Artificial Sequence
<220> FEATURE:
<223> OTHER INFORMATION: PCR primer 1 for Arabidopsis thaliana
      transformation

<400> SEQUENCE: 79
atatatatat actagtatga gcccagaacg acg                              33

<210> SEQ ID NO 80
<211> LENGTH: 37
<212> TYPE: DNA
<213> ORGANISM: Artificial Sequence
<220> FEATURE:
<223> OTHER INFORMATION: PCR primer 2 for Arabidopsis thaliana
      transformation

<400> SEQUENCE: 80
atatatatat catatgatca gatctcggtg acgggca                          37

<210> SEQ ID NO 81
<211> LENGTH: 36
<212> TYPE: DNA
<213> ORGANISM: Artificial Sequence
<220> FEATURE:
<223> OTHER INFORMATION: PCR primer 3 for Arabidopsis thaliana
      transformation

<400> SEQUENCE: 81
tgacgagttc catatggcgg gactctgggg ttcgaa                           36

<210> SEQ ID NO 82
<211> LENGTH: 37
<212> TYPE: DNA
<213> ORGANISM: Artificial Sequence
<220> FEATURE:
<223> OTHER INFORMATION: PCR primer 4 for Arabidopsis thaliana
      transformation

<400> SEQUENCE: 82
catcttgttc actagtgcga aacgatccag atccggt                          37

<210> SEQ ID NO 83
<211> LENGTH: 32
<212> TYPE: DNA
<213> ORGANISM: Artificial Sequence
<220> FEATURE:
<223> OTHER INFORMATION: PCR primer 5 for Arabidopsis thaliana
      transformation

<400> SEQUENCE: 83
taccgagggg aatttatgga acgtcagtgg ag                               32

<210> SEQ ID NO 84
<211> LENGTH: 31
<212> TYPE: DNA
<213> ORGANISM: Artificial Sequence
<220> FEATURE:
<223> OTHER INFORMATION: PCR primer 6 for Arabidopsis thaliana
      transformation

<400> SEQUENCE: 84
actagtggat cctcgtgtat gttttttaatc t                               31

<210> SEQ ID NO 85
<211> LENGTH: 31
<212> TYPE: DNA
```

```
<213> ORGANISM: Artificial Sequence
<220> FEATURE:
<223> OTHER INFORMATION: PCR primer 7 for Arabidopsis thaliana
      transformation

<400> SEQUENCE: 85
actctgagat taacctatgg ctccccttaa a                                        31

<210> SEQ ID NO 86
<211> LENGTH: 31
<212> TYPE: DNA
<213> ORGANISM: Artificial Sequence
<220> FEATURE:
<223> OTHER INFORMATION: PCR primer 8 for Arabidopsis thaliana
      transformation

<400> SEQUENCE: 86
gaattcgtaa tcatggtcat agctgtttcc t                                        31

<210> SEQ ID NO 87
<211> LENGTH: 42
<212> TYPE: DNA
<213> ORGANISM: Artificial Sequence
<220> FEATURE:
<223> OTHER INFORMATION: PCR primer 9 for Arabidopsis thaliana
      transformation

<400> SEQUENCE: 87
cgaggatcca ctagtatggc caccacctct ttagcttccg ct                            42

<210> SEQ ID NO 88
<211> LENGTH: 40
<212> TYPE: DNA
<213> ORGANISM: Artificial Sequence
<220> FEATURE:
<223> OTHER INFORMATION: PCR primer 10 for Arabidopsis thaliana
      transformation

<400> SEQUENCE: 88
catgattacg aattcaagct ttatcggtaa aacaacgagc                               40

<210> SEQ ID NO 89
<211> LENGTH: 30
<212> TYPE: DNA
<213> ORGANISM: Artificial Sequence
<220> FEATURE:
<223> OTHER INFORMATION: PCR primer 11 for Arabidopsis thaliana
      transformation

<400> SEQUENCE: 89
actagtggat cctcgtgtat gttttttaatc                                         30

<210> SEQ ID NO 90
<211> LENGTH: 30
<212> TYPE: DNA
<213> ORGANISM: Artificial Sequence
<220> FEATURE:
<223> OTHER INFORMATION: PCR primer 12 for Arabidopsis thaliana
      transformation

<400> SEQUENCE: 90
ggcatatggt gtgtatacca cggtgatatg                                          30

<210> SEQ ID NO 91
<211> LENGTH: 38
<212> TYPE: DNA
<213> ORGANISM: Artificial Sequence
```

-continued

```
<220> FEATURE:
<223> OTHER INFORMATION: PCR primer 13 for Arabidopsis thaliana
      transformation

<400> SEQUENCE: 91
cgaggatcca ctagtatgcg ggtctccagt agcgccgt                          38

<210> SEQ ID NO 92
<211> LENGTH: 38
<212> TYPE: DNA
<213> ORGANISM: Artificial Sequence
<220> FEATURE:
<223> OTHER INFORMATION: PCR primer 14 for Arabidopsis thaliana
      transformation

<400> SEQUENCE: 92
tacacaccat atgccttact tgaacggttt gaagatta                          38
```